(12) United States Patent
Phiasivongsa et al.

(10) Patent No.: US 11,708,370 B2
(45) Date of Patent: Jul. 25, 2023

(54) SOLID FORMS OF 2-[3-[4-AMINO-3-(2-FLUORO-4-PHENOXYPHENYL)PYRAZOLO[3,4-D]PYRIMIDIN-1-YL]PIPERIDINE-1-CARBONYL]-4-METHYL-4-[4-(OXETAN-3-YL)PIPERAZIN-1-YL]PENT-2-ENENITRILE

(71) Applicant: Principia Biopharma Inc., South San Francisco, CA (US)

(72) Inventors: Pasit Phiasivongsa, Hillsborough, CA (US); Katherine Chu, San Francisco, CA (US); Jiang Zhu, San Ramon, CA (US); Kolbot By, San Ramon, CA (US); Mohammad Reza Masjedizadeh, San Jose, CA (US)

(73) Assignee: Principia Biopharma Inc., Bridgewater, NJ (US)

( * ) Notice: Subject to any disclaimer, the term of this patent is extended or adjusted under 35 U.S.C. 154(b) by 65 days.

(21) Appl. No.: 17/125,384

(22) Filed: Dec. 17, 2020

(65) Prior Publication Data
US 2021/0198264 A1    Jul. 1, 2021

Related U.S. Application Data

(60) Provisional application No. 62/951,958, filed on Dec. 20, 2019, provisional application No. 63/122,309, filed on Dec. 7, 2020.

(51) Int. Cl.
*A61K 31/519* (2006.01)
*C07D 487/04* (2006.01)

(52) U.S. Cl.
CPC ................ *C07D 487/04* (2013.01)

(58) Field of Classification Search
CPC .................. A61K 31/519; C07D 487/04
USPC ...................... 514/262.1; 544/262
See application file for complete search history.

(56) References Cited

FOREIGN PATENT DOCUMENTS

| CN | 110483521 A | 11/2019 |
|---|---|---|
| WO | 2014039899 A1 | 3/2014 |
| WO | 2015127310 A1 | 8/2015 |
| WO | 2022081512 A1 | 4/2022 |

OTHER PUBLICATIONS

Ghoroi, Chinmay et al., "Multi-faceted characterization of pharmaceutical powders to discern the influence of surface modification", Powder Technology, vol. 236, May 22, 2012, pp. 63-74.
Shekunov, B Y et al., "Crystallization processes in pharmaceutical technology and drug delivery design", Journal of Crystal Growth, vol. 211, No. 104, Apr. 1, 2000, pp. 122-136.
International Search Report for PCT/US2020/065689 dated Apr. 29, 2021 (9 pages).
Mahoney, M.G., et al., "Explanations for the clinical and microscopic localization of lesions in pemphigus foliaceus and vulgaris," Journal of Clinical Investigation, vol. 103, No. 4, pp. 461-468 (1999).
Maronpot, R.R., et al., "Hepatic Enzyme Induction: Histopathology," Toxicologic Pathology, vol. 38, pp. 776-795 (2010).
McKenzie, C.G., et al., "Cellular immune dysfunction in immune thrombocytopenia," British Journal of Haematology, vol. 163, pp. 10-23 (2013).
Metz, M., et al., "Fenebrutinib in H1 antihistamine-refractory chronic spontaneous urticaria: a randomized phase 2 trial," Nature Medicine, vol. 27, No. 11, pp. 1961-1969 (2021).
Michel, M., et al., "A randomized and double-blind controlled trial evaluating the safety and efficacy of rituximab for warm autoimmune hemolytic anemia in adults (the RAIHA study)," American Journal of Hematology, vol. 92, No. 1, pp. 23-27 (2017).
Mohamed, A.J., et al., Bruton's tyrosine kinase (Btk): function, regulation, and transformation with special emphasis on the PH domain, Immunology Review, vol. 228, pp. 58-73 (2009).
Montillo, M., et al., "Ibrutinib in previously treated chronic lymphocytic leukemia patients with autoimmune cytopenias in the Resonate study," Blood Cancer Journal 7, No. e524 Letter to the Editor (2017).
Murrell, D.F., et al., "Diagnosis and Management of Pemphigus: recommendations by an International Panel of Experts," Journal of American Academy of Dermatology (2018).
Neys, S., et al., "Targeting Bruton's Tyrosine Kinase in Inflammatory and Autoimmune Pathologies," Frontiers in Cell & Developmental Biology, vol. 9, p. 668131 (2021).

(Continued)

*Primary Examiner* — Douglas M Willis
(74) *Attorney, Agent, or Firm* — McNeill Baur PLLC

(57) ABSTRACT

Solid forms of Compound (I):

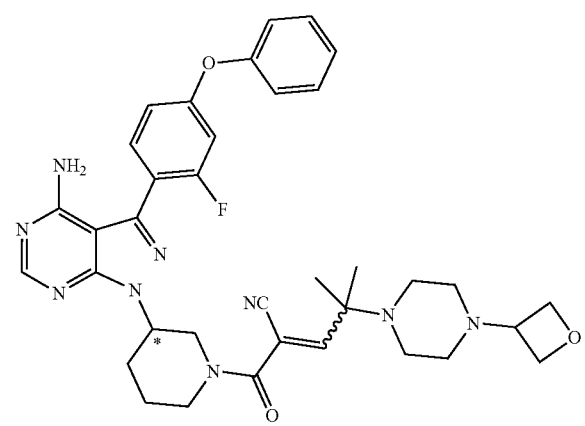

are disclosed. Pharmaceutical compositions comprising the same, methods of treating disorders and conditions mediated by BTK activity using the same, and methods for making Compound (I) and solid forms thereof are also disclosed.

16 Claims, 16 Drawing Sheets

(56) References Cited

OTHER PUBLICATIONS

Porro, A.M., et al., "Pemphigus vulgaris," Anais Brasileiros de Dermatologia, vol. 94, No. 3, pp. 264-278 (2019).
Press Release, "Sanofi to acquire Principia Biopharma," Aug. 17, 2020.
Rankin, A.L., et al., "Selective inhibition of BTK prevents murine lupus and antibody-mediated glomerulonephritis," Journal of Immunology, vol. 191, No. 9, pp. 4540-4550 (2012).
Rip, J., et al., "The role of Bruton's tyrosine kinase in immune cell signaling and systemic autoimmunity," Critical Reviews in Immunology, vol. 38, No. 1, pp. 17-62 (2018).
Roumier, M., et al., "Characteristics and outcome of warm autoimmune hemolytic anemia in adults: New insights based on a single-center experience with 60 patients," American Journal of Hematology, vol. 89, No. 9, pp. E150-E155 (2014).
Saloojee, Y., et al., "Carboxyhaemoglobin and plasma thiocyanate: complementary indicators of smoking behaviour," Thorax, vol. 37, No. 7, pp. 521-525 (1982).
Serafimova, I.M., et al., "Reversible targeting of noncatalytic cysteines with chemically tuned electrophiles," Nature Chemical Biology, vol. 8, No. 5, pp. 471-476 (2012).
Sideras, P., et al., "Molecular and cellular aspects of X-linked agammaglobulinemia," Advanced Immunology, vol. 59, pp. 135-223 (1995).
Storim, J., et al., "Dose-finding Phase 2 study to evaluate the efficacy and safety of the novel BTK inhibitor LOU064 in patients with CSU inadequately controlled by H1-antihistamines," Poster from 28th European Academy of Dermatology and Venereology Congress, Oct. 9-13, 2019 in Madrid, Spain.
Taylor, I., et al., "Comparison of longevity and common tumor profiles between Sprague-Dawley and Han Wistar rats," Journal of Toxicology & Pathology, vol. 33, pp. 189-196 (2020).
Unniappan, S., et al., "Leptin extends the anorectic effects of chronic PYY (3-36) administration in ad libitum-fed rats," American Journal of Physiology—Regulatory, Integrative and Comparitive Physiology, vol. 295, No. 1, pp. R51-R58 (2008).
Weber, A.N., "Targeting the NLRP3 Inflammasome via BTK," Frontiers in Cell and Developmental Biology, vol. 9, p. 630479 (2021).
Weber, K., "Differences in types and incidence of neoplasms in Wistar Han and Sprague-Dawley rats," Toxicology & Pathology, vol. 45, No. 1, pp. 64-75 (2017).
Wree, A., et al., "NLRP3 inflammasome activation results in hepatocyte pyroptosis, liver inflammation, and fibrosis in mice," Hepatology, vol. 59, No. 3, pp. 898-910 (2014).
Zanella, A., et al., "Treatment of autoimmune hemolytic anemias," Haematologica, vol. 99, No. 10, pp. 1547-1554 (2014).
Zhang, D., et al., "Recent Advances in BTK Inhibitors for the Treatment of Inflammatory and Autoimmune Diseases," Molecules, vol. 26, No. 16, p. 4907 (2021).
Anderson, R.C., et al., "Absorption and Toxicity of Sodium and Potassium Thiocyanates," Journal of American Pharmacists Association, vol. 29, No. 4, pp. 152-161 (1940).
Barker, M.H., "The Blood Cyanates in the Treatment of Hypertension," Journal of American Medical Association, vol. 106, No. 10, pp. 762-767 (1936).
Barker, M.H., et al., "Further Experiences with Thiocyanates," Journal of American Medical Association, vol. 117, No. 9, pp. 1591-1594 (1941).
Bartsch, R., et al., "Human relevance of follicular thyroid tumors in rodents caused by non-genotoxic substances," Regulatory Toxicology & Pharmacology, vol. 98, pp. 199-208 (2018).
Beissert, S., et al., "A comparison of oral methylprednisolone plus azathioprine or mycophenolate mofetil for the treatment of pemphigus," Archives of Dermatology, vol. 142, No. 11, pp. 1447-1454 (2006).
Bizikova, P., et al., "Cloning and establishment of canine desmocollin-1 as a major autoantigen in canine pemphisgus foliaceus," Veterinary Immunology & Immunopathology, vol. 149, pp. 197-207 (2012).
Butt, M.T., et al., "Nervous System: Astrocytosis," In Toxicologic Pathology Nonclinical Safety Assessment, Sahota, P.S., Popp, J.A., Hardistry, J.F., and Gopinath, C. (eds), vol. 20, pp. 901-903 (2013).
Byrd, J.C., et al., "Acalabrutinib (ACP-196) in relapsed chronic lymphocytic leukemia," New England Journal of Medicine, vol. 374, No. 4, pp. 323-332 (2016).
Chaplin, H., Jr., "Clinical usefulness of specific antiglobulin reagents in autoimmune hemolytic anemias," Hematology Program, vol. 8, pp. 25-49 (1973).
Eaton, W.W., et al., "Epidemiology of autoimmune diseases in Denmark," Journal of Autoimmunity, vol. 29, No. 1, pp. 1-9 (2007).
Gao, Y., et al., "Hormones and diet, but not body weight, control hypothalamic microglial activity," Glia, vol. 62, pp. 17-25 (2014).
Garvin, C.F., "The Fatal Toxic Manifestations of the Thiocyanates," Journal of American Medical Association, vol. 112, No. 12, pp. 1125-1127 (1939).
Gordon, R., et al., "Inflammasome inhibition prevents alpha-synuclein pathology and dopaminergic neurodegeneration in mice," Science Translational Medicine, vol. 10, No. 465, p. eaah4066 (2018).
Horvath, B., et al., "Low dose rituximab is effective in pemphigus," British Journal of Dermatology, vol. 166, No. 2, pp. 405-412 (2012).
Ivankovic, S., Fehlende teratogene Wirkung von Nitroprussidnatrium (NNP) an Wistar-Ratten und Kaninchen [Absence of a teratogenic effect of sodium nitroprusside in wistar rats and rabbits (author's transl)]. Arzneimittelforschung, vol. 29, No. 8, pp. 1092-1094 (1979). English Abstract.
Jager, U., et al., "Diagnosis and treatment of autoimmune hemolytic anemia in adults: Recommendations from the First International Consensus Meeting," Blood Review, vol. 41, p. 100648 (2020).
Joly, P., et al., "First-line rituximab combined with short-term prednisone versus prednisone alone for the treatment of pemphigus (Ritux 3): a prospective, multicentre, parallel-group, open-label randomised trial," Lancet, vol. 389, No. 10083, pp. 2031-2040 (2017).
Joly, P., et al., "Pemphigus group (vulgaris, vegetans, foliaceus, herpetiformis, brasiliensis)," Clinical Dermatology, vol. 29, No. 4, pp. 432-436 (2011).
Kihlman, B.A., "Experimentally Induced Chromosome Aberrations in Plants, I. The production of chromosome aberrations by cyanide and other heavy metal complexing agents," Journal of Biophysical & Biochemical Cytology, vol. 3, No. 3, pp. 363-380 (1957).
Kuter, D.J., et al., "Rilzabrutinib, an Oral BTK Inhibitor, in Immune Thrombocytopenia," MEJM Paper, vol. 386, No. 15, pp. 1421-1431 (2022).
Kuter, D.J., et al., "Safety and efficacy of rilzabrutinib (PRN1008), an oral Bruton tyrosine kinase inhibitor, in relapsed/refractory patients with primary or secondary immune thrombocytopenia: Phase I/II adaptive study," European Hematology Association (EHA) annual meeting, vol. 4, No. S1, pp. 118-119 (abstract S316) poster presentation (2020).
Lindberg, H.A., et al., "Observations of the Pathologic Effects of Thiocyanate: An Experimental Study," American Heart Journal, vol. 21, No. 5, pp. 605-616 (1941).
Martin, Y.C., et al., "Do structurally similar molecules have similar biological activity?," Journal of Medicinal Chemistry, vol. 45, No. 19, pp. 4350-4538 (2002).
Masters, S.L., et al., "Activation of the NLRP3 inflammasome by islet amyloid polypeptide provides a mechanism for enhanced IL-1Beta in type 2 diabetes," Nature Immunology, vol. 11, No. 10, pp. 897-904 (2010).
Michel, M., "Classification and therepeutic approaches in autoimmune hemolytic anemia: an update," Expert Review of Hematology, vol. 4, No. 6, pp. 607-618 (2011).
Mosher, K.I., et al., "Go with your gut: microbiota meet microglia," Nature Neuroscience, vol. 18, pp. 930-931 (2015).
Nagasawa, H., et al., "Inhibitory effects of potassium thiocyanate on normal and neoplastic mammary development in female mice," European Journal of Cancer, vol. 16, No. 4, pp. 473-480 (1980).
Newman, K., et al., "Management of immune cytopenias in patients with systemic lupus erythematosus," Autoimmunity Reviews, vol. 12, No. 7, pp. 784-791 (2013).

(56) References Cited

OTHER PUBLICATIONS

Rogers, K.A., et al., "Incidence and description of autoimmune cytopenias during treatment with ibrutinib for chronic lymphocytic leukemia," Leukemia, vol. 30, pp. 346-350 (2016).
Schwab, I., et al., "Intravenous immunoglobulin therapy: how does IgG modulate the immune system?," Nature Reviews Immunology, vol. 13, pp. 176-189 (2013).
Streicher, E., et al., "Distribution of thiocyanate between plasma and cerebrospinal fluid," American Journal of Physiology, vol. 206, No. 2, pp. 251-254 (1964).
Tan, S., et al., "Targeting the SYK-BTK axis for the treatment of immunological and hematological disorders: Recent progress and therapeutic perspectives," Pharmacological Therapy, vol. 138, No. 2, pp. 294-309 (2013).
Weber, A.N., et al., "Bruton's tyrosine kinase: an emerging key player in innate immunity," Frontiers in Immunology, vol. 8, p. 1454 (2017).
Xu, D., et al., "RN486, a selective Bruton's tyrosine kinase inhibitor, abrogates immune hypersensitivity responses and arthritis in rodents," Journal of Pharmacology & Experimental Therapy, vol. 341, pp. 90-103 (2012).
Yamaguchi, T., "Mutagenicity of Isothiocyanates, Isocyanates and Thioureas on *Salmonella typhimurium*," Agricultural Biology & Chemistry, vol. 44, No. 12, pp. 3017-3018 (1980).
Advani, R.H., et al., "Bruton tyrosine kinase inhibitor ibrutinib (PCI-32765) has significant activity in patients with relapsed/refractory B-cell malignancies," Journal of Clinical Oncology, vol. 31, No. 1, pp. 88-94 (2013).
American College of Rheumatology; ACR COVID-19 Vaccine Clinical Guidance Task Force, "COVID-19 vaccine clinical guidance summary for patients with rheumatic and musculoskeletal diseases," https://www.rheumatology.org/Portals/0/Files/COVID-19-Vaccine-Clinical-Guidance-Rheumatic-Diseases-Summary.pdf, cited May 10, 2021.
Banerjee, K.K., et al., "Effect of thiocyanate ingestion through milk on thyroid hormone homeostasis in women," British Journal of Nutrition, vol. 78, No. 5, pp. 679-681 (1997).
Barcellini, W., et al., "Clinical heterogeneity and predictors of outcome in primary autoimmune hemolytic anemia: a GIMEMA study of 308 patients," Blood, vol. 124, No. 19, pp. 2930-2936 (2014).
Bhandari, R.K., et al., "Cyanide toxicokinetics: the behavior of cyanide, thiocyanate and 2-amino-2-thiazoline-4-carboxylic acid in multiple animal models," Journal of Analytical Toxicology, vol. 38, No. 4, pp. 218-225 (2014).
Bizikova, P., et al., "Serum autoantibody profiles of IgA, IgE and IgM in canine pemphigus foliaceus," Veterinary Dermatology, vol. 25, pp. 471-475 (2014).
Bolon, B., et al., "STP Position Paper: Recommended Practices for Sampling and Processing the Nervous System (Brain, Spinal Cord, Nerve, and Eye) during Nonclinical General Toxicity Studies," Toxicologic Pathology, vol. 41, pp. 1028-1048 (2013).
Borthakur, G., et al., "Immune anaemias in patients with chronic lymphocytic leukaemia treated with fludarabine, cyclophosphamide and rituximab-incidence and predictors," British Journal of Haematology, vol. 136, No. 6, pp. 800-805 (2007).
Bradshaw, J.M., et al., "Prolonged and tunable residence time using reversible covalent kinase inhibitors," Nature Chemical Biology, vol. 11, No. 7, pp. 525-531 (2015).
Brodsky, R.A., "Warm Autoimmune Hemolytic Anemia," New England Journal of Medicine, vol. 381, No. 7, pp. 647-654 (2019).
Brown, J.R., et al., "Phase I study of single-agent CC-292, a highly selective Bruton's tyrosine kinase inhibitor, in relapsed/refractory chronic lymphocytic leukemia," Haematologica, vol. 101, p. e295 (2016).
Burger, J.A., "Bruton Tyrosine Kinase Inhibitors: Present and Future," Cancer Journal, vol. 25, No. 6, pp. 386-393 (2019).
Burger, J.A., et al., "Randomized Trial of Ibrutinib Versus Ibrutinib Plus Rituximab (Ib+R) in Patients with Chronic Lymphocytic Leukemia (CLL)," Blood, vol. 130, p. 427 (2017).

Bussel, J.B., et al., "Eltrombopag for the treatment of chronic idiopathic thrombocytopenic purpura," New England Journal of Medicine, vol. 357, pp. 2237-2247 (2007).
Carnero-Contentti, E., et al., "Bruton's tyrosine kinase inhibitors: a promising emerging treatment option for multiple sclerosis," Expert Opinion on Emerging Drugs, vol. 25, No. 4, pp. 377-381 (2020).
Chandler, J.D., et al., "Biochemical Mechanisms and Therapeutic Potential of the Pseudohalide Thiocyanate in Human Health," Free Radical Research, vol. 49, No. 6, pp. 695-710 (2015).
Chang, B.Y., et al., "The Bruton tyrosine kinase inhibitor PCI-32765 ameliorites autoimmune arthritis by inhibition of multiple effector cells," Arthritis Research & Therapy, vol. 13, No. 4, p. R115 (2011).
Chaudhri, O.B., et al., "Can Gut Hormones Control Appetite and Prevent Obesity?," Diabetes Care, vol. 31, pp. S284-S289 (2008).
Chen, J.F., et al., "The clinical significance of circulating B cells and secreting anti-glycoprotein IIb/IIIa antibody and platelet glycoprotein IIb/IIIa in patients with primary immune thrombocytopenia," Hematology, vol. 15, pp. 283-290 (2013).
Code of Federal Regulations, Title 21, Chapter II, Part 1308, Schedules of Controlled Substances, Mar. 12, 2021.
Crowther, M., et al., "Evidence-based focused review of the treatment of idiopathic warm immune hemolytic anemia in adults," Blood, vol. 118, No. 15, pp. 4036-4040 (2011).
DeSilva, A., et al., "Gut Hormones and Appetite Control: A Focus on PYY and GLP-1 as Therapeutic Targets in Obesity," Gut Liver, vol. 6, No. 1, pp. 10-20 (2012).
Dierickx, D., et al., "Rituximab in autoimmune haemolytic anaemia and immune thrombocytopenic purpura: a Belgian retrospective multicentric study," Journal of Internal Medicine, vol. 266, No. 5, pp. 484-491 (2009).
DiPaolo, J.A., et al., "Specific Btk inhibition suppresses B cell- and myeloid cell-mediated arthritis," Nature Chemical Biology, vol. 7, pp. 41-50 (2011).
Dispenza, M.C., et al., "Bruton's tyrosine kinase inhibition effectively protects against human IgE-mediated anaphylaxis," Journal of Clinical Investigation, vol. 130, No. 9, pp. 4759-4770 (2020).
Elizondo-Vega, R., et al., "The role of tanycytes in hypothalamic glucosensing," Journal of Cellular and Molecular Medicine, vol. 19, pp. 1471-1482 (2015).
Fayyaz, A., et al., "Haematological manifestations of lupus," Lupus Science & Medicine, vol. 2, No. 1, p. e000078 (2015).
Futatani, T., et al., "Bruton's tyrosine kinase is present in normal platelets and its absence identifies patients with X-linked agammaglobulinaemia and carrier females," British Journal of Haematology, vol. 114, No. 1, pp. 141-149 (2001).
Goodman, T., et al., "Hypothalamic tanycytes—masters and servants of metabolic, neuroendocrine, and neurogenic functions," Frontiers in Neuroscience, vol. 9, p. 387 (2015).
GRAS notification for sodium thiocyanate for use in the lactoperoxidase system, https://www.fda.gov/files/food/published/GRAS-Notice-GRN-753pdf.
Gregoriou, S., et al., "Management of pemphigus vulgaris: challenges and solutions," Clinical, Cosmetic & Investigational Dermatology, vol. 8, pp. 521-527 (2015).
Heneka, M.T., et al., "NLRP3 is activated in Alzheimer's disease and contributes to pathology in APP/PS1 mice," Nature, vol. 492, No. 7434, pp. 674-678 (2013).
Hertl, M., et al., "Pemphigus. S2 Guideline for diagnosis and treatment—guided by the European Dermatology Forum (EDF) in cooperation with the European Academy of Dermatology and Venereology (EADV)," Journal of the European Academy of Dermatology and Venereology, vol. 29, No. 3, pp. 405-414 (2015).
Hill, Q.A., et al., "The diagnosis and management of primary autoimmune haemolytic anaemia," British Journal of Haematology, vol. 176, No. 3, pp. 395-411 (2017).
Hodgson, K., et al., "Autoimmune cytopenia in chronic lymphocytic leukemia: diagnosis and treatment," British Journal of Haematology, vol. 154, No. 1, pp. 14-22 (2011).
Honigberg, L.A., et al., "The Bruton tyrosine kinase inhibitor PCT-32765 blocks B-cell activation and is efficacious in models of autoimmune disease and B-cell malignancy," PNAS, vol. 107, pp. 13075-13080 (2010).

(56) References Cited

OTHER PUBLICATIONS

Hutcheson, J., et al., "Modulating proximal cell signaling by targeting Btk ameliorates humoral autoimmunity and end-organ disease in murine lupus," Arthritis Research & Therapy, vol. 14, pp. R243 (2012).

Ihrke, P.J., et al., "Pemphigus foliaceus in dogs: a review of 37 cases," Journal of the American Veterinary Medical Association, vol. 186, No. 1, pp. 59-66 (1985).

Irwin, S., "Comprehensive observational assessment: Ia. A systematic, quantitative procedure for assessing the behavioral and physiologic state of the mouse," Psychopharmacologia, vol. 13, No. 3, pp. 222-257 (1968).

Ito, M., et al., "Bruton's tyrosine kinase is essential for NLRP3 inflammasome activation and contributes to ischaemic brain injury," Nature Communications, vol. 6, No. 1, p. 1 (2015).

Karra, E., et al., "The role of peptide YY in appetite regulation and obesity," Journal of Physiology, vol. 587, No. 1, pp. 19-25 (2009).

Khellaf, M., et al., "Safety and efficacy of rituximab in adult immune thrombocytopenia: results from a prospective registry including 248 patients," Blood, vol. 124, No. 22, pp. 3228-3236 (2014).

Kim, K.H., et al., "Imidazo[1.5-a]quinoxalines as irreversible BTK inhibitors for the treatment of rheumatoid arthritis," Bioorganic & Medicinal Chemical Letters, vol. 21, pp. 6258-6263 (2011).

Klein, N.P., et al., "Rates of autoimmune diseases in Kaiser Permanente for use in vaccine adverse event safety studies," Vaccine, vol. 28, No. 4, pp. 1062-1068 (2010).

Kohrt, H.E., et al., "Ibrutinib antagonizes rituximab-dependent NK cell-mediated cytotoxicity," Blood, vol. 123, No. 12, pp. 1957-1960 (2014).

Kridin, K., et al., "Mortality and Cause of Death in Patients with Pemphigus," Acta Dermato-Venereologica, vol. 97, No. 5, pp. 607-611 (2017).

Kuter, D.J., et al., "22 oral rilzabrutinib Bruton tyrosine kinase inhibitor, showed clinically active and durable platelet responses and was well-tolerated in patients with heavily pretreated immune thrombocytopenia," 62nd ASH Annual Meeting & Exposition, Abstract (presentation) (Dec. 5-8, 2020).

Kuter, D.J., et al., "Phase I/II, open-label, adaptive study of oral tyrosine inhibitor patients with relapsed/refractory primary or secondary immune thrombodytopenia," Blood, vol. 134 (Suppl 1), p. 87 (2019).

Langrish, C., et al., Preclinical Efficacy and Anti-Inflammatory Mechanisms of Action of the Bruton Tyrosine Kinase Inhibitor Rilzabrutinib for Immune-Mediated Disease, Journal of Immunology, vol. 206, No. 7, pp. 1454-1486 (2021).

Lipsky, A., et al., Managing toxicities of Bruton tyrosine kinase inhibitors, Hematology, American Society of Hematology Education Program, vol. 2020, No. 1, pp. 336-345 (2020).

SOLID FORMS OF 2-[3-[4-AMINO-3-(2-FLUORO-4-PHENOXYPHENYL)PYRAZOLO[3,4-D]PYRIMIDIN-1-YL]PIPERIDINE-1-CARBONYL]-4-METHYL-4-[4-(OXETAN-3-YL)PIPERAZIN-1-YL]PENT-2-ENENITRILE

This application claims the benefit of priority to U.S. Provisional Application No. 62/951,958, filed Dec. 20, 2019, and U.S. Provisional Application No. 63/122,309, filed Dec. 7, 2020, the contents of each of which are incorporated by reference herein in their entirety.

Disclosed herein are solid forms of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile (Compound (I)), methods of using the same, and processes for making Compound (I), including its solid forms. The solid forms of Compound (I) may be inhibitors of Bruton's tyrosine kinase (BTK) comprising low residual solvent content.

The enzyme BTK is a member of the Tec family non-receptor tyrosine kinases. BTK is expressed in most hematopoietic cells, including B cells, mast cells, and macrophages. BTK plays a role in the development and activation of B cells. BTK activity has been implicated in the pathogenesis of several disorders and conditions, such as B cell-related hematological cancers (e.g., non-Hodgkin lymphoma and B cell chronic lymphocytic leukemia) and autoimmune diseases (e.g., rheumatoid arthritis, Sjogren's syndrome, *Pemphigus*, IBD, lupus, and asthma).

Compound (I), pharmaceutically acceptable salts thereof, and solid forms of any of the foregoing may inhibit BTK and be useful in the treatment of disorders and conditions mediated by BTK activity. Compound (I) is disclosed in Example 31 of WO 2014/039899 and has the following structure:

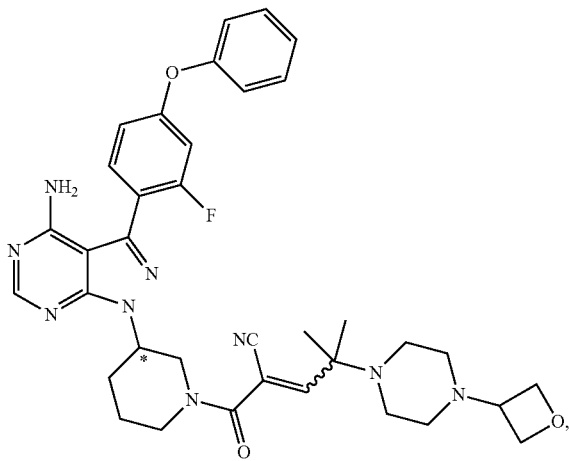 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

where *C is a stereochemical center. An alternative procedure for producing Compound (I) is described in Example 1 of WO 2015/127310.

Compound (I) obtained by the procedures described in WO 2014/039899 and WO 2015/127310 comprises residual solvent levels well above the limits described in the International Conference on Harmonization of Technical Requirements for Registration of Pharmaceuticals for Human Use ("ICH") guidelines. In general, manufacturing processes producing residual solvent levels near or above the ICH limits are not desirable for preparing active pharmaceutical ingredients (APIs).

Solid forms of bioactive compounds, such as Compound (I) and pharmaceutically acceptable salts thereof, are of interest in the pharmaceutical industry, where solid forms with specific physical, chemical, or pharmaceutical properties, such as solubility, dissociation, true density, dissolution, melting point, morphology, compaction behavior, particle size, flow properties, or solid state stability, may be desirable or even required for pharmaceutical development. The solid state form of a bioactive compound often determines its ease of preparation, ease of isolation, hygroscopicity, stability, solubility, storage stability, ease of formulation, rate of dissolution in gastrointestinal fluids, and in vivo bioavailability.

Furthermore, it is critical that solid forms intended for use as APIs in therapeutic compositions are substantially pure. Specifically, substantially pure forms are free from reaction impurities, starting materials, reagents, side products, unwanted solvents, and/or other processing impurities arising from the preparation and/or isolation and/or purification of the particular solid form. Illustratively, solid forms intended for use as APIs should be substantially free of degradation products, including drug substance aggregates (e.g., dimers of the API).

It is not yet possible to predict the possible solid forms of a compound or salt, whether any such forms will be suitable for commercial use in a pharmaceutical composition, or which form or forms will display desirable properties. Because different solid forms may possess different properties, reproducible processes for producing a substantially pure solid form, including large-scale manufacturing processes, are also desirable for bioactive compounds intended for use as pharmaceuticals.

Accordingly, there is a need for novel solid forms which are useful for treating disorders and conditions mediated by BTK activity, such as, e.g., Compound (I) and pharmaceutically acceptable salts thereof, and reproducible, scalable methods of making the same.

Disclosed herein are novel solid forms of Compound (I), compositions comprising the same, and methods of using and making the same. Importantly, in some embodiments, the solid forms of Compound (I) have low residual solvent levels. Moreover, in some embodiments, the solid forms of Compound (I) are substantially free of degradation products (such as, e.g., dimers of Compound (I)). In some embodiments, the novel solid forms disclosed herein have properties that are useful for large-scale manufacturing, pharmaceutical formulation, pharmaceutical use, and/or storage. In some embodiments, the novel solid forms disclosed herein include no detectable residual solvent in the solid forms. In some embodiments, the solid forms are substantially amorphous. Also disclosed herein are novel methods of making Compound (I).

Some embodiments of the disclosure relate to a solid form of Compound (I) characterized by a mean bulk density greater than 0.3 g/cc. Some embodiments of the disclosure relate to a solid form of Compound (I) characterized by a mean tapped density greater than 0.5 g/cc.

Some embodiments of the disclosure relate to a solid form of Compound (I) characterized by a Hausner ratio less than or equal to 1.2.

Some embodiments of the disclosure relate to a solid form of Compound (I) characterized by a wet particle size distribution having a $D_{10}$ value greater than 70 μm. Some embodiments of the disclosure relate to a solid form of Compound (I) characterized by a wet particle size distribution having a $D_{50}$ value greater than 200 μm. Some embodiments of the disclosure relate to a solid form of Compound (I) characterized by a wet particle size distribution having a $D_{90}$ value greater than 400 μm.

Some embodiments of the disclosure relate to a solid form of Compound (I) characterized by a wet particle size distribution having a $D_{10}$ value less than 10 μm. Some embodiments of the disclosure relate to a solid form of Compound (I) characterized by a wet particle size distribution having a $D_{50}$ value less than 100 μm. Some embodiments of the disclosure relate to a solid form of Compound (I) characterized by a wet particle size distribution having a $D_{90}$ value less than 200 μm.

Some embodiments of the disclosure relate to a solid form of Compound (I) characterized by a mass loss of less than 5 wt. % between 20° C. and 240° C. by thermogravimetric analysis. Some embodiments of the disclosure relate to a solid form of Compound (I) characterized by a glass transition temperature ($T_g$) greater than 90° C. at 0% relative humidity.

Some embodiments of the disclosure relate to a solid form of Compound (I), wherein the total level of residual solvents in the solid form is less than 1%. Some embodiments of the disclosure relate to a solid form of Compound (I), wherein there is no detectable residual solvent in the solid form.

Some embodiments of the disclosure relate to a solid form of Compound (I), wherein the solid form is substantially pure.

Some embodiments of the disclosure relate to a solid form of Compound (I), wherein the solid form is substantially free of degradation products. In some embodiments, solid forms of Compound (I) are substantially free of dimers of Compound (I). In some embodiments, solid forms of Compound (I) are substantially free of dimers of Compound (I) having the following chemical structure:

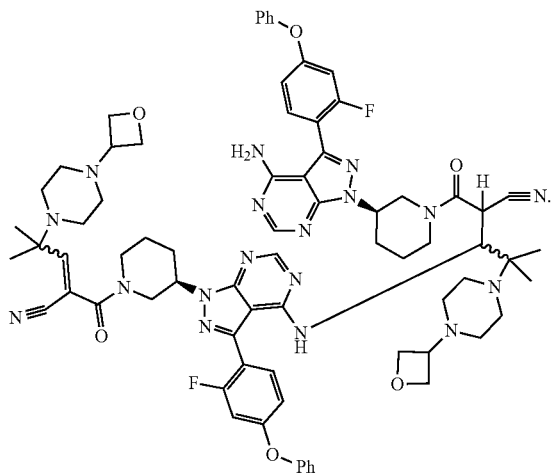 [SMILES: CC(C)(C=C(C#N)C(=O)N1CCC[C@@H](n2nc(-c3ccc(Oc4ccccc4)cc3F)c3c(NC(C(C#N)C(=O)N4CCC[C@@H](n5nc(-c6ccc(Oc7ccccc7)cc6F)c6c(N)ncnc65)C4)C(C)(C)N4CCN(C5COC5)CC4)ncnc32)C1)N1CCN(C2COC2)CC1]

Some embodiments of the disclosure relate to a solid form of Compound (I), wherein the solid form is substantially amorphous.

Some embodiments of the disclosure relate to a pharmaceutical composition comprising: at least one solid form of Compound (I); and at least one pharmaceutically acceptable excipient. In some embodiments, the at least one solid form of Compound (I) is a solid form described herein. In some embodiments, the pharmaceutical composition is in the form of a solid oral composition. In some embodiments, the pharmaceutical composition is in the form of a tablet or a capsule.

Some embodiments of the disclosure relate to methods of inhibiting Bruton's tyrosine kinase (BTK) in a mammal comprising administering to the mammal a therapeutically effective amount of at least one solid form of Compound (I). In some embodiments, the at least one solid form of Compound (I) is a solid form described herein. Some embodiments of the disclosure relate to methods of treating a disease mediated by BTK in a mammal comprising administering to the mammal a therapeutically effective amount of at least one solid form of Compound (I). In some embodiments, the at least one solid form of Compound (I) is a solid form described herein. In some embodiments, the disease mediated by BTK is *Pemphigus vulgaris*. In some embodiments, the disease mediated by BTK is *Pemphigus foliaceus*. In some embodiments, the disease mediated by BTK is immune thrombocytopenia. In some embodiments, the mammal is a human.

Also provided herein are methods of preparing at least one solid form of Compound (I).

In some embodiments, the methods comprise the step of adding a base to an aqueous solution comprising Compound (I). In some embodiments, the methods comprise the steps of: washing a solution of Compound (I) with a first aqueous acidic solution to create a first solution comprising a first organic layer and a first aqueous layer, wherein the solution of Compound (I) comprises a first organic solvent; and removing the first aqueous layer. In some embodiments, the methods further comprise the steps of: partially removing the first organic solvent from the first organic layer; adding a second organic solvent to the first organic layer, wherein the first organic solvent and the second organic solvent are not the same; and adding a second aqueous acidic solution to create a second solution comprising a second organic layer and a second aqueous layer, wherein the second aqueous layer comprises Compound (I). In some alternative embodiments, the methods further comprise the steps of: adding a first organic acid to the first organic layer; concentrating the first organic layer to remove at least 70% of the first organic solvent; adding a third organic solvent to the first organic layer to create a third solution comprising a third organic layer and a third aqueous layer, wherein the third aqueous layer comprises Compound (I) and further wherein the first organic solvent and the third organic solvent are not the same; and adding a first base to adjust the pH of the third aqueous layer to between 2.5 and 3.5. In some embodiments, the methods further comprise the steps of: removing the second organic layer or the third organic layer; removing residual organic solvent in the second aqueous layer or the third aqueous layer to create an aqueous solution of Compound (I); and adding a second base to the aqueous solution of Compound (I) to create a precipitate comprising Compound (I). In some embodiments, the methods further comprise the step of micronizing the precipitate comprising Compound (I).

In some embodiments, the methods comprise washing a solution comprising Compound (I) and an organic solvent with an aqueous solution of a weak organic acid having a pKa less than or equal to 7 (≤7) to create a first organic layer and a first aqueous layer; and removing the first aqueous layer, leaving behind the first organic layer comprising Compound (I).

In some embodiments, the methods further comprise washing the first organic layer comprising Compound (I) with aqueous sodium bicarbonate. In some embodiments, washing the first organic layer comprising Compound (I) removes substantially all of the weak organic acid having a pKa≤7.

In some embodiments, the methods further comprise adding a strong acid to the first organic layer; and concentrating the first organic layer by removing the organic solvent to provide a residue comprising Compound (I).

In some embodiments, the methods further comprise cooling the residue comprising Compound (I) to a temperature between 0° C. and 10° C. In some embodiments, the methods further comprise washing the residue comprising Compound (I) with water or an aqueous salt solution.

In some embodiments, the methods further comprise adding a water-immiscible organic solvent to the first aqueous layer to provide a second organic layer, and a second aqueous layer comprising Compound (I); and removing the second organic layer.

In some embodiments, the methods further comprise adjusting the pH of the first or second aqueous layer to a value between 1 and 5 by adding an aqueous base.

In some embodiments, the methods further comprise determining a level of residual weak organic acid having a pKa≤7 in the first or second aqueous layer, and adjusting the level of the level of the weak organic acid having a pKa≤7 to 0 wt. % to 8 wt. %.

In some embodiments, the methods further comprise adding an aqueous base to the first or second aqueous layer to obtain a pH between 8 and 11 and allowing a precipitate comprising Compound (I) to form. In some embodiments, the methods further comprise isolating the precipitate comprising Compound (I) by filtering, and washing the isolated precipitate comprising Compound (I) with water. In some embodiments, the methods further comprise drying the filtered and washed precipitate comprising Compound (I) to provide a solid form of Compound (I). In some embodiments, the methods further comprise slurrying the isolated precipitate with water and filtering to isolate a solid form of Compound (I).

In some embodiments, the methods comprise dissolving a crystalline form of Compound (I) in a solution comprising a water-immiscible organic solvent and brine; adding one equivalent of a strong acid to create an aqueous layer and an organic layer; removing the organic layer; concentrating the aqueous layer; adding an aqueous base to adjust the pH to a value between 8 and 11 to obtain a precipitate of a solid form of Compound (I); isolating the precipitate of the solid form of Compound (I) by filtering; rinsing the precipitate with water; and drying the precipitate to obtain a solid form of Compound (I).

In some embodiments, the methods comprise the step of spray drying a solution of Compound (I).

In some embodiments, the methods comprise the steps of: washing a solution of Compound (I) with a first aqueous acidic solution to create a first solution comprising a first organic layer and a first aqueous layer, wherein the solution of Compound (I) comprises a first organic solvent; removing the first aqueous layer; and performing a solvent exchange from the first organic solvent to a second organic solvent. In some embodiments, the methods further comprise the steps of: washing the first organic layer with a second aqueous acidic solution to create a second solution comprising a second organic layer and a second aqueous layer, wherein the second aqueous layer comprises Compound (I); and removing the second organic layer. In some embodiments, the methods further comprise the steps of: adding a first base to the second aqueous layer to create a third solution comprising a third organic layer and a third aqueous layer, wherein the third organic layer comprises Compound (I); extracting the third aqueous layer using a third organic solvent; and concentrating the third organic layer. In some embodiments, the methods further comprise the step of adding an antisolvent to the third organic layer to create a precipitate comprising Compound (I). In some embodiments, the methods further comprise the steps of: dissolving the precipitate comprising Compound (I) in a fourth organic solvent to create a fourth solution; and spray drying the fourth solution to obtain a solid form of Compound (I).

DEFINITIONS

Figure 1:
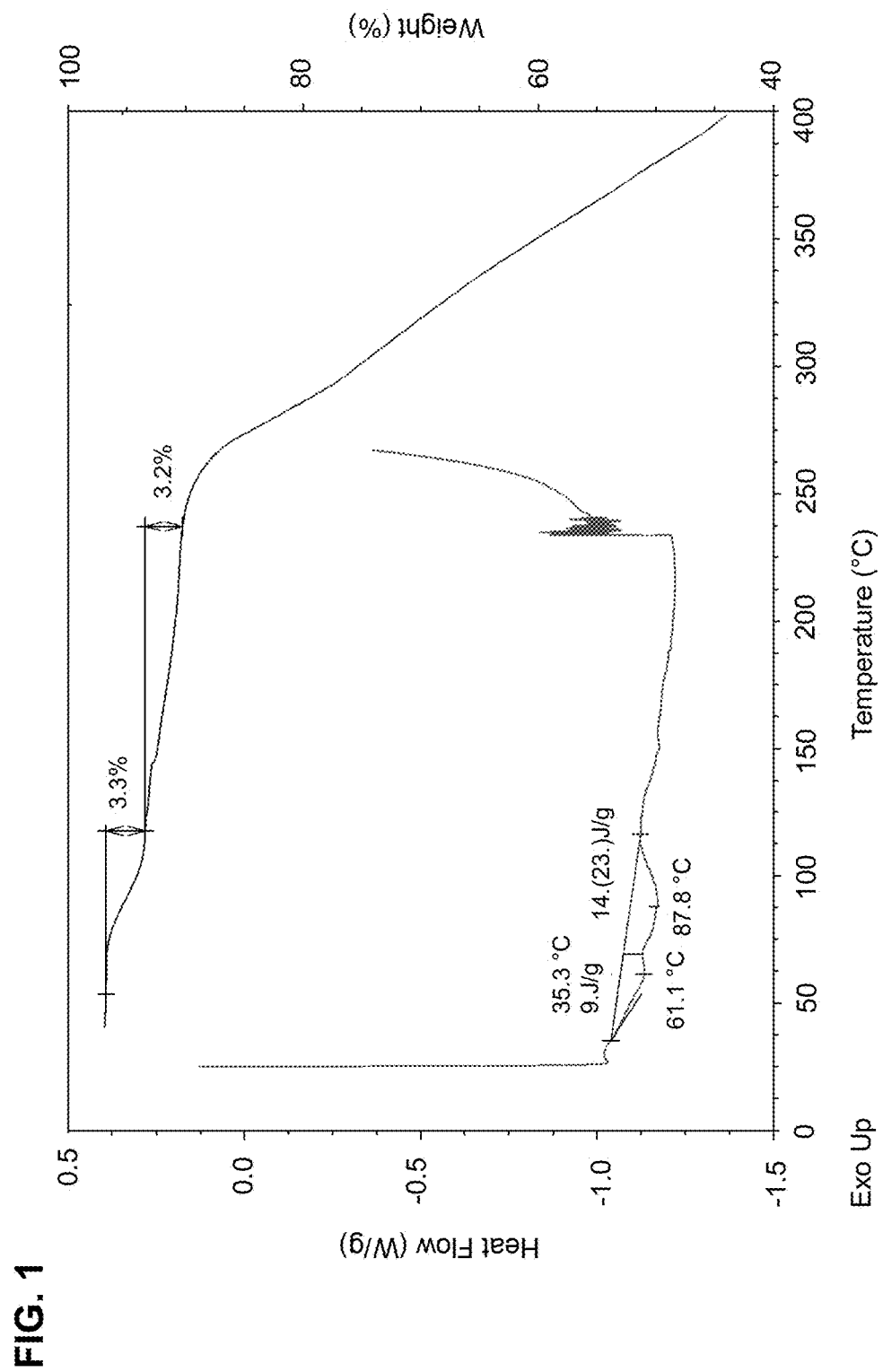
FIG. 1 depicts an example combined differential scanning calorimetry (DSC)-thermogravimetric analysis (TGA) plot for a solid form of Compound (I) prepared substantially in accordance with the process detailed in Step 1A in Example 1 of WO 2015/127310 (Comparator 1 herein).
Figure 2:
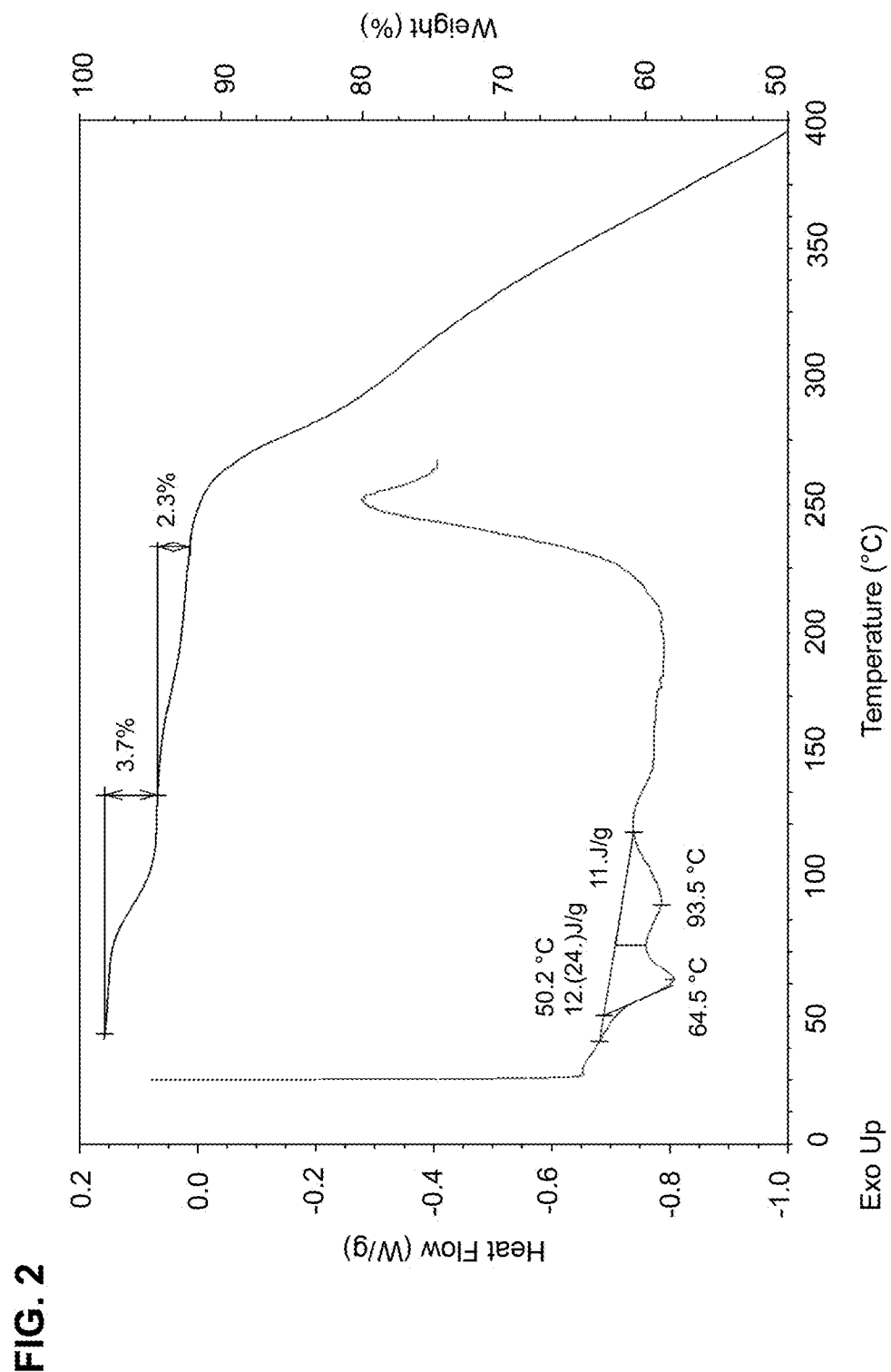
FIG. 2 depicts an example combined DSC-TGA plot for a solid form of Compound (I) prepared substantially in accordance with the process detailed in Example 31 of WO 2014/039899 (Comparator 2 herein).
Figure 3:
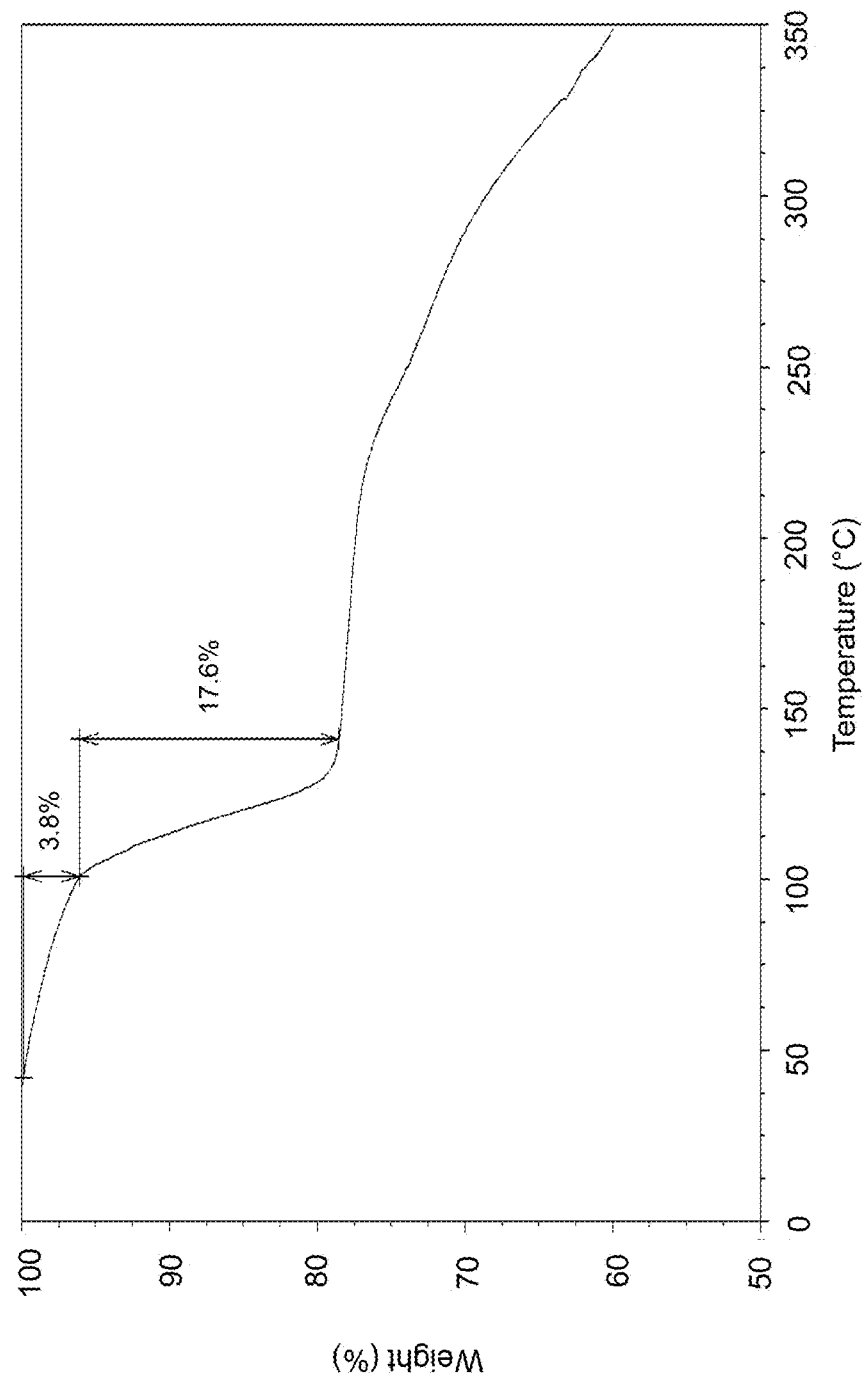
FIG. 3 depicts an example TGA thermal curve for a solid form of Compound (I) prepared substantially in accordance with the process detailed in Step 1 in Example 1 of WO 2015/127310 (Comparator 3 herein).
Figure 4:
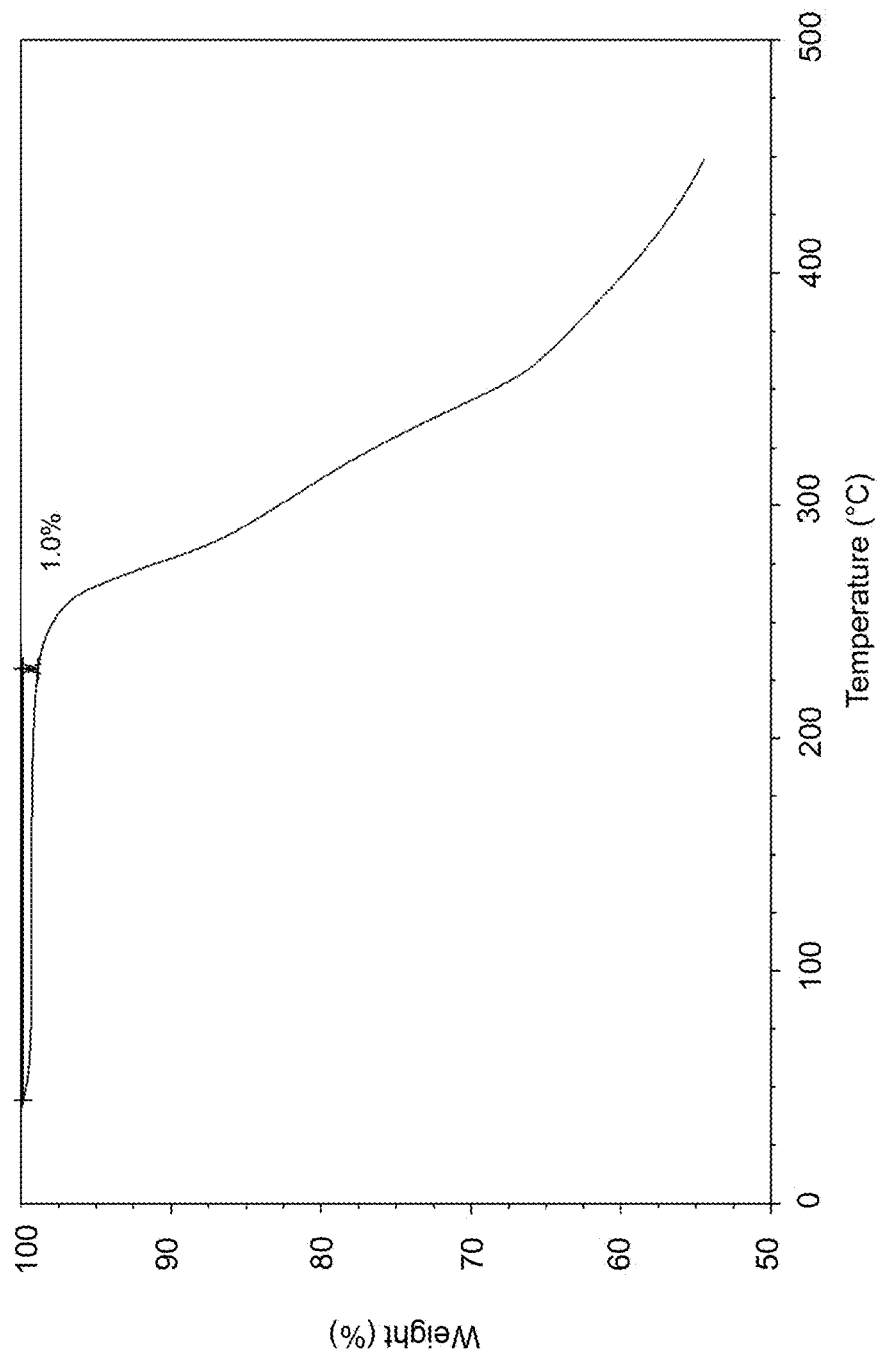
FIG. 4 depicts an example TGA thermal curve for a solid form of Compound (I) prepared by a precipitation process described herein (micronized).
Figure 5:
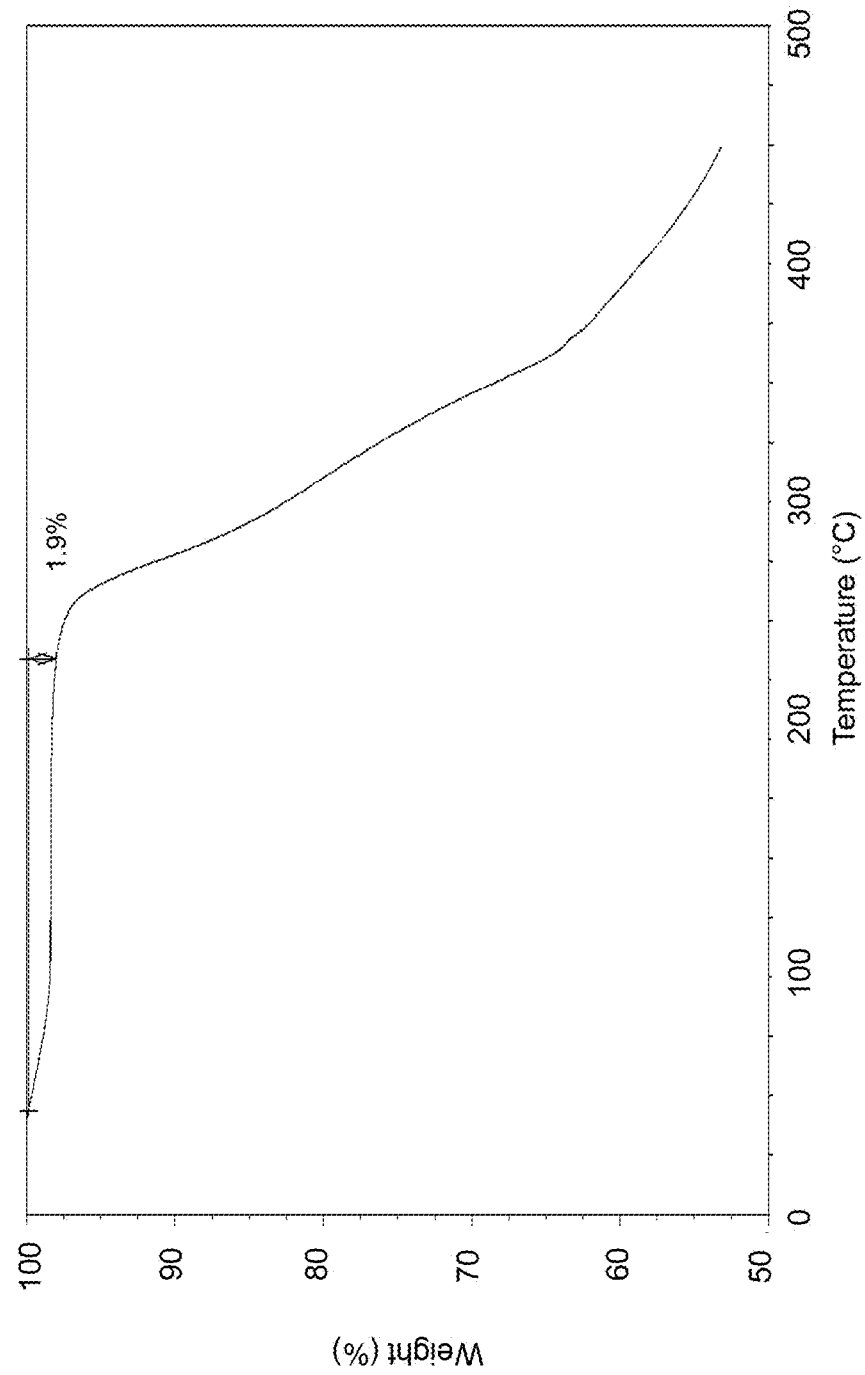
FIG. 5 depicts an example TGA thermal curve for a solid form of Compound (I) prepared by a precipitation process described herein (not micronized).
Figure 6:
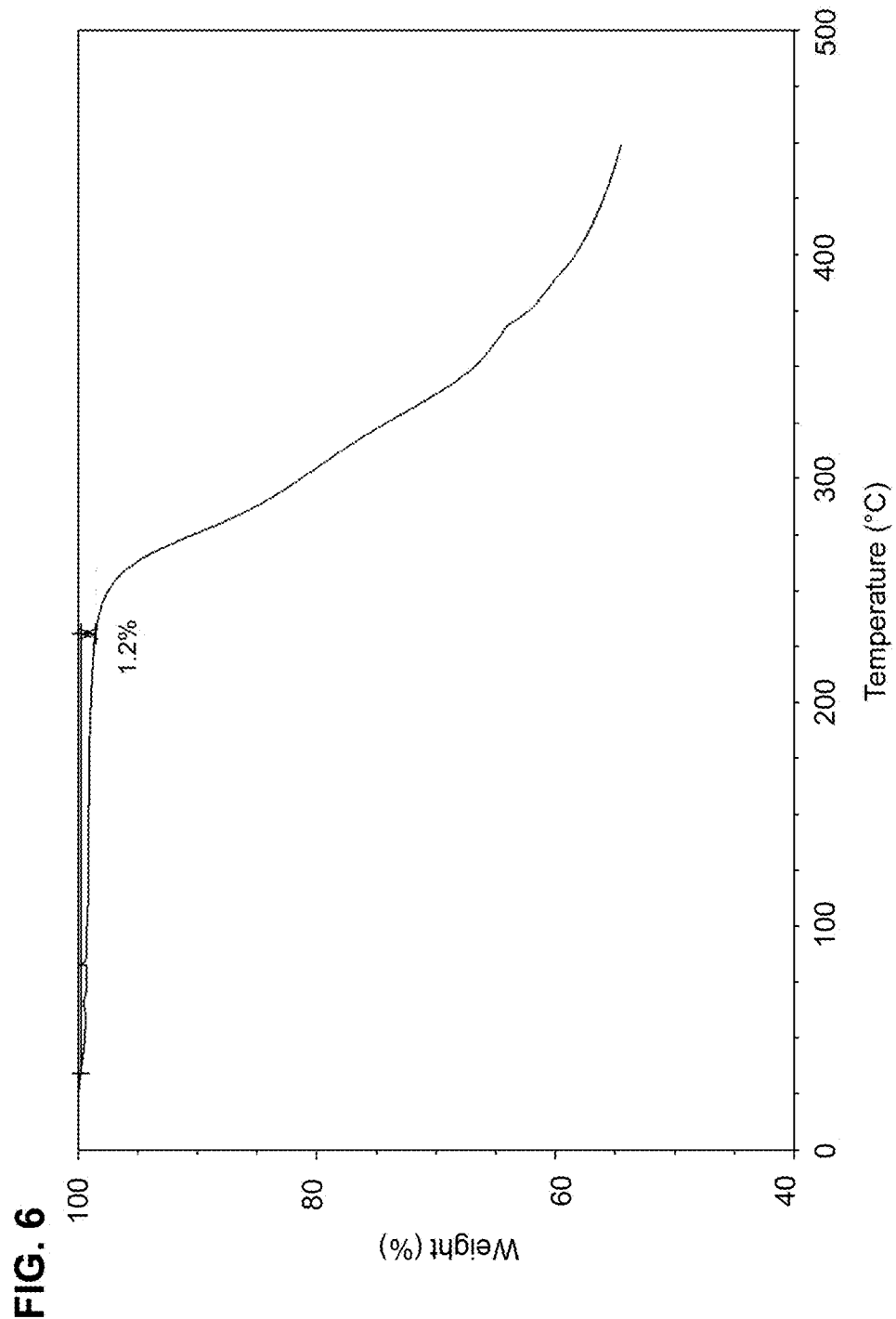
FIG. 6 depicts an example TGA thermal curve for a solid form of Compound (I) prepared by a spray drying process described herein.
Figure 7:
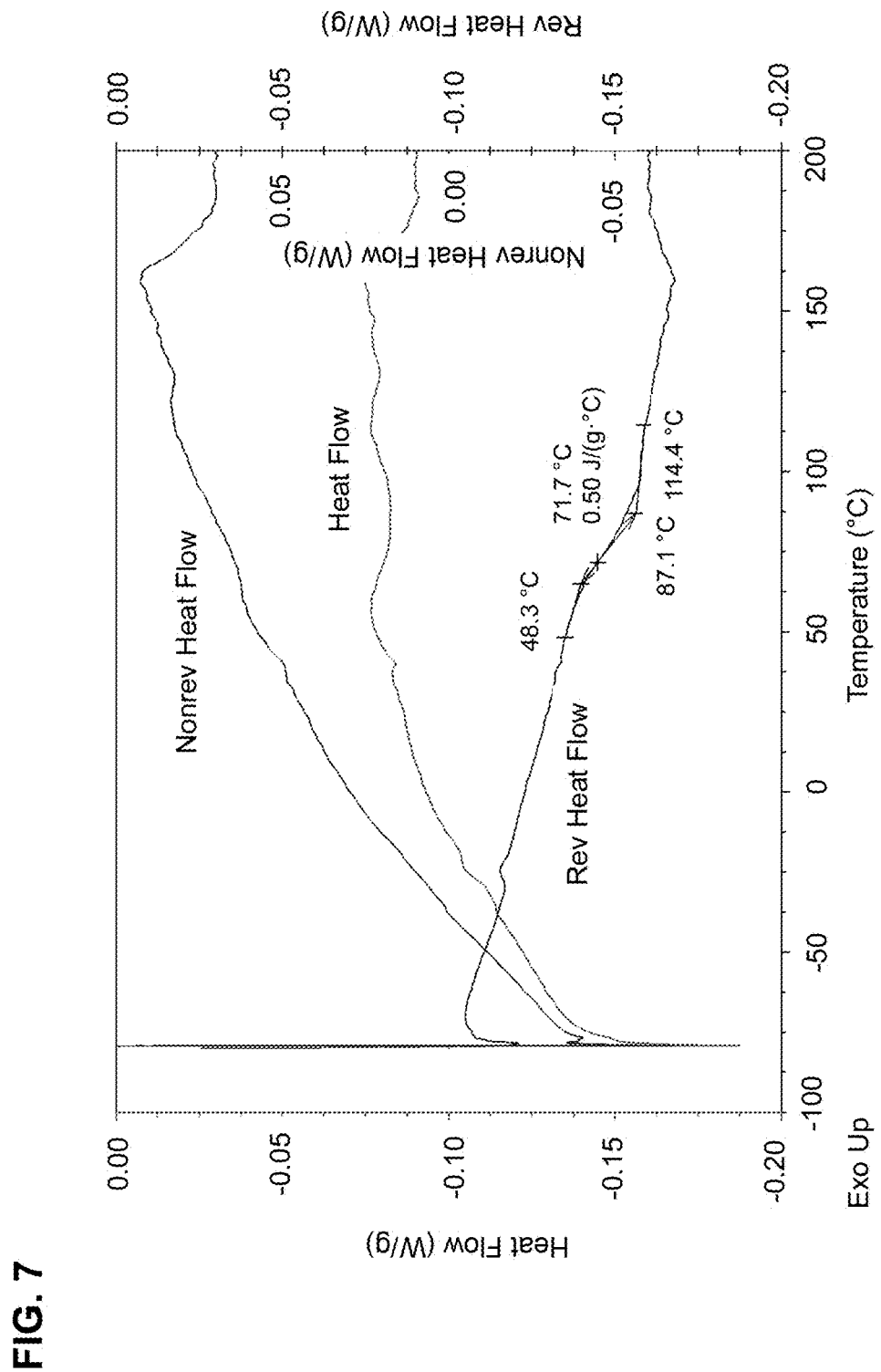
FIG. 7 depicts an example modulated DSC (mDSC) thermogram for a solid form of Compound (I) prepared substantially in accordance with the process detailed in Step 1A in Example 1 of WO 2015/127310 (Comparator 1 herein) at 0% relative humidity.
Figure 8:
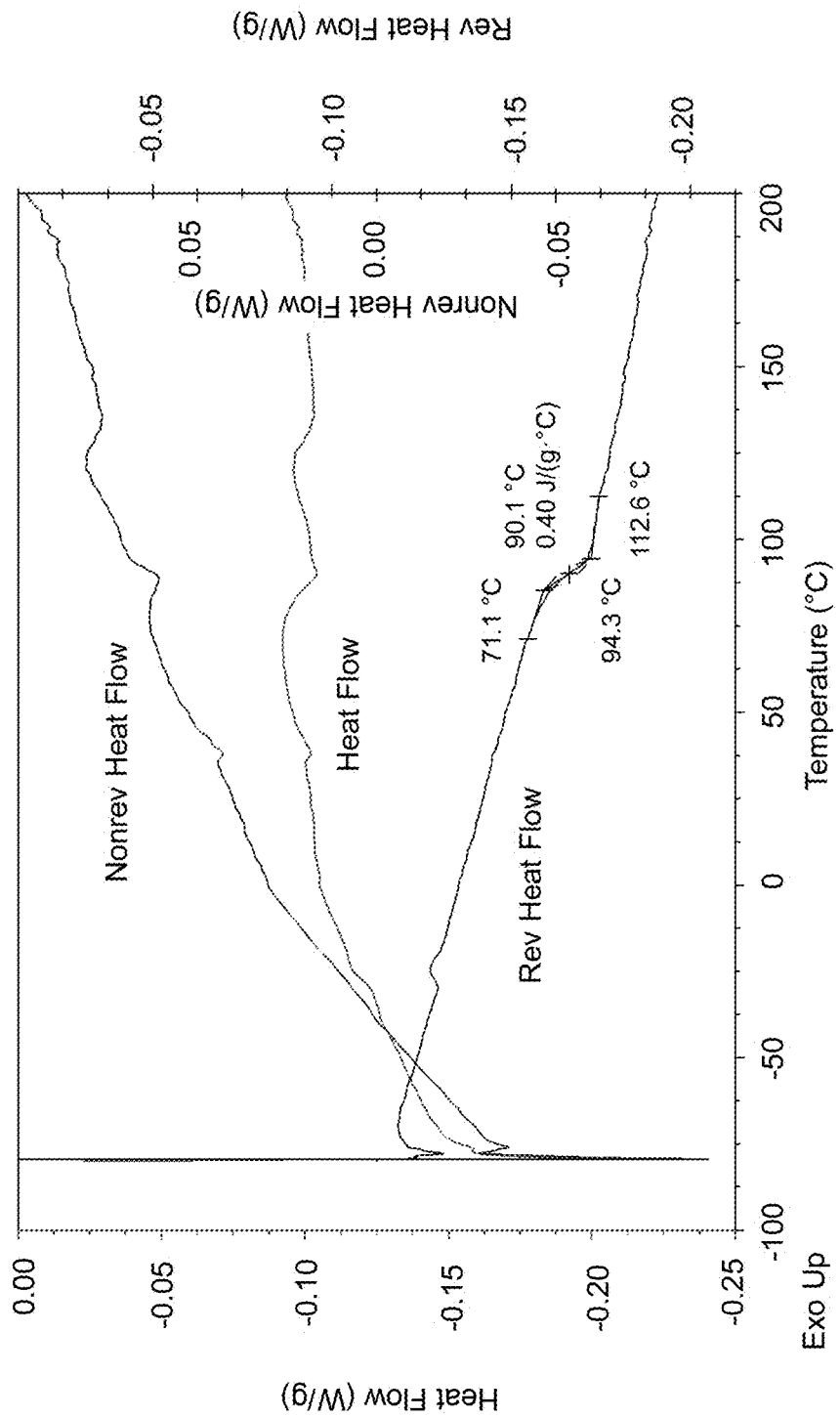
FIG. 8 depicts an example mDSC thermogram for a solid form of Compound (I) prepared substantially in accordance with the process detailed in Example 31 of WO 2014/039899 (Comparator 2 herein) at 0% relative humidity.
Figure 9:
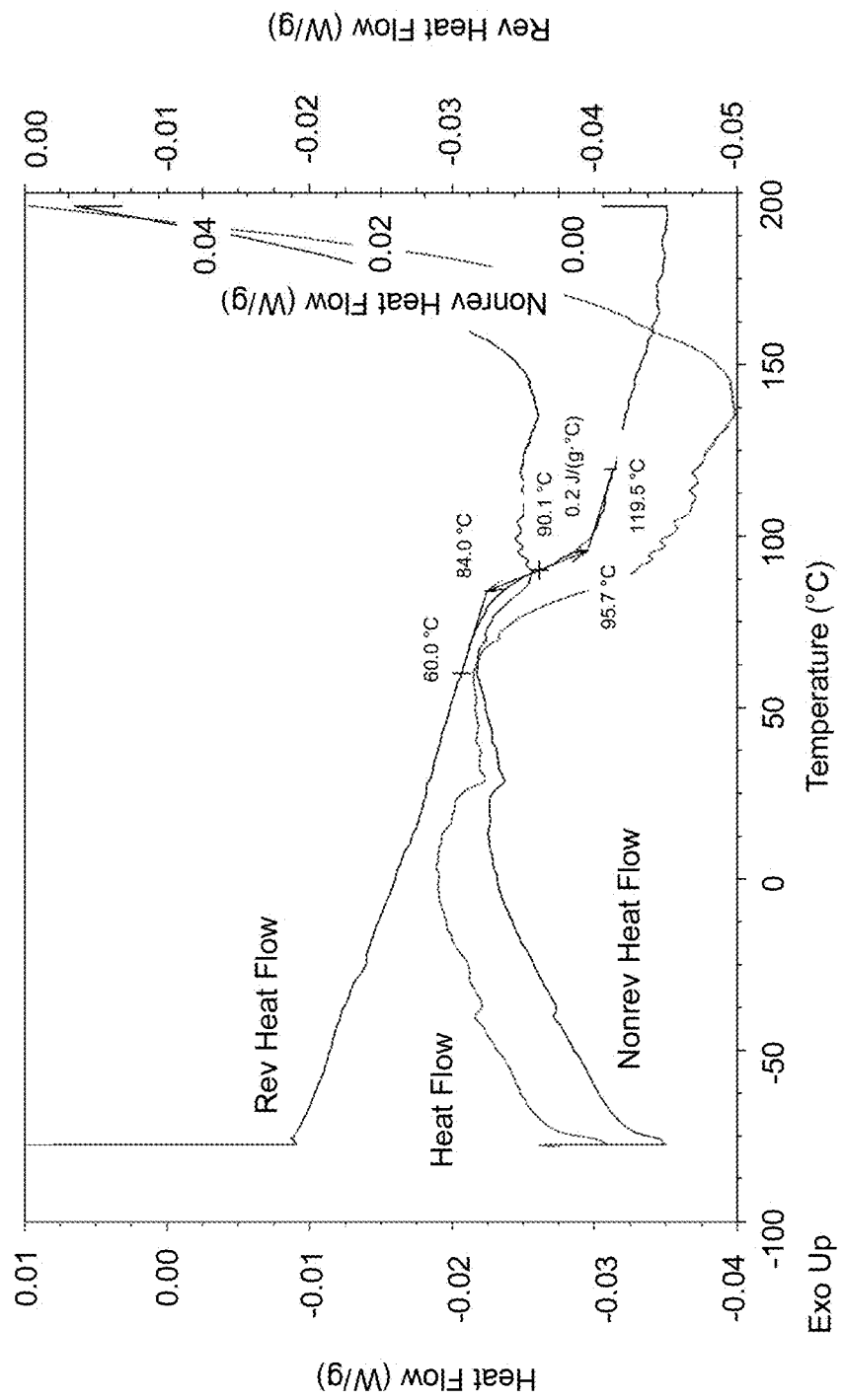
FIG. 9 depicts an example mDSC thermogram for a solid form of Compound (I) prepared substantially in accordance with the process detailed in Step 1 in Example 1 of WO 2015/127310 (Comparator 3 herein) at 0% relative humidity.
Figure 10:
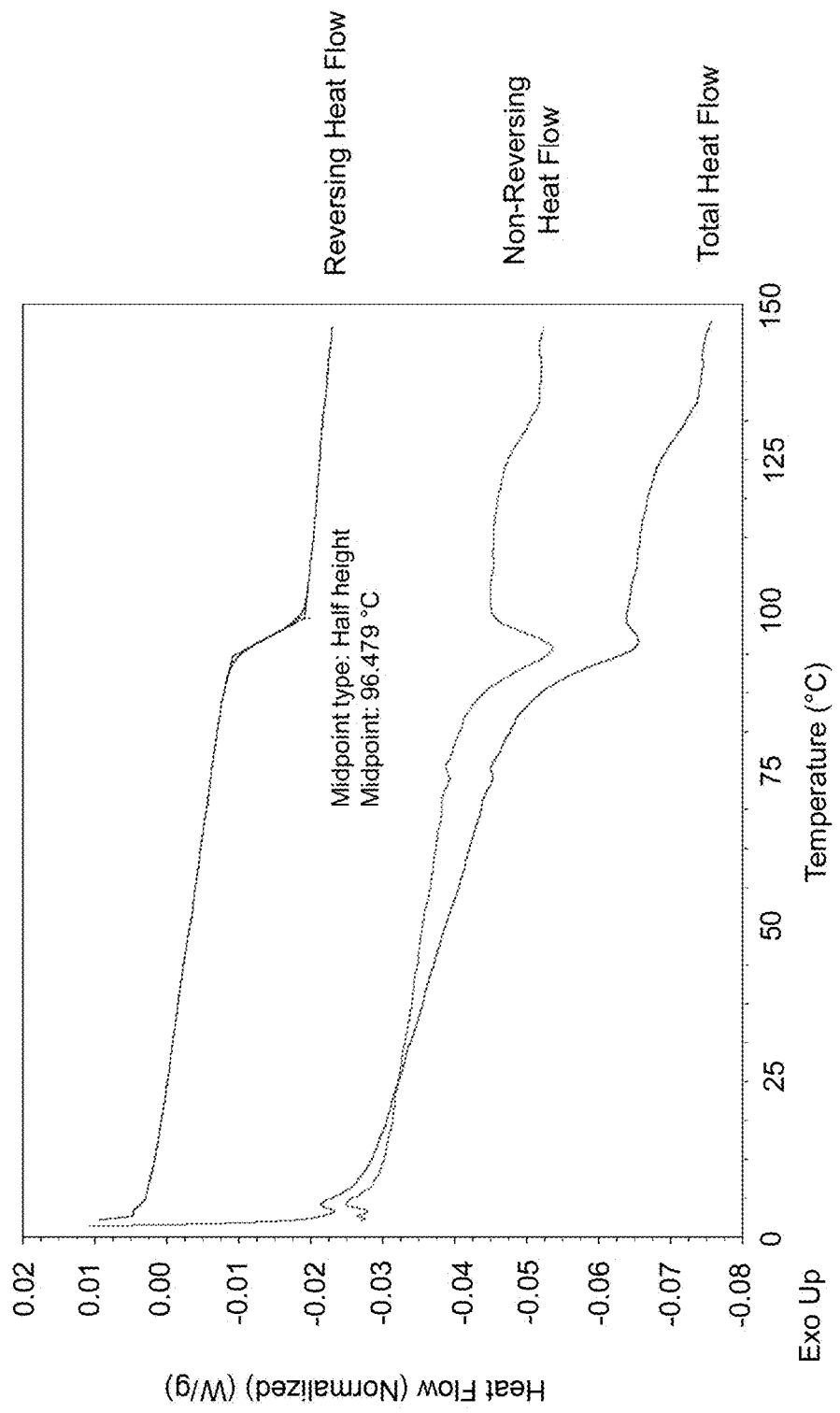
FIG. 10 depicts an example mDSC thermogram for a solid form of Compound (I) prepared by a precipitation process described herein (not micronized) at 0% relative humidity.
Figure 11:
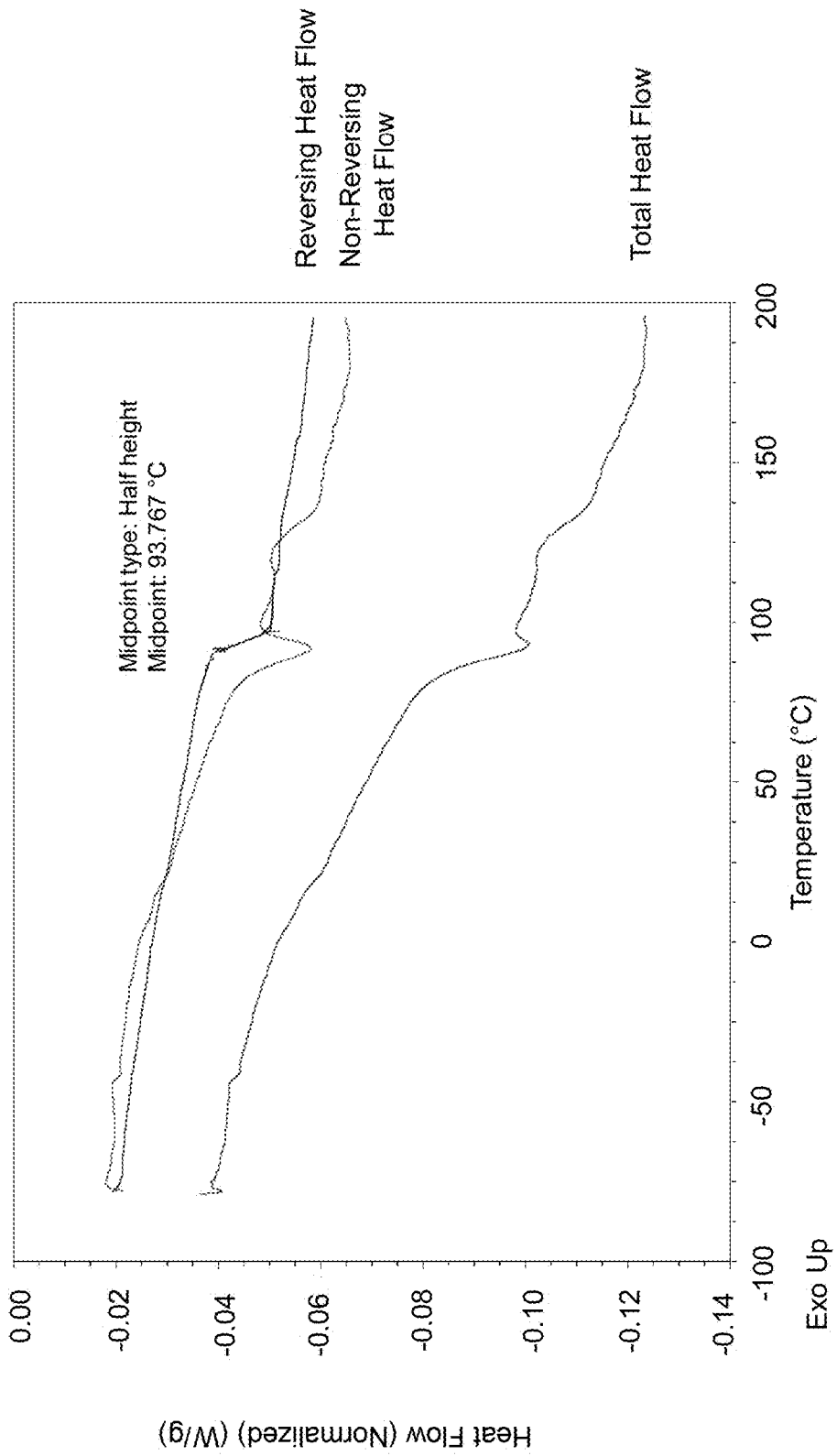
FIG. 11 depicts an example mDSC thermogram for a solid form of Compound (I) prepared by a spray drying process described herein at 0% relative humidity.

As used herein, "a" or "an" entity refers to one or more of that entity, e.g., "a compound" refers to one or more compounds or at least one compound unless stated otherwise. As such, the terms "a" (or "an"), "one or more", and "at least one" are used interchangeably herein.

As used herein, "Compound (I)" refers to the (E) isomer, (Z) isomer, or a mixture of (E) and (Z) isomers of (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, (S)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, or a mixture of (R) and (S) enantiomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, which has the following structure:

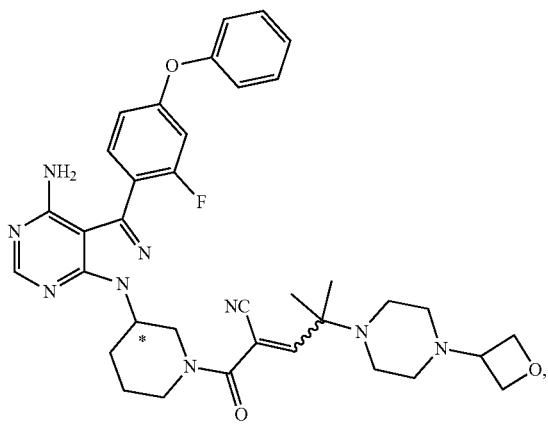 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

where *C is a stereochemical center.

When Compound (I) is denoted as (R)-2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, it may contain the corresponding (S) enantiomer as an impurity in less than 1% by weight. Accordingly, when the Compound (I) is denoted as a mixture of (R) and (S) enantiomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, the amount of (R) or (S) enantiomer in the mixture is greater than 1% by weight. Similarly, when Compound (I) is denoted as the (E) isomer, it may contain the corresponding (Z) isomer as an impurity in less than 1% by weight. Accordingly, when the Compound (I) is denoted as a mixture of (E) and (Z) isomers of 2-[3-[4-amino-3-(2-fluoro-4-phenoxy-phenyl)pyrazolo[3,4-d]pyrimidin-1-yl]piperidine-1-carbonyl]-4-methyl-4-[4-(oxetan-3-yl)piperazin-1-yl]pent-2-enenitrile, the amount of (E) or (Z) isomer in the mixture is greater than 1% by weight.

Herein, Compound (I) may be referred to as a "drug," "active agent," "a therapeutically active agent," or a "API."

As used herein, "substantially pure" in connection with a geometric isomeric form refers to a compound, such as Compound (I), wherein more than 70% by weight of the compound is present as the given isomeric form. For example, the phrase "the solid form of Compound (I) is a substantially pure (E) isomer of Compound (I)" refers to the solid form of Compound (I) having at least 70% by weight of the solid form of Compound (I) being in the (E) isomeric form, and the phrase "the solid form of Compound (I) is a substantially pure (Z) isomer of Compound (I)" refers to the solid form of Compound (I) having at least 70% by weight of the solid form of Compound (I) being in the (Z) isomeric form. In some embodiments, at least 80% by weight of the solid form of Compound (I) is the (E) form or at least 80% by weight of the solid form of Compound (I) is the (Z) form. In some embodiments, at least 85% by weight of the solid form of Compound (I) is in the (E) form or at least 85% by weight of the solid form of Compound (I) is in the (Z) form. In some embodiments, at least 90% by weight of the solid form of Compound (I) is in the (E) form or at least 90% by weight of the solid form of Compound (I) is in the (Z) form. In some embodiments, at least 95% by weight of the solid form of Compound (I) is in the (E) form or at least 95% by weight of the solid form of Compound (I) is in the (Z) form. In some embodiments, at least 97% by weight, or 98% by weight, of the solid form of Compound (I) is in the (E) form or at least 97% by weight, or 98% by weight, of the solid form of Compound (I) is in the (Z) form. In some embodiments, at least 99% by weight of the solid form of Compound (I) is in the (E) form or at least 99% by weight of the solid form of Compound (I) is in the (Z) form. The relative amounts of (E) and (Z) isomers in a solid mixture can be determined according to standard methods and techniques known in the art.

As used herein, "substantially pure" in connection with a solid form of a compound, such as Compound (I), refers to a solid form wherein more than 70% by weight of the solid form is the compound. For example, the phrase "the solid form of Compound (I) is substantially pure" refers to the solid form of Compound (I) being at least 70% by weight Compound (I).

As used herein, "substantially free of," in connection with a component in a solid form, such as a degradation product (e.g., dimers of Compound (I)), means that less than 5% by weight of the solid form comprises the component. Relative amounts of components in a solid form can be determined according to standard methods and techniques known in the art. As used herein, the term "pharmaceutically acceptable salt" refers to a non-toxic salt form of a compound of this disclosure. Pharmaceutically acceptable salts of Compound (I) of this disclosure include those derived from suitable inorganic and organic acids and bases. Pharmaceutically acceptable salts are well known in the art. Suitable pharmaceutically acceptable salts are, e.g., those disclosed in Berge, S. M., et al. J. Pharma. Sci. 66:1-19 (1977). Non-limiting examples of pharmaceutically acceptable salts disclosed in that article include: acetate; benzenesulfonate; benzoate; bicarbonate; bitartrate; bromide; calcium edetate; camsylate; carbonate; chloride; citrate; dihydrochloride; edetate; edisylate; estolate; esylate; fumarate; gluceptate; gluconate; glutamate; glycollylarsanilate; hexylresorcinate; hydrabamine; hydrobromide; hydrochloride; hydroxynaphthoate; iodide; isethionate; lactate; lactobionate; malate; maleate; mandelate; mesylate; methylbromide; methylnitrate; methylsulfate; mucate; napsylate; nitrate; pamoate (embonate); pantothenate; phosphate/diphosphate; polygalacturonate; salicylate; stearate; subacetate; succinate; sulfate; tannate; tartrate; teociate; triethiodide; benzathine; chloroprocaine;

choline; diethanolamine; ethylenediamine; meglumine; procaine; aluminum; calcium; lithium; magnesium; potassium; sodium; and zinc.

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Additional non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Non-limiting examples of pharmaceutically acceptable salts derived from appropriate bases include alkali metal, alkaline earth metal, ammonium, and $N^+(C_{1-4}$ alkyl$)_4$ salts. This disclosure also envisions the quaternization of any basic nitrogen-containing groups of the compounds disclosed herein. Non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other non-limiting examples of pharmaceutically acceptable salts include besylate and glucosamine salts.

As used herein, a "pharmaceutically acceptable excipient" refers to a carrier or an excipient that is useful in preparing a pharmaceutical composition. For example, a pharmaceutically acceptable excipient is generally safe and includes carriers and excipients that are generally considered acceptable for mammalian pharmaceutical use.

As used herein, the term "ambient conditions" refers to room temperature, open air, and uncontrolled humidity conditions. As used herein, the term "room temperature" or "ambient temperature" means a temperature between 15° C. and 30° C.

As used herein, the term "inhibit," "inhibition," or 'inhibiting" refers to the reduction or suppression of a given condition, symptom, or disorder, or disease, or a significant decrease in the baseline activity of a biological activity or process.

As used herein, the term "treat," "treating," or "treatment," when used in connection with a disorder or condition, includes any effect, e.g., lessening, reducing, modulating, ameliorating, or eliminating, that results in the improvement of the disorder or condition. Improvements in or lessening the severity of any symptom of the disorder or condition can be readily assessed according to standard methods and techniques known in the art.

As used herein, a "mammal" refers to domesticated animals (e.g., dogs, cats, and horses) and humans. In some embodiments, the mammal is a human.

As used herein, "cc" or "cm$^3$" refers to cubic centimeters.

As used herein, "residual solvent" refers to an organic volatile chemical used or produced in the manufacture of drug substances or excipients, or in the preparation of drug products. Residual solvents are not completely removed during the manufacturing process.

As used herein, the term "level" in the phrase "total level of residual solvents" refers to a level determined by gas chromatography.

As used herein, residual solvent classes correspond to those defined in the International Conference on Harmonization of Technical Requirements for Registration of Pharmaceuticals for Human Use ("ICH") guidelines. The ICH guidelines categorize residual solvents in three classes: class 1; class 2; and class 3.

As used herein, "class 1 solvents" refer to solvents to be avoided according to ICH guidelines. Class 1 solvents include known human carcinogens, strongly suspected human carcinogens, and environmental hazards, including, but not limited to, benzene, carbon tetrachloride, 1,2-dichloroethane, and 111-tetrachloroethane As used herein, "class 2 solvents" refer to solvents to be limited according to ICH guidelines. Class 2 solvents include non-genotoxic animal carcinogens or possible causative agents of other irreversible toxicity, such as neurotoxicity or teratogenicity, and solvents suspected of other significant but reversible toxicities. Class 2 solvents include, but are not limited to, the following solvents: acetonitrile; chlorobenzene; chloroform; cumene; cyclohexane; 1,2-dichloroethane; dichloromethane; 1,2-dimethoxyethane; N,N-dimethylacetamide; N,N-dimethylformamide; 1,4-dioxane, 2-ethoxyethanol; ethyleneglycol; formamide; hexane; methanol; 2-methoxyethanol; methylbutyl ketone; methylcyclohexane; methylisobutylkeone; and N-methylpyrrolidone.

As used herein, "class 3 solvents" refer to solvents with low toxic potential to man according to ICH guidelines. For class 3 solvents, no health-based exposure limit is required under ICH guidelines. Class 3 solvents have permitted daily exposures (PDEs) of 50 mg or more per day. Based on ICH guidelines, class 3 residual solvent levels of 50 mg per day or less (corresponding to 5000 ppm or 0.5%) are acceptable without justification. Class 3 solvents include, but are not limited to, the following solvents: acetic acid; acetone, anisole; 1-butanol; 2-butanol; butyl acetate; tert-butylmethyl ether; dimethyl sulfoxide; ethanol; ethyl acetate; ethyl ether; ethyl formate; formic acid; heptane; isobutyl acetate; isopropyl acetate; methyl acetate; 3-methyl-1-butanol; methylethyl ketone; 2-methyl-1-propanol; pentane; 1-pentanol; 1-propanol; 2-propanol; propyl acetate; and trimethylamine.

As used herein, the term "antisolvent" refers to any liquid in which the product is insoluble or at maximum sparingly soluble (solubility of product<0.01 mol/L).

As used herein, the term "antisolvent precipitation" refers to a process wherein supersaturation is achieved and, as a result, precipitation is induced by the addition of an antisolvent to the product solution.

As used herein, the term "organic layer" refers to a layer that is insoluble in water and contains at least one organic solvent that is not miscible in water.

As used herein, the term "aqueous layer" refers to a layer that contains water.

As used herein, the term "solid form" refers to a physical form of a compound that is not predominantly in a liquid or gaseous state, including amorphous and crystalline forms.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. For example, an amorphous material is a solid material having no sharp characteristic signal(s) in its X-ray power diffractogram (i.e., is not crystalline as determined by XRPD). Instead, one or more broad peaks (e.g., halos) appear in its diffractogram. Broad peaks are characteristic of an amorphous solid. See, e.g., US 2004/0006237 for a comparison of diffractograms of an amorphous material and crystalline material.

As used herein, the term "substantially amorphous" refers to a solid material having little or no long-range order in the position of its molecules. For example, substantially amorphous materials have less than 15% crystallinity (e.g., less than 10% crystallinity or less than 5% crystallinity). "Substantially amorphous" includes the descriptor "amorphous," which refers to materials having no (0%) crystallinity.

As used herein, the term "DSC" refers to the analytical method of differential scanning calorimetry.

As used herein, the term "TGA" refers to the analytical method of thermo gravimetric (also referred to as thermogravimetric) analysis.

As used herein, particle sizes are expressed in terms of particle size distribution (e.g., $D_{10}$, $D_{50}$, and $D_{90}$ values). Particle size distribution may be affected by the hydration state of the particles. Illustratively, a wet particle size distribution may differ from a dry particle size distribution and corresponding possess different characteristic $D_{10}$, $D_{50}$, and $D_{90}$ values.

As would be understood by a person having ordinary skill in the art, particle sizes and particle size distributions of powders can be measured using various techniques known in the art, such as laser diffraction. In some embodiments, particle size distributions of solid forms of Compound (I) are expressed using values (e.g., $D_{10}$, $D_{50}$, and $D_{90}$ values) measured by laser diffraction.

As used herein, "$D_{50}$" refers to the median diameter of a particle size distribution.

As used herein, "$D_{10}$" refers to the particle diameter at which 10% of a population of particles possess a particle diameter of $D_{10}$ or less.

As used herein, "$D_{90}$" refers to the particle diameter at which 90% of a population of particles possess a particle diameter of $D_{90}$ or less.

As used herein, "bulk density" refers the mass of particles of material divided by the total volume the particles occupy. The total volume includes particle volume, inter-particle void volume, and internal pore volume. Bulk density is not an intrinsic property of a material and may vary based on how the material is processed.

As used herein, "tapped density" is the mass of particles of material divided by the total volume the particles occupy after mechanically tapping a container containing the particles. The total volume includes particle volume, inter-particle void volume, and internal pore volume. Tapped density is not an intrinsic property of a material and may vary based on how the material is processed.

As used herein, "Hausner ratio" refers to a number correlated to the flowability of a powder or granular material. The Hausner ratio is the ratio of the bulk density of the material to the tapped density of the material.

EMBODIMENTS

Without limitation, some embodiments of the disclosure include:

1. A solid form of Compound (I)

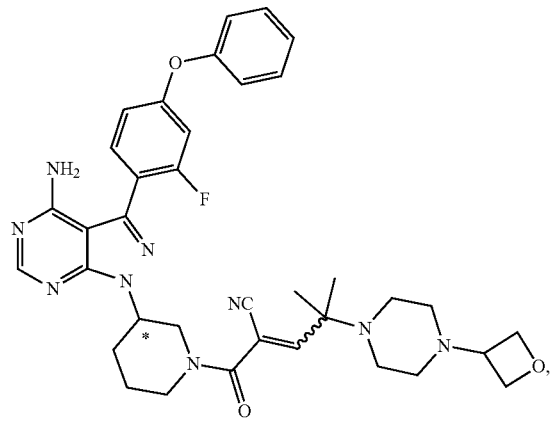 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

characterized by a mean bulk density greater than 0.3 g/cc.

2. The solid form according to embodiment 1, characterized by a mean bulk density greater than 0.4 g/cc.

3. The solid form according to embodiment 1 or 2, characterized by a mean bulk density greater than 0.5 g/cc.

4. The solid form according to any one of embodiments 1 to 3, characterized by a mean bulk density greater than 0.6 g/cc.

5. The solid form according to any one of embodiments 1 to 4, characterized by a mean bulk density between 0.6 g/cc and 0.7 g/cc.

6. The solid form according to any one of embodiments 1 to 5, characterized by a mean tapped density greater than 0.5 g/cc.

7. The solid form according to any one of embodiments 1 to 6, characterized by a mean tapped density greater than 0.7 g/cc.

8. The solid form according to any one of embodiments 1 to 7, characterized by a mean tapped density greater than 0.8 g/cc.

9. The solid form according to any one of embodiments 1 to 7, characterized by a mean tapped density between 0.7 g/cc and 0.9 g/cc.

10. The solid form according to any one of embodiments 1 to 9, characterized by a Hausner ratio less than or equal to 1.2.

11. The solid form according to any one of embodiments 1 to 10, characterized by a wet particle size distribution having a $D_{10}$ value greater than 70 μm.

12. The solid form according to any one of embodiments 1 to 11, characterized by a wet particle size distribution having a $D_{50}$ value greater than 200 μm.

13. The solid form according to any one of embodiments 1 to 12, characterized by a wet particle size distribution having a $D_{90}$ value greater than 400 μm.

14. The solid form according to any one of embodiments 1 to 13, characterized by a mass loss of less than 5 wt. % between 20° C. and 240° C. by thermogravimetric analysis.

15. The solid form according to any one of embodiments 1 to 14, characterized by a mass loss of less than 3 wt. % between 20° C. and 240° C. by thermogravimetric analysis.

16. The solid form according to any one of embodiments 1 to 15, characterized by mass loss of less than 2 wt. % between 20° C. and 240° C. by thermogravimetric analysis.
17. The solid form according to any one of embodiments 1 to 16, characterized by mass loss of less than 1.5 wt. % between 20° C. and 240° C. by thermogravimetric analysis.
18. The solid form according to any one of embodiments 1 to 17, wherein the total level of residual solvents in the solid form is less than 1%.
19. The solid form according to any one of embodiments 1 to 18, wherein the total level of residual solvents in the solid form is less than 0.5%.
20. The solid form according to any one of embodiments 1 to 19, characterized by a glass transition temperature ($T_g$) greater than 90° C. at 0% relative humidity.
21. The solid form according to any one of embodiments 1 to 20, wherein:
    the residual methanol level is less than 3000 ppm;
    the residual isopropyl acetate level is less than 5000 ppm; and/or
    the residual heptane level is less than 5000 ppm.
22. The solid form according to any one of embodiments 1 to 21, wherein:
    the residual methanol level is less than 500 ppm;
    the residual isopropyl acetate level is less than 4000 ppm; and/or
    the residual heptane level is less than 500 ppm.
23. The solid form according to any one of embodiments 1 to 22, wherein the residual dichloromethane level is less than 1500 ppm.
24. The solid form according to any one of embodiments 1 to 23, wherein the residual dichloromethane level is less than 1000 ppm.
25. The solid form according to any one of embodiments 1 to 24, wherein the residual dichloromethane level is less than 500 ppm.
26. The solid form according to any one of embodiments 1 to 25, wherein the residual dichloromethane level is less than 100 ppm.
27. The solid form according to any one of embodiments 1 to 23, wherein there is no detectable residual solvent in the solid form.
28. The solid form according to any one of embodiments 1 to 27, wherein the solid form is substantially amorphous.
29. A solid form of Compound (I)

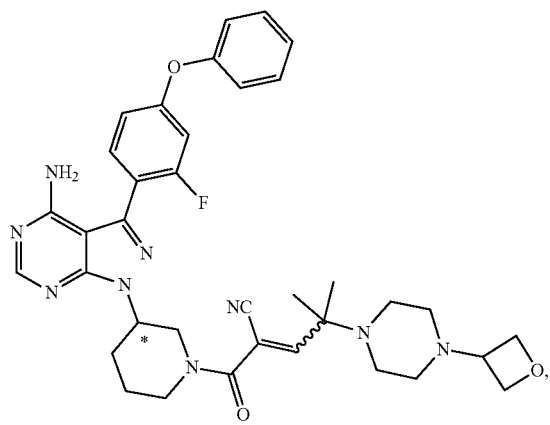 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

characterized by a mean tapped density greater than 0.5 g/cc.

30. The solid form according to embodiment 29, characterized by a mean tapped density greater than 0.6 g/cc.
31. The solid form according to embodiment 29 or 30, characterized by a mean tapped density greater than 0.7 g/cc.
32. The solid form according to any one of embodiments 29 to 31, characterized by a mean tapped density greater than 0.8 g/cc.
33. The solid form according to any one of embodiments 29 to 32, characterized by a mean tapped density between 0.7 g/cc and 0.9 g/cc.
34. The solid form according to any one of embodiments 29 to 33, characterized by a Hausner ratio less than or equal to 1.2.
35. The solid form according to any one of embodiments 29 to 34, characterized by a wet particle size distribution having a $D_{10}$ value greater than 70 μm.
36. The solid form according to any one of embodiments 29 to 35, characterized by a wet particle size distribution having a $D_{50}$ value greater than 200 μm.
37. The solid form according to any one of embodiments 29 to 36, characterized by a wet particle size distribution having a $D_{90}$ value greater than 400 μm.
38. The solid form according to any one of embodiments 29 to 37, characterized by a mass loss of less than 5 wt. % between 20° C. and 240° C. by thermogravimetric analysis.
39. The solid form according to any one of embodiments 29 to 38, characterized by a mass loss of less than 3 wt. % between 20° C. and 240° C. by thermogravimetric analysis.
40. The solid form according to any one of embodiments 29 to 39, characterized by mass loss of less than 2 wt. % between 20° C. and 240° C. by thermogravimetric analysis.
41. The solid form according to any one of embodiments 29 to 40, characterized by mass loss of less than 1.5 wt. % between 20° C. and 240° C. by thermogravimetric analysis.
42. The solid form according to any one of embodiments 29 to 41, wherein the total level of residual solvents in the solid form is less than 1%.
43. The solid form according to any one of embodiments 29 to 42, wherein the total level of residual solvents in the solid form is less than 0.5%.
44. The solid form according to any one of embodiments 29 to 43, characterized by a glass transition temperature ($T_g$) greater than 90° C. at 0% relative humidity.
45. The solid form according to any one of embodiments 29 to 44, wherein:
    the residual methanol level is less than 3000 ppm;
    the residual isopropyl acetate level is less than 5000 ppm; and/or
    the residual heptane level is less than 5000 ppm.
46. The solid form according to any one of embodiments 29 to 45, wherein:
    the residual methanol level is less than 500 ppm;
    the residual isopropyl acetate level is less than 4000 ppm; and/or
    the residual heptane level is less than 500 ppm.
47. The solid form according to any one of embodiments 29 to 46, wherein the residual dichloromethane level is less than 1500 ppm.
48. The solid form according to any one of embodiments 29 to 47, wherein the residual dichloromethane level is less than 1000 ppm.
49. The solid form according to any one of embodiments 29 to 48, wherein the residual dichloromethane level is less than 500 ppm.
50. The solid form according to any one of embodiments 29 to 49, wherein the residual dichloromethane level is less than 100 ppm.

51. The solid form according to any one of embodiments 29 to 50, wherein there is no detectable residual solvent in the solid form.
52. The solid form according to any one of embodiments 29 to 51, wherein the solid form is substantially amorphous.
53. A solid form of Compound (I)

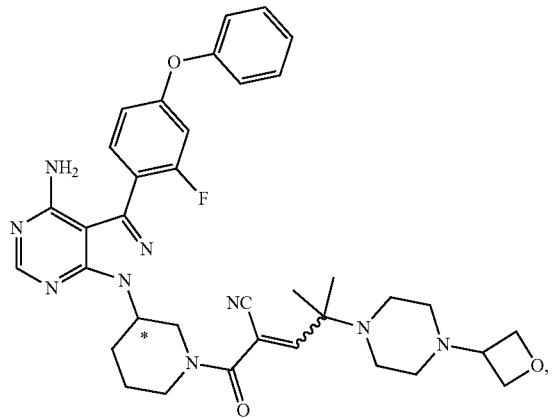 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

characterized by a Hausner ratio less than or equal to 1.2.
54. The solid form according to embodiment 53, characterized by a wet particle size distribution having a $D_{10}$ value greater than 70 μm.
55. The solid form according to embodiment 53 or 54, characterized by a wet particle size distribution having a $D_{50}$ value greater than 200 μm.
56. The solid form according to any one of embodiments 53 to 55, characterized by a wet particle size distribution having a $D_{90}$ value greater than 400 μm.
57. The solid form according to any one of embodiments 53 to 56, characterized by a mass loss of less than 5 wt. % between 20° C. and 240° C. by thermogravimetric analysis.
58. The solid form according to any one of embodiments 53 to 57, characterized by a mass loss of less than 3 wt. % between 20° C. and 240° C. by thermogravimetric analysis.
59. The solid form according to any one of embodiments 53 to 58, characterized by mass loss of less than 2 wt. % between 20° C. and 240° C. by thermogravimetric analysis.
60. The solid form according to any one of embodiments 53 to 59, characterized by mass loss of less than 1.5 wt. % between 20° C. and 240° C. by thermogravimetric analysis.
61. The solid form according to any one of embodiments 53 to 60, wherein the total level of residual solvents in the solid form is less than 1%.
62. The solid form according to any one of embodiments 53 to 61, wherein the total level of residual solvents in the solid form is less than 0.5%.
63. The solid form according to any one of embodiments 53 to 62, characterized by a glass transition temperature ($T_g$) greater than 90° C. at 0% relative humidity.
64. The solid form according to any one of embodiments 53 to 63, wherein:
the residual methanol level is less than 3000 ppm;
the residual isopropyl acetate level is less than 5000 ppm; and/or
the residual heptane level is less than 5000 ppm.
65. The solid form according to any one of embodiments 53 to 64, wherein:
the residual methanol level is less than 500 ppm;
the residual isopropyl acetate level is less than 4000 ppm; and/or
the residual heptane level is less than 500 ppm.
66. The solid form according to any one of embodiments 53 to 65, wherein the residual dichloromethane level is less than 1500 ppm.
67. The solid form according to any one of embodiments 53 to 66, wherein the residual dichloromethane level is less than 1000 ppm.
68. The solid form according to any one of embodiments 53 to 67, wherein the residual dichloromethane level is less than 500 ppm.
69. The solid form according to any one of embodiments 53 to 68, wherein the residual dichloromethane level is less than 100 ppm.
70. The solid form according to any one of embodiments 53 to 69, wherein there is no detectable residual solvent in the solid form.
71. The solid form according to any one of embodiments 53 to 70, wherein the solid form is substantially amorphous.
72. A solid form of Compound (I)

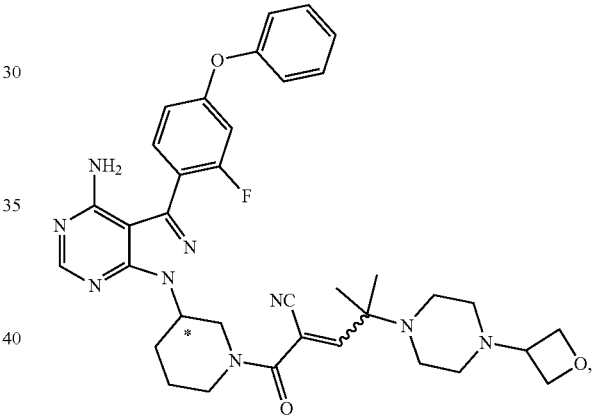

characterized by a wet particle size distribution having a $D_{10}$ value greater than 70 μm.
73. The solid form according to embodiment 72, characterized by a wet particle size distribution having a $D_{50}$ value greater than 200 μm.
74. The solid form according to embodiment 72 or 73, characterized by a wet particle size distribution having a $D_{90}$ value greater than 400 μm.
75. The solid form according to any one of embodiments 72 to 74, characterized by a mass loss of less than 5 wt. % between 20° C. and 240° C. by thermogravimetric analysis.
76. The solid form according to any one of embodiments 72 to 75, characterized by a mass loss of less than 3 wt. % between 20° C. and 240° C. by thermogravimetric analysis.
77. The solid form according to any one of embodiments 72 to 76, characterized by mass loss of less than 2 wt. % between 20° C. and 240° C. by thermogravimetric analysis.
78. The solid form according to any one of embodiments 72 to 77, characterized by mass loss of less than 1.5 wt. % between 20° C. and 240° C. by thermogravimetric analysis.
79. The solid form according to any one of embodiments 72 to 78, wherein the total level of residual solvents in the solid form is less than 1%.

80. The solid form according to any one of embodiments 72 to 79, wherein the total level of residual solvents in the solid form is less than 0.5%.

81. The solid form according to any one of embodiments 72 to 80, characterized by a glass transition temperature ($T_g$) greater than 90° C. at 0% relative humidity.

82. The solid form according to any one of embodiments 72 to 81, wherein:
the residual methanol level is less than 3000 ppm;
the residual isopropyl acetate level is less than 5000 ppm; and/or
the residual heptane level is less than 5000 ppm.

83. The solid form according to any one of embodiments 72 to 82, wherein:
the residual methanol level is less than 500 ppm;
the residual isopropyl acetate level is less than 4000 ppm; and/or
the residual heptane level is less than 500 ppm.

84. The solid form according to any one of embodiments 72 to 83, wherein the residual dichloromethane level is less than 1500 ppm.

85. The solid form according to any one of embodiments 72 to 84, wherein the residual dichloromethane level is less than 1000 ppm.

86. The solid form according to any one of embodiments 72 to 85, wherein the residual dichloromethane level is less than 500 ppm.

87. The solid form according to any one of embodiments 72 to 86, wherein the residual dichloromethane level is less than 100 ppm.

88. The solid form according to any one of embodiments 72 to 87, wherein there is no detectable residual solvent in the solid form.

89. The solid form according to any one of embodiments 72 to 88, wherein the solid form is substantially amorphous.

90. A solid form of Compound (I)

characterized by a wet particle size distribution having a $D_{10}$ value less than 10 μm.

91. The solid form according to embodiment 90, characterized by a wet particle size distribution having a $D_{10}$ value between 5 μm and 6 μm or a $D_{10}$ value between 1 and 2 μm.

92. The solid form according to embodiment 90 or 91, characterized by a wet particle size distribution having a $D_{50}$ value less than 100 μm.

93. The solid form according to any one of embodiments 90 to 92, characterized by a wet particle size distribution having a $D_{90}$ value less than 200 μm.

94. The solid form according to any one of embodiments 90 to 93, characterized by a mean bulk density less than 0.3 g/cc.

95. The solid form according to any one of embodiments 90 to 94, characterized by a mean tapped density less than 0.3 g/cc.

96. The solid form according to any one of embodiments 90 to 95, characterized by a mass loss of less than 5 wt. % between 20° C. and 240° C. by thermogravimetric analysis.

97. The solid form according to any one of embodiments 90 to 96, characterized by a mass loss of less than 3 wt. % between 20° C. and 240° C. by thermogravimetric analysis.

98. The solid form according to any one of embodiments 90 to 97, characterized by mass loss of less than 2 wt. % between 20° C. and 240° C. by thermogravimetric analysis.

99. The solid form according to any one of embodiments 90 to 98, characterized by mass loss of less than 1.5 wt. % between 20° C. and 240° C. by thermogravimetric analysis.

100. The solid form according to any one of embodiments 90 to 99, wherein the total level of residual solvents in the solid form is less than 1%.

101. The solid form according to any one of embodiments 90 to 100, wherein the total level of residual solvents in the solid form is less than 0.5%.

102. The solid form according to any one of embodiments 90 to 101, characterized by a glass transition temperature ($T_g$) greater than 90° C. at 0% relative humidity.

103. The solid form according to any one of embodiments 90 to 102, wherein:
the residual methanol level is less than 3000 ppm;
the residual isopropyl acetate level is less than 5000 ppm; and/or
the residual heptane level is less than 5000 ppm.

104. The solid form according to any one of embodiments 90 to 103, wherein:
the residual methanol level is less than 500 ppm;
the residual isopropyl acetate level is less than 4000 ppm; and/or
the residual heptane level is less than 500 ppm.

105. The solid form according to any one of embodiments 90 to 104, wherein the residual dichloromethane level is less than 1500 ppm.

106. The solid form according to any one of embodiments 90 to 105, wherein the residual dichloromethane level is less than 1000 ppm.

107. The solid form according to any one of embodiments 90 to 106, wherein the residual dichloromethane level is less than 500 ppm.

108. The solid form according to any one of embodiments 90 to 107, wherein the residual dichloromethane level is less than 100 ppm.

109. The solid form according to any one of embodiments 90 to 108, wherein there is no detectable residual solvent in the solid form.

110. The solid form according to any one of embodiments 90 to 109, wherein the solid form is substantially amorphous.

111. A solid form of Compound (I)

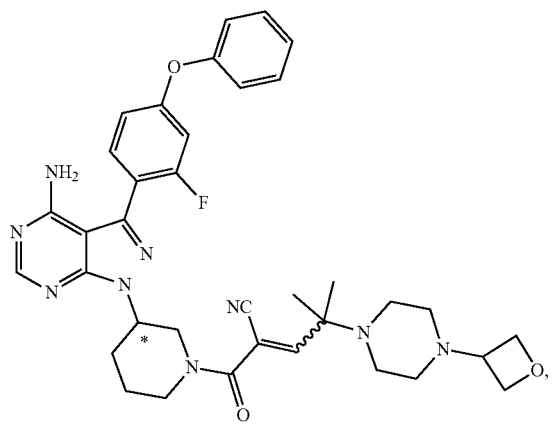 [SMILES: CC(C)(C=C(C#N)C(=O)N1CCCC(Nc2ncnc(N)c2C(=N)c2ccc(Oc3ccccc3)cc2F)C1)N1CCN(C2COC2)CC1]

characterized by a mass loss of less than 5 wt. % between 20° C. and 240° C. by thermogravimetric analysis.

112. The solid form according to embodiment 111, characterized a mass loss of less than 3 wt. % between 20° C. and 240° C. by thermogravimetric analysis.

113. The solid form according to embodiment 111 or 112, characterized by mass loss of less than 2 wt. % between 20° C. and 240° C. by thermogravimetric analysis.

114. The solid form according to any one of embodiments 111 to 113, characterized by mass loss of less than 1.5 wt. % between 20° C. and 240° C. by thermogravimetric analysis.

115. The solid form according to any one of embodiments 111 to 114, wherein the total level of residual solvents in the solid form is less than 1%.

116. The solid form according to any one of embodiments 111 to 115, wherein the total level of residual solvents in the solid form is less than 0.5%.

117. The solid form according to any one of embodiments 111 to 116, characterized by a glass transition temperature ($T_g$) greater than 90° C. at 0% relative humidity.

118. The solid form according to any one of embodiments 111 to 117, wherein:
the residual methanol level is less than 3000 ppm;
the residual isopropyl acetate level is less than 5000 ppm; and/or
the residual heptane level is less than 5000 ppm.

119. The solid form according to any one of embodiments 111 to 118, wherein:
the residual methanol level is less than 500 ppm;
the residual isopropyl acetate level is less than 4000 ppm; and/or
the residual heptane level is less than 500 ppm.

120. The solid form according to any one of embodiments 111 to 119, wherein the residual dichloromethane level is less than 1500 ppm.

121. The solid form according to any one of embodiments 111 to 120, wherein the residual dichloromethane level is less than 1000 ppm.

122. The solid form according to any one of embodiments 111 to 121, wherein the residual dichloromethane level is less than 500 ppm.

123. The solid form according to any one of embodiments 111 to 122, wherein the residual dichloromethane level is less than 100 ppm.

124. The solid form according to any one of embodiments 111 to 123, wherein there is no detectable residual solvent in the solid form.

125. The solid form according to any one of embodiments 111 to 124, wherein the solid form is substantially amorphous.

126. A solid form of Compound (I)

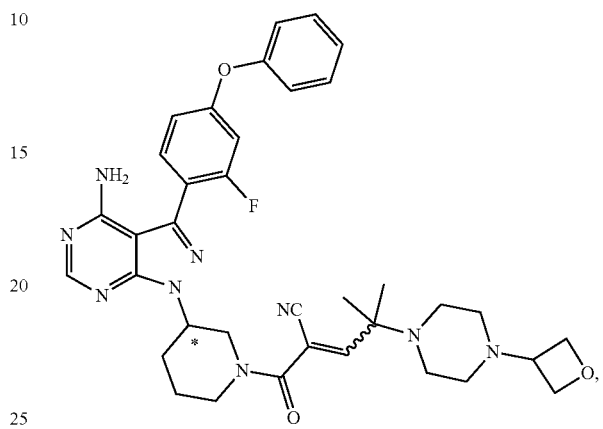

characterized by a glass transition temperature ($T_g$) greater than 90° C. at 0% relative humidity.

127. The solid form according to embodiment 126, wherein:
the residual methanol level is less than 3000 ppm;
the residual isopropyl acetate level is less than 5000 ppm; and/or
the residual heptane level is less than 5000 ppm.

128. The solid form according to embodiment 126 or 127, wherein:
the residual methanol level is less than 500 ppm;
the residual isopropyl acetate level is less than 4000 ppm; and/or
the residual heptane level is less than 500 ppm.

129. The solid form according to any one of embodiments 126 to 128, wherein the residual dichloromethane level is less than 1500 ppm.

130. The solid form according to any one of embodiments 126 to 129, wherein the residual dichloromethane level is less than 1000 ppm.

131. The solid form according to any one of embodiments 126 to 130, wherein the residual dichloromethane level is less than 500 ppm.

132. The solid form according to any one of embodiments 126 to 131, wherein the residual dichloromethane level is less than 100 ppm.

133. The solid form according to any one of embodiments 126 to 132, wherein there is no detectable residual solvent in the solid form.

134. The solid form according to any one of embodiments 126 to 133, wherein the solid form is substantially amorphous.

135. A process for preparing a solid form of Compound (I) comprising adding a base to an aqueous solution comprising Compound (I).

136. The process according to embodiment 135, wherein the base is an aqueous base.

137. The process according to embodiment 135 or 136, wherein the base is aqueous potassium hydroxide.

138. A process for preparing a solid form of Compound (I) comprising:
  washing a solution of Compound (I) with a first aqueous acidic solution to create a first solution comprising a first organic layer and a first aqueous layer, wherein the solution of Compound (I) comprises a first organic solvent; and
  removing the first aqueous layer.
139. The process according to embodiment 138, wherein the first aqueous acidic solution has a pH between 1 and 6.
140. The process according to embodiment 138 or 139, wherein the first aqueous acidic solution has a pH between 2.5 and 3.5.
141. The process according to any one of embodiments 138 to 140, wherein the first aqueous acidic solution is a pH 3 phosphate buffer.
142. The process according to any one of embodiments 138 to 141, wherein the first organic solvent comprises at least one water-immiscible organic solvent.
143. The process according to embodiment 142, wherein the at least one water-immiscible organic solvent is chosen from dichloromethane, ethyl acetate, carbon tetrachloride, chloroform, diethyl ether, di-isopropyl ether, methyl tetrahydrofuran, and isopropyl acetate.
144. The process according to any one of embodiments 138 to 143, wherein the first organic solvent is dichloromethane.
145. The process according to any one of embodiments 138 to 144, further comprising:
  partially removing the first organic solvent from the first organic layer; adding a second organic solvent to the first organic layer, wherein the first organic solvent and the second organic solvent are not the same; and
  adding a second aqueous acidic solution to create a second solution comprising a second organic layer and a second aqueous layer, wherein the second aqueous layer comprises Compound (I).
146. The process according to embodiment 145, wherein partially removing the first organic solvent from the first organic layer comprises distillation under reduced pressure.
147. The process according to embodiment 145 or 146, wherein the second organic solvent is isopropyl acetate.
148. The process according to any one of embodiments 145 to 147, wherein the second aqueous acid solution is an aqueous sulfuric acid solution.
149. The process according to any one of embodiments 138 to 144, further comprising:
  adding a first organic acid to the first organic layer;
  concentrating the first organic layer to remove at least 70% of the first organic solvent;
  adding a third organic solvent to the first organic layer to create a third solution comprising a third organic layer and a third aqueous layer, wherein the third aqueous layer comprises Compound (I) and further wherein the first organic solvent and the third organic solvent are not the same; and
  adding a first base to adjust the pH of the third aqueous layer to between 2.5 and 3.5.
150. The process according to embodiment 149, wherein the first organic acid is methanesulfonic acid.
151. The process according to embodiment 149 or 150, wherein concentrating the first organic layer to remove at least 70% of the first organic solvent comprises distillation under reduced pressure.
152. The process according to any one of embodiments 149 to 151, wherein the third organic solvent is isopropyl acetate.
153. The process according to any one of embodiments 149 to 152, wherein the first base is an aqueous base.
154. The process according to any one of embodiments 149 to 153, wherein the first base is aqueous potassium hydroxide.
155. The process according to embodiment 145 or 149, further comprising:
  removing the second organic layer or the third organic layer;
  removing residual organic solvent in the second aqueous layer or the third aqueous layer to create an aqueous solution of Compound (I); and
  adding a second base to the aqueous solution of Compound (I) to create a precipitate comprising Compound (I).
156. The process according to embodiment 155, wherein removing residual organic solvent in the second aqueous phase or the third aqueous phase comprises distillation under reduced pressure.
157. The process according to embodiment 155 or 156, wherein the second base is an aqueous base.
158. The process according to any one of embodiments 155 to 157, wherein the second base is aqueous potassium hydroxide.
159. The process according to any one of embodiments 155 to 158, further comprising filtering and drying the precipitate.
160. The process according to embodiment 159, wherein the precipitate is substantially free of degradation products.
161. The process according to embodiment 159 or 160, wherein residual solvents comprise less than 1% of the precipitate.
162. A process for preparing a solid form of Compound (I) comprising:
  washing a solution comprising Compound (I) and an organic solvent with an aqueous solution of a weak organic acid having a pKa less than or equal to 7 to create a first solution comprising a first organic layer and a first aqueous layer; and
  removing the first aqueous layer, leaving behind the first organic layer comprising Compound (I).
163. The process according to embodiment 162, wherein the organic solvent comprises at least one water-immiscible organic solvent.
164. The process according to embodiment 163, wherein the water-immiscible organic solvent is chosen from dichloromethane, ethyl acetate, carbon tetrachloride, chloroform, diethyl ether, di-isopropyl ether, methyl tetrahydrofuran, and isopropyl acetate.
165. The process according to any one of embodiments 162 to 164, wherein the organic solvent is dichloromethane.
166. The process according to any one of embodiments 162 to 165, wherein the weak organic acid having a pKa less than or equal to 7 is chosen from acetic acid, citric acid, formic acid, and propanoic acid.
167. The process according to any one of embodiments 162 to 166, wherein the weak organic acid having a pKa less than or equal to 7 is acetic acid.
168. The process according to any one of embodiments 162 to 167, further comprising washing the first organic layer comprising Compound (I) with aqueous sodium bicarbonate.
169. The process according to any one of embodiments 162 to 168, further comprising:
  adding a strong acid to the first organic layer; and
  concentrating the first organic layer by removing the organic solvent to provide a residue comprising Compound (I).

170. The process according to embodiment 169, wherein the strong acid is chosen from methanesulfonic acid, sulfuric acid, and hydrochloric acid.

171. The process according to embodiment 169 or 170, wherein the strong acid is methanesulfonic acid.

172. The process according to any one of embodiments 162 to 171, further comprising cooling the residue comprising Compound (I) to a temperature between 0° C. and 10° C.

173. The process according to embodiment 172, wherein the residue comprising Compound (I) is cooled to a temperature of 5° C.

174. The process according to any one of embodiments 162 to 173, further comprising washing the residue comprising Compound (I) with water or an aqueous salt solution.

175. The process according to embodiment 174, wherein the aqueous salt solution is an aqueous solution of sodium chloride.

176. The process according to embodiment 174 or 175, further comprising:
    adding a water-immiscible organic solvent to provide a second organic layer, and a second aqueous layer comprising Compound (I); and
    removing the second organic layer.

177. The process according to embodiment 174, wherein washing the residue comprising Compound (I) with water or an aqueous salt solution is repeated 1 to 3 times.

178. The process according to any one of embodiments 169 to 177, further comprising adjusting the pH of the first or second aqueous layer to a value between 1 and 5 by adding an aqueous base.

179. The process according to embodiment 178, wherein the pH of the first or second aqueous layer is adjusted to 3.

180. The process according to embodiment 178 or 179, wherein the aqueous base is an aqueous solution of sodium hydroxide, potassium hydroxide, or calcium hydroxide.

181. The process according to any one of embodiments 178 to 180, further comprising determining a level of residual weak organic acid having a pKa less than or equal to 7 in the first or second aqueous layer, and adjusting the level of the weak organic acid having a pKa less than or equal to 7 to 0 wt. % to 8 wt. %.

182. The process according to embodiment 181, wherein the weak organic acid having a pKa less than or equal to 7 is acetic acid.

183. The process according to embodiment 181 or 182, further comprising adding an aqueous base to the first or second aqueous layer to obtain a pH between 8 and 11 and allowing a precipitate comprising Compound (I) to form.

184. The process according to embodiment 183, wherein the pH is 9.5.

185. The process according to embodiment 183 or 184, wherein the aqueous base is an aqueous solution of potassium hydroxide.

186. The process according to any one of embodiment 183 to 185, further comprising isolating the precipitate comprising Compound (I) by filtering, and washing the precipitate comprising Compound (I) with water.

187. The process according to embodiment 186, further comprising drying the filtered and washed precipitate comprising Compound (I) to provide a solid form of Compound (I).

188. The process according to embodiment 186, further comprising slurrying the isolated precipitate with water and filtering to provide a solid form of Compound (I).

189. A process for preparing a solid form of Compound (I) comprising:
    dissolving a crystalline form of Compound (I) in a solution comprising a water-immiscible organic solvent and brine;
    adding one equivalent of a strong acid to create an aqueous layer and an organic layer;
    removing the organic layer;
    concentrating the aqueous layer;
    adding an aqueous base to adjust the pH to a value between 8 and 11 to obtain a precipitate of a solid form of Compound (I);
    isolating the precipitate of the solid form of Compound (I) by filtering;
    rinsing the precipitate with water; and
    drying the precipitate to obtain a solid form of Compound (I).

190. The process according to embodiment 189, wherein the water-immiscible organic solvent is dichloromethane.

191. The process according to embodiment 189 or 190, wherein the strong acid is methanesulfonic acid.

192. The process according to any one of embodiments 189 to 191, wherein after the addition of the strong acid, the pH of the aqueous layer is between 1 and 4.

193. The process according to embodiment 192, wherein the pH of the aqueous layer is 2.

194. The process according any one of embodiments 189 to 193, wherein the aqueous layer is concentrated at a temperature between 0° C. and 5° C.

195. The process according to any one of embodiments 189 to 194, wherein the aqueous base is an aqueous potassium hydroxide solution.

196. The process according to any one of embodiments 189 to 195, wherein the aqueous base is added to adjust the pH to a value between 9 and 10.

197. The process according to any one of embodiments 189 to 196, wherein prior to isolating the precipitate of a solid form of Compound (I), the aqueous layer comprising the precipitate is warmed to room temperature.

198. The process according to any one of embodiments 135 to 197, further comprising micronizing particles of Compound (I).

199. A solid form of Compound (I) made by the process according to any one of embodiments 135 to 198.

200. The solid form according to embodiment 175, wherein the solid form is substantially amorphous.

201. A process for preparing a solid form of Compound (I) comprising spray drying a solution of Compound (I).

202. A process for preparing an amorphous form of Compound (I) comprising:
    washing a solution of Compound (I) with a first aqueous acidic solution to create a first solution comprising a first organic layer and a first aqueous layer, wherein the solution of Compound (I) comprises a first organic solvent;
    removing the first aqueous layer; and
    performing a solvent exchange from the first organic solvent to a second organic solvent.

203. The process according to embodiment 202, wherein the first aqueous acidic solution has a pH between 1 and 6.

204. The process according to embodiment 202 or 203, wherein the first aqueous acidic solution has a pH between 2.5 and 3.5.

205. The process according to any one of embodiments 202 to 204, wherein the first aqueous acidic solution is a pH 3 phosphate buffer.

206. The process according to any one of embodiments 202 to 205, wherein the first organic solvent comprises at least one water-immiscible organic solvent.

207. The process according to embodiment 206, wherein the at least one water-immiscible organic solvent is chosen from dichloromethane, ethyl acetate, carbon tetrachloride, chloroform, diethyl ether, di-isopropyl ether, methyl tetrahydrofuran, and isopropyl acetate.

208. The process according to any one of embodiments 202 to 207, wherein the first organic solvent comprises dichloromethane.

209. The process according to any one of embodiments 202 to 208, wherein the second organic solvent comprises at least one of alkyl acetate, methyl tetrahydrofuran, toluene, methyl cyclopentyl ether, methyl tert-butyl ether, pentanone, acetonitrile and alkyl propionate.

210. The process according to embodiment 209, wherein the alkyl acetate is isopropyl acetate.

211. The process according to embodiment 209 or 210, wherein the second organic solvent comprises isopropyl acetate.

212. The process according to any one of embodiments 202 to 211, further comprising:
washing the first organic layer with a second aqueous acidic solution to create a second solution comprising a second organic layer and a second aqueous layer, wherein the second aqueous layer comprises Compound (I); and
removing the second organic layer.

213. The process according to embodiment 212, wherein the second aqueous acidic solution has a pH between 1 and 6.

214. The process according to embodiment 212 or 213, wherein the second aqueous acidic solution has a pH between 2.5 and 3.5.

215. The process according to any one of embodiments 212 to 214, wherein the second aqueous acidic solution is a pH 3 phosphate buffer.

216. The process according to any one of embodiments 212 to 215, further comprising:
adding a first base to the second aqueous layer to create a third solution comprising a third organic layer and a third aqueous layer, wherein the third organic layer comprises Compound (I);
extracting the third aqueous layer using a third organic solvent; and
concentrating the third organic layer.

217. The process according to embodiment 216, wherein the first base is an aqueous base.

218. The process according to embodiment 217, wherein the aqueous base has a pH between 8 and 14.

219. The process according to any one of embodiments 216 to 218, wherein the first base is aqueous potassium hydroxide.

220. The process according to any one of embodiments 216 to 219, wherein the third organic solvent comprises at least one of alkyl acetate, methyl tetrahydrofuran, toluene, methyl cyclopentyl ether, methyl tert-butyl ether, pentanone, acetonitrile and alkyl propionate.

221. The process according to embodiment 220, wherein the alkyl acetate is isopropyl acetate.

222. The process according to any one of embodiments 216 to 221, wherein the third organic solvent comprises isopropyl acetate.

223. The process according to any one of embodiments 216 to 222, further comprising adding an antisolvent to the third organic layer to create a precipitate comprising Compound (I).

224. The process according to embodiment 223, wherein the antisolvent comprises at least one of hexanes, heptanes, and octanes.

225. The process according to embodiment 223 or 224, further comprising isolating the precipitate comprising Compound (I).

226. The process according to embodiment 225, wherein isolating the precipitate comprising Compound (I) comprises drying the precipitate comprising Compound (I).

227. The process according to embodiment 226, wherein drying comprises air drying, blow drying, or vacuum-drying.

228. The process according to any one of embodiments 225 to 227, further comprising:
dissolving the precipitate comprising Compound (I) in a fourth organic solvent to create a fourth solution; and
spray drying the fourth solution to obtain a solid form of Compound (I).

229. The process according to embodiment 228, wherein the fourth organic solvent comprises at least one of methanol, ethanol, acetone, acetonitrile, and methyl ethyl ketone.

230. The process according to embodiment 229, wherein the fourth organic solvent comprises methanol.

231. The process according to any one of embodiments 228 to 230, wherein the solid form of Compound (I) is substantially free of degradation products.

232. The process according to any one of embodiments 228 to 231, wherein residual solvents comprise less than 1% of the solid form of Compound (I).

233. The process according to any one of embodiments 228 to 232, further comprising micronizing the solid form of Compound (I).

234. A solid form of Compound (I) made by the process according to any one of embodiments 201 to 233.

235. The solid form according to embodiment 234, wherein the solid form is substantially amorphous.

236. A pharmaceutical composition comprising:
a solid form of Compound (I) according to any one of embodiments 1 to 134, 199, 200, 234, or 235; and
at least one pharmaceutically acceptable excipient.

237. The pharmaceutical composition according to embodiment 236, wherein the pharmaceutical composition is in the form of a solid oral composition.

238. The pharmaceutical composition according to embodiment 236 or 237, wherein the pharmaceutical composition is in the form of a tablet or a capsule.

239. A method of inhibiting Bruton's tyrosine kinase (BTK) in a mammal in need of such BTK inhibition comprising administering to the mammal a therapeutically effective amount of a solid form of Compound (I) according to any one of embodiments 1 to 134, 199, 200, 234, or 235.

240. A method of treating a disease mediated by Bruton's tyrosine kinase (BTK) in a mammal in need thereof comprising administering to the mammal a therapeutically effective amount of a solid form of Compound (I) according to any one of embodiments 1 to 134, 199, 200, 234, or 235.

241. A method of treating *Pemphigus vulgaris* or *Pemphigus foliaceus* in a mammal in need thereof comprising administering to the mammal a therapeutically effective amount of a solid form of Compound (I) according to any one of embodiments 1 to 134, 199, 200, 234, or 235.

242. A method of treating immune thrombocytopenia in a mammal in need thereof comprising administering to the mammal a therapeutically effective amount of a solid form of Compound (I) according any one of embodiments 1 to 134, 199, 200, 234, or 235.

243. The method of any one of embodiments 239 to 242, wherein the mammal is a human.

Mean Bulk Density of Solid Forms

Mean bulk density reflects the amount of space occupied by a given amount of material. Mean bulk density may affect how a material behaves during process operations (e.g., blending and compaction). In some instances, mean bulk density may influence the selection of a formulation procedure for a material during pharmaceutical development.

In some embodiments, a solid form of the present disclosure is characterized by a mean bulk density greater than 0.30 g/cc. In some embodiments, a solid form of the present disclosure is characterized by a mean bulk density greater than 0.35 g/cc. In some embodiments, a solid form of the present disclosure is characterized by a mean bulk density greater than 0.40 g/cc. In some embodiments, a solid form of the present disclosure is characterized by a mean bulk density greater than 0.45 g/cc. In some embodiments, a solid form of the present disclosure is characterized by a mean bulk density greater than 0.50 g/cc. In some embodiments, a solid form of the present disclosure is characterized by a mean bulk density greater than 0.55 g/cc. In some embodiments, a solid form of the present disclosure is characterized by a mean bulk density greater than 0.60 g/cc. In some embodiments, a solid form of the present disclosure is characterized by a mean bulk density greater than 0.65 g/cc.

In some embodiments, the process provides a solid form of Compound (I), characterized by a mean bulk density between than 0.6 g/cc and 0.7 g/cc.

In some embodiments, a solid form of the present disclosure is characterized by a mean bulk density between 0.30 g/cc and 0.70 g/cc. In some embodiments, a solid form of the present disclosure is characterized by a mean bulk density between 0.30 g/cc and 0.35 g/cc. In some embodiments, a solid form of the present disclosure is characterized by a mean bulk density between 0.35 g/cc and 0.40 g/cc. In some embodiments, a solid form of the present disclosure is characterized by a mean bulk density between 0.40 g/cc and 0.45 g/cc. In some embodiments, a solid form of the present disclosure is characterized by a mean bulk density between 0.45 g/cc and 0.50 g/cc. In some embodiments, a solid form of the present disclosure is characterized by a mean bulk density between 0.50 g/cc and 0.55 g/cc. In some embodiments, a solid form of the present disclosure is characterized by a mean bulk density between 0.55 g/cc and 0.60 g/cc. In some embodiments, a solid form of the present disclosure is characterized by a mean bulk density between 0.60 g/cc and 0.65 g/cc. In some embodiments, a solid form of the present disclosure is characterized by a mean bulk density between 0.65 g/cc and 0.70 g/cc.

In some embodiments, a solid form of the present disclosure is characterized by a mean bulk density between 0.30 g/cc and 0.32 g/cc. In some embodiments, a solid form of the present disclosure is characterized by a mean bulk density between 0.32 g/cc and 0.34 g/cc. In some embodiments, a solid form of the present disclosure is characterized by a mean bulk density between 0.34 g/cc and 0.36 g/cc. In some embodiments, a solid form of the present disclosure is characterized by a mean bulk density between 0.36 g/cc and 0.38 g/cc. In some embodiments, a solid form of the present disclosure is characterized by a mean bulk density between 0.38 g/cc and 0.40 g/cc. In some embodiments, a solid form of the present disclosure is characterized by a mean bulk density between 0.40 g/cc and 0.42 g/cc. In some embodiments, a solid form of the present disclosure is characterized by a mean bulk density between 0.42 g/cc and 0.44 g/cc. In some embodiments, a solid form of the present disclosure is characterized by a mean bulk density between 0.44 g/cc and 0.46 g/cc. In some embodiments, a solid form of the present disclosure is characterized by a mean bulk density between 0.46 g/cc and 0.48 g/cc. In some embodiments, a solid form of the present disclosure is characterized by a mean bulk density between 0.48 g/cc and 0.50 g/cc. In some embodiments, a solid form of the present disclosure is characterized by a mean bulk density between 0.50 g/cc and 0.52 g/cc. In some embodiments, a solid form of the present disclosure is characterized by a mean bulk density between 0.52 g/cc and 0.54 g/cc. In some embodiments, a solid form of the present disclosure is characterized by a mean bulk density between 0.54 g/cc and 0.56 g/cc. In some embodiments, a solid form of the present disclosure is characterized by a mean bulk density between 0.56 g/cc and 0.58 g/cc. In some embodiments, a solid form of the present disclosure is characterized by a mean bulk density between 0.58 g/cc and 0.60 g/cc. In some embodiments, a solid form of the present disclosure is characterized by a mean bulk density between 0.60 g/cc and 0.62 g/cc. In some embodiments, a solid form of the present disclosure is characterized by a mean bulk density between 0.62 g/cc and 0.64 g/cc. In some embodiments, a solid form of the present disclosure is characterized by a mean bulk density between 0.64 g/cc and 0.66 g/cc. In some embodiments, a solid form of the present disclosure is characterized by a mean bulk density between 0.66 g/cc and 0.68 g/cc. In some embodiments, a solid form of the present disclosure is characterized by a mean bulk density between 0.68 g/cc and 0.70 g/cc.

Mean Tapped Density of Solid Forms

"Mean tapped density" or "tapped density" refers to the bulk density determined after mechanically tapping a container containing a powder sample. Tapped density may affect the behavior of a pharmaceutical material, e.g., during precompaction, tableting, and capsule filling.

In some embodiments, a solid form of the present disclosure is characterized by a mean tapped density greater than 0.50 g/cc. In some embodiments, a solid form of the present disclosure is characterized by a mean tapped density greater than 0.55 g/cc. In some embodiments, a solid form of the present disclosure is characterized by a mean tapped density greater than 0.60 g/cc. In some embodiments, a solid form of the present disclosure is characterized by a mean tapped density greater than 0.65 g/cc. In some embodiments, a solid form of the present disclosure is characterized by a mean tapped density greater than 0.70 g/cc. In some embodiments, a solid form of the present disclosure is characterized by a mean tapped density greater than 0.75 g/cc. In some embodiments, a solid form of the present disclosure is characterized by a mean tapped density greater than 0.80 g/cc. In some embodiments, a solid form of the present disclosure is characterized by a mean tapped density greater than 0.85 g/cc.

In some embodiments, a solid form of the present disclosure is characterized by a mean tapped density between 0.70 g/cc and 0.90 g/cc. In some embodiments, a solid form of the present disclosure is characterized by a mean tapped density between 0.70 g/cc and 0.75 g/cc. In some embodiments, a solid form of the present disclosure is characterized by a mean tapped density between 0.75 g/cc and 0.80 g/cc. In some embodiments, a solid form of the present disclosure is characterized by a mean tapped density between 0.80 g/cc and 0.85 g/cc. In some embodiments, a solid form of the present disclosure is characterized by a mean tapped density between 0.85 g/cc and 0.90 g/cc.

In some embodiments, a solid form of the present disclosure is characterized by a mean tapped density between 0.70 g/cc and 0.72 g/cc. In some embodiments, a solid form of the present disclosure is characterized by a mean tapped density between 0.72 g/cc and 0.74 g/cc. In some embodiments, a solid form of the present disclosure is characterized by a mean tapped density between 0.74 g/cc and 0.76 g/cc. In some embodiments, a solid form of the present disclosure is characterized by a mean tapped density between 0.76 g/cc and 0.78 g/cc. In some embodiments, a solid form of the present disclosure is characterized by a mean tapped density between 0.78 g/cc and 0.80 g/cc. In some embodiments, a solid form of the present disclosure is characterized by a mean tapped density between 0.80 g/cc and 0.82 g/cc. In some embodiments, a solid form of the present disclosure is characterized by a mean tapped density between 0.82 g/cc and 0.84 g/cc. In some embodiments, a solid form of the present disclosure is characterized by a mean tapped density between 0.88 g/cc and 0.86 g/cc. In some embodiments, a solid form of the present disclosure is characterized by a mean tapped density between 0.86 g/cc and 0.88 g/cc. In some embodiments, a solid form of the present disclosure is characterized by a mean tapped density between 0.88 g/cc and 0.90 g/cc.

Hausner Ratio of Solid Forms

The Hausner ratio indicates the flowability of a powder, with a Hausner ratio greater than 1.35 often considered an indication of poor flowability. Powder flow is a key requirement for most pharmaceutical manufacturing processes. Passable flowability of a powder, with a Hausner ratio of less than 1.34, is often required to ensure consistent content uniformity.

In some embodiments, a solid form of the present disclosure is characterized by a Hausner ratio less than or equal to 1.2. In some embodiments, a solid form of the present disclosure is characterized by a Hausner ratio less than or equal to 1.18. In some embodiments, a solid form of the present disclosure is characterized by a Hausner ratio less than or equal to 1.16. In some embodiments, a solid form of the present disclosure is characterized by a Hausner ratio less than or equal to 1.14. In some embodiments, a solid form of the present disclosure is characterized by a Hausner ratio less than or equal to 1.12. In some embodiments, a solid form of the present disclosure is characterized by a Hausner ratio less than or equal to 1.10. In some embodiments, a solid form of the present disclosure is characterized by a Hausner ratio less than or equal to 1.08. In some embodiments, a solid form of the present disclosure is characterized by a Hausner ratio less than or equal to 1.06. In some embodiments, a solid form of the present disclosure is characterized by a Hausner ratio less than or equal to 1.04. In some embodiments, a solid form of the present disclosure is characterized by a Hausner ratio less than or equal to 1.02. In some embodiments, a solid form of the present disclosure is characterized by a Hausner ratio less than or equal to 1.00.

In some embodiments, a solid form of the present disclosure is characterized by a Hausner ratio between 1 and 1.2. In some embodiments, a solid form of the present disclosure is characterized by a Hausner ratio between 1.00 and 1.05. In some embodiments, a solid form of the present disclosure is characterized by a Hausner ratio between 1.05 and 1.10. In some embodiments, a solid form of the present disclosure is characterized by a Hausner ratio between 1.10 and 1.15. In some embodiments, a solid form of the present disclosure is characterized by a Hausner ratio between 1.15 and 1.20.

Wet Particle Size Distribution of Solid Forms

Particle size is associated with several relevant properties for pharmaceutical processing, including particle shape, surface area, and porosity. The particle size distribution of an API may affect bulk properties, product performance, processability, and API stability. For example, particle size distribution may affect API dissolution and absorption rates, as well as product consistency. For some pharmaceutical applications, smaller particle sizes are desirable.

In some embodiments, a solid form of the present disclosure is characterized by a wet particle size distribution having a $D_{10}$ value greater than 70 μm. In some embodiments, a solid form of the present disclosure is characterized by a wet particle size distribution having a $D_{10}$ value greater than 75 μm. In some embodiments, a solid form of the present disclosure is characterized by a wet particle size distribution having a $D_{10}$ value greater than 80 μm. In some embodiments, a solid form of the present disclosure is characterized by a wet particle size distribution having a $D_{10}$ value greater than 85 μm. In some embodiments, a solid form of the present disclosure is characterized by a wet particle size distribution having a $D_{10}$ value greater than 90 μm. In some embodiments, a solid form of the present disclosure is characterized by a wet particle size distribution having a $D_{10}$ value greater than 95 μm. In some embodiments, a solid form of the present disclosure is characterized by a wet particle size distribution having a $D_{10}$ value greater than 100 μm. In some embodiments, a solid form of the present disclosure is characterized by a wet particle size distribution having a $D_{10}$ value greater than 105 μm. In some embodiments, a solid form of the present disclosure is characterized by a wet particle size distribution having a $D_{10}$ value greater than 110 μm. In some embodiments, a solid form of the present disclosure is characterized by a wet particle size distribution having a $D_{10}$ value greater than 115 μm. In some embodiments, a solid form of the present disclosure is characterized by a wet particle size distribution having a $D_{10}$ value greater than 120 μm. In some embodiments, a solid form of the present disclosure is characterized by a wet particle size distribution having a $D_{10}$ value greater than 125 μm. In some embodiments, a solid form of the present disclosure is characterized by a wet particle size distribution having a $D_{10}$ value greater than 130 μm. In some embodiments, a solid form of the present disclosure is characterized by a wet particle size distribution having a $D_{10}$ value greater than 135 μm. In some embodiments, a solid form of the present disclosure is characterized by a wet particle size distribution having a $D_{10}$ value greater than 140 μm. In some embodiments, a solid form of the present disclosure is characterized by a wet particle size distribution having a $D_{10}$ value greater than 145 μm. In some embodiments, a solid form of the present disclosure is characterized by a wet particle size distribution having a $D_{10}$ value greater than 150 μm.

In some embodiments, a solid form of the present disclosure is characterized by a wet particle size distribution having a $D_{10}$ value between 70 μm and 150 μm. In some embodiments, a solid form of the present disclosure is characterized by a wet particle size distribution having a $D_{10}$ value between 80 μm and 150 μm. In some embodiments, a solid form of the present disclosure is characterized by a wet particle size distribution having a $D_{10}$ value between 90 μm and 150 μm. In some embodiments, a solid form of the present disclosure is characterized by a wet particle size distribution having a $D_{10}$ value between 100 μm and 150 μm.

In some embodiments, a solid form of the present disclosure is characterized by a wet particle size distribution having a $D_{50}$ value greater than 200 μm. In some embodiments, a solid form of the present disclosure is characterized by a wet particle size distribution having a $D_{50}$ value greater than 205 μm. In some embodiments, a solid form of the present disclosure is characterized by a wet particle size distribution having a $D_{50}$ value greater than 210 μm. In some embodiments, a solid form of the present disclosure is characterized by a wet particle size distribution having a $D_{50}$ value greater than 215 μm. In some embodiments, a solid form of the present disclosure is characterized by a wet particle size distribution having a $D_{50}$ value greater than 220 μm. In some embodiments, a solid form of the present disclosure is characterized by a wet particle size distribution having a $D_{50}$ value greater than 225 μm. In some embodiments, a solid form of the present disclosure is characterized by a wet particle size distribution having a $D_{50}$ value greater than 230 μm. In some embodiments, a solid form of the present disclosure is characterized by a wet particle size distribution having a $D_{50}$ value greater than 235 μm. In some embodiments, a solid form of the present disclosure is characterized by a wet particle size distribution having a $D_{50}$ value greater than 240 μm. In some embodiments, a solid form of the present disclosure is characterized by a wet particle size distribution having a $D_{50}$ value greater than 245 μm. In some embodiments, a solid form of the present disclosure is characterized by a wet particle size distribution having a $D_{50}$ value greater than 250 μm. In some embodiments, a solid form of the present disclosure is characterized by a wet particle size distribution having a $D_{50}$ value greater than 255 μm. In some embodiments, a solid form of the present disclosure is characterized by a wet particle size distribution having a $D_{50}$ value greater than 260 μm. In some embodiments, a solid form of the present disclosure is characterized by a wet particle size distribution having a $D_{50}$ value greater than 265 μm. In some embodiments, a solid form of the present disclosure is characterized by a wet particle size distribution having a $D_{50}$ value greater than 270 μm. In some embodiments, a solid form of the present disclosure is characterized by a wet particle size distribution having a $D_{50}$ value greater than 275 μm. In some embodiments, a solid form of the present disclosure is characterized by a wet particle size distribution having a $D_{50}$ value greater than 280 μm. In some embodiments, a solid form of the present disclosure is characterized by a wet particle size distribution having a $D_{50}$ value greater than 285 μm. In some embodiments, a solid form of the present disclosure is characterized by a wet particle size distribution having a $D_{50}$ value greater than 290 μm. In some embodiments, a solid form of the present disclosure is characterized by a wet particle size distribution having a $D_{50}$ value greater than 295 μm. In some embodiments, a solid form of the present disclosure is characterized by a wet particle size distribution having a $D_{50}$ value greater than 300 μm.

In some embodiments, a solid form of the present disclosure is characterized by a wet particle size distribution having a $D_{50}$ value between 200 μm and 400 μm. In some embodiments, a solid form of the present disclosure is characterized by a wet particle size distribution having a $D_{50}$ value between 200 μm and 300 μm. In some embodiments, a solid form of the present disclosure is characterized by a wet particle size distribution having a $D_{50}$ value between 225 μm and 275 μm.

In some embodiments, a solid form of the present disclosure is characterized by a wet particle size distribution having a $D_{90}$ value greater than 400 μm. In some embodiments, a solid form of the present disclosure is characterized by a wet particle size distribution having a $D_{90}$ value greater than 425 μm. In some embodiments, a solid form of the present disclosure is characterized by a wet particle size distribution having a $D_{90}$ value greater than 450 μm. In some embodiments, a solid form of the present disclosure is characterized by a wet particle size distribution having a $D_{90}$ value greater than 475 μm. In some embodiments, a solid form of the present disclosure is characterized by a wet particle size distribution having a $D_{90}$ value greater than 500 μm. In some embodiments, a solid form of the present disclosure is characterized by a wet particle size distribution having a $D_{90}$ value greater than 525 μm. In some embodiments, a solid form of the present disclosure is characterized by a wet particle size distribution having a $D_{90}$ value greater than 550 μm.

In some embodiments, a solid form of the present disclosure is characterized by a wet particle size distribution having a $D_{90}$ value between 400 μm and 800 μm. In some embodiments, a solid form of the present disclosure is characterized by a wet particle size distribution having a $D_{90}$ value between 400 μm and 700 μm. In some embodiments, a solid form of the present disclosure is characterized by a wet particle size distribution having a $D_{90}$ value between 450 μm and 700 μm.

In some embodiments, a solid form of the present disclosure is characterized by a wet particle size distribution having a $D_{10}$ value less than 10 μm. In some embodiments, a solid form of the present disclosure is characterized by a wet particle size distribution having a $D_{10}$ value less than 9 μm. In some embodiments, a solid form of the present disclosure is characterized by a wet particle size distribution having a $D_{10}$ value less than 8 μm. In some embodiments, a solid form of the present disclosure is characterized by a wet particle size distribution having a $D_{10}$ value less than 7 μm. In some embodiments, a solid form of the present disclosure is characterized by a wet particle size distribution having a $D_{10}$ value less than 6 μm. In some embodiments, a solid form of the present disclosure is characterized by a wet particle size distribution having a $D_{10}$ value less than 5 μm. In some embodiments, a solid form of the present disclosure is characterized by a wet particle size distribution having a $D_{10}$ value less than 4 μm. In some embodiments, a solid form of the present disclosure is characterized by a wet particle size distribution having a $D_{10}$ value less than 3 μm. In some embodiments, a solid form of the present disclosure is characterized by a wet particle size distribution having a $D_{10}$ value less than 2 μm.

In some embodiments, a solid form of the present disclosure is characterized by a wet particle size distribution having a $D_{10}$ value between 5 μm and 6 μm. In some embodiments, a solid form of the present disclosure is characterized by a wet particle size distribution having a $D_{10}$ value between 1 μm and 2 μm.

In some embodiments, a solid form of the present disclosure is characterized by a wet particle size distribution having a $D_{50}$ value less than 100 μm. In some embodiments, a solid form of the present disclosure is characterized by a wet particle size distribution having a $D_{50}$ value less than 90 μm. In some embodiments, a solid form of the present disclosure is characterized by a wet particle size distribution having a $D_{50}$ value less than 80 μm. In some embodiments, a solid form of the present disclosure is characterized by a wet particle size distribution having a $D_{50}$ value less than 70 μm. In some embodiments, a solid form of the present disclosure is characterized by a wet particle size distribution having a $D_{50}$ value less than 60 μm. In some embodiments, a solid form of the present disclosure is characterized by a wet particle size distribution having a $D_{50}$ value less than 50 μm. In some embodiments, a solid form of the present disclosure is characterized by a wet particle size distribution having a $D_{50}$ value less than 40 μm. In some embodiments, a solid form of the present disclosure is characterized by a wet particle size distribution having a $D_{50}$ value less than 30 μm. In some embodiments, a solid form of the present disclosure is characterized by a wet particle size distribution having a $D_{50}$ value less than 20 μm.

In some embodiments, a solid form of the present disclosure is characterized by a wet particle size distribution having a $D_{50}$ value between 40 μm and 70 μm. In some embodiments, a solid form of the present disclosure is characterized by a wet particle size distribution having a $D_{50}$ value between 10 μm and 20 μm.

In some embodiments, a solid form of the present disclosure is characterized by a wet particle size distribution having a $D_{10}$ value between 5 μm and 6 μm and a $D_{50}$ value between 10 μm and 20 μm. In some embodiments, a solid form of the present disclosure is characterized by a wet particle size distribution having a $D_{10}$ value between 1 μm and 2 μm and a $D_{50}$ value between 40 μm and 70 μm.

In some embodiments, a solid form of the present disclosure is characterized by a wet particle size distribution having a $D_{90}$ value less than 200 μm. In some embodiments, a solid form of the present disclosure is characterized by a wet particle size distribution having a $D_{90}$ value less than 190 μm. In some embodiments, a solid form of the present disclosure is characterized by a wet particle size distribution having a $D_{90}$ value less than 180 μm. In some embodiments, a solid form of the present disclosure is characterized by a wet particle size distribution having a $D_{90}$ value less than 170 μm. In some embodiments, a solid form of the present disclosure is characterized by a wet particle size distribution having a $D_{90}$ value less than 160 μm. In some embodiments, a solid form of the present disclosure is characterized by a wet particle size distribution having a $D_{90}$ value less than 150 μm. In some embodiments, a solid form of the present disclosure is characterized by a wet particle size distribution having a $D_{90}$ value less than 140 μm. In some embodiments, a solid form of the present disclosure is characterized by a wet particle size distribution having a $D_{90}$ value less than 130 μm. In some embodiments, a solid form of the present disclosure is characterized by a wet particle size distribution having a $D_{90}$ value less than 120 μm. In some embodiments, a solid form of the present disclosure is characterized by a wet particle size distribution having a $D_{90}$ value less than 110 μm. In some embodiments, a solid form of the present disclosure is characterized by a wet particle size distribution having a $D_{90}$ value less than 100 μm. In some embodiments, a solid form of the present disclosure is characterized by a wet particle size distribution having a $D_{90}$ value less than 90 μm. In some embodiments, a solid form of the present disclosure is characterized by a wet particle size distribution having a $D_{90}$ value less than 80 μm. In some embodiments, a solid form of the present disclosure is characterized by a wet particle size distribution having a $D_{90}$ value less than 70 μm. In some embodiments, a solid form of the present disclosure is characterized by a wet particle size distribution having a $D_{90}$ value less than 60 μm. In some embodiments, a solid form of the present disclosure is characterized by a wet particle size distribution having a $D_{90}$ value less than 50 μm. In some embodiments, a solid form of the present disclosure is characterized by a wet particle size distribution having a $D_{90}$ value less than 40 μm. In some embodiments, a solid form of the present disclosure is characterized by a wet particle size distribution having a $D_{90}$ value less than 30 μm.

In some embodiments, a solid form of the present disclosure is characterized by a wet particle size distribution having a $D_{90}$ value between 100 μm and 150 μm. In some embodiments, a solid form of the present disclosure is characterized by a wet particle size distribution having a $D_{90}$ value between 10 μm and 50 μm.

In some embodiments, a solid form of the present disclosure is characterized by a wet particle size distribution having a $D_{90}$ value between 100 μm and 150 μm and a $D_{50}$ value between 40 μm and 70 μm. In some embodiments, a solid form of the present disclosure is characterized by a wet particle size distribution having a $D_{90}$ value between 10 μm and 50 μm and a $D_{50}$ value between 10 μm and 20 μm.

In some embodiments, a solid form of the present disclosure is characterized by a wet particle size distribution having a $D_{10}$ value between 5 μm and 6 μm and a $D_{90}$ value between 10 μm and 50 μm. In some embodiments, a solid form of the present disclosure is characterized by a wet particle size distribution having a $D_{10}$ value between 1 μm and 2 μm and a $D_{90}$ value between 100 μm and 150 μm.

In some embodiments, a solid form of the present disclosure is characterized by a wet particle size distribution having a $D_{10}$ value between 5 μm and 6 μm, a $D_{50}$ value between 10 μm and 20 μm, and a $D_{90}$ value between 10 μm and 50 μm. In some embodiments, a solid form of the present disclosure is characterized by a wet particle size distribution having a $D_{10}$ value between 1 μm and 2 μm, a $D_{50}$ value between 40 μm and 70 μm, and a $D_{90}$ value between 100 μm and 150 μm.

Residual Solvent Levels in Solid Forms

Residual solvents are volatile organic compounds used or created during the manufacture of a compound. Regulations, including regulations issued by the U.S. Food and Drug Administration, require compounds intended for use as active pharmaceutical ingredients to be substantially free of toxicologically significant residual solvents. Typically, headspace gas chromatography is employed to determine residual solvent levels, often in combination with mass spectrometry to identify and quantify specific residual solvents.

In some embodiments, the total level of residual solvents in a solid form of the present disclosure is less than 1%. In some embodiments, the total level of residual solvents in a solid form of the present disclosure is less than 0.9%. In some embodiments, the total level of residual solvents in a solid form of the present disclosure is less than 0.8%. In some embodiments, the total level of residual solvents in a solid form of the present disclosure is less than 0.7%. In some embodiments, the total level of residual solvents in a solid form of the present disclosure is less than 0.6%. In some embodiments, the total level of residual solvents in a solid form of the present disclosure is less than 0.5%. In some embodiments, the total level of residual solvents in a solid form of the present disclosure is less than 0.4%. In some embodiments, the total level of residual solvents in a solid form of the present disclosure is less than 0.3%. In some embodiments, the total level of residual solvents in a solid form of the present disclosure is less than 0.2%. In some embodiments, the total level of residual solvents in a solid form of the present disclosure is less than 0.1%.

In some embodiments, there is no detectable residual solvent in a solid form of the present disclosure.

In some embodiments, the residual methanol level in a solid form of the present disclosure is less than 3000 ppm. In some embodiments, the residual methanol level in a solid form of the present disclosure is less than 2500 ppm. In some embodiments, the residual methanol level in a solid form of the present disclosure is less than 2000 ppm. In some embodiments, the residual methanol level in a solid form of the present disclosure is less than 1500 ppm. In some embodiments, the residual methanol level in a solid form of the present disclosure is less than 1000 ppm. In some embodiments, the residual methanol level in a solid form of the present disclosure is less than 900 ppm. In some embodiments, the residual methanol level in a solid form of the present disclosure is less than 800 ppm. In some embodiments, the residual methanol level in a solid form of the present disclosure is less than 700 ppm. In some embodiments, the residual methanol level in a solid form of the present disclosure is less than 600 ppm. In some embodiments, the residual methanol level in a solid form of the present disclosure is less than 500 ppm. In some embodiments, the residual methanol level in a solid form of the present disclosure is less than 400 ppm. In some embodiments, the residual methanol level in a solid form of the present disclosure is less than 300 ppm. In some embodiments, the residual methanol level in a solid form of the present disclosure is less than 200 ppm. In some embodiments, the residual methanol level in a solid form of the present disclosure is less than 100 ppm. In some embodiments, there is no detectable residual methanol in a solid form of the present disclosure.

In some embodiments, the residual isopropyl acetate level in a solid form of the present disclosure is less than 5000 ppm. In some embodiments, the residual isopropyl acetate level in a solid form of the present disclosure is less than 4500 ppm. In some embodiments, the residual isopropyl acetate level in a solid form of the present disclosure is less than 4000 ppm. In some embodiments, the residual isopropyl acetate level in a solid form of the present disclosure is less than 3500 ppm. In some embodiments, the residual isopropyl acetate level in a solid form of the present disclosure is less than 3000 ppm. In some embodiments, the residual isopropyl acetate level in a solid form of the present disclosure is less than 2500 ppm. In some embodiments, the residual isopropyl acetate level in a solid form of the present disclosure is less than 2000 ppm. In some embodiments, the residual isopropyl acetate level in a solid form of the present disclosure is less than 1500 ppm. In some embodiments, the residual isopropyl acetate level in a solid form of the present disclosure is less than 1000 ppm. In some embodiments, the residual isopropyl acetate level in a solid form of the present disclosure is less than 900 ppm. In some embodiments, the residual isopropyl acetate level in a solid form of the present disclosure is less than 800 ppm. In some embodiments, the residual isopropyl acetate level in a solid form of the present disclosure is less than 700 ppm. In some embodiments, the residual isopropyl acetate level in a solid form of the present disclosure is less than 600 ppm. In some embodiments, the residual isopropyl acetate level in a solid form of the present disclosure is less than 500 ppm. In some embodiments, the residual isopropyl acetate level in a solid form of the present disclosure is less than 400 ppm. In some embodiments, the residual isopropyl acetate level in a solid form of the present disclosure is less than 300 ppm. In some embodiments, the residual isopropyl acetate level in a solid form of the present disclosure is less than 200 ppm. In some embodiments, the residual isopropyl acetate level in a solid form of the present disclosure is less than 100 ppm. In some embodiments, there is no detectable residual isopropyl acetate in a solid form of the present disclosure.

In some embodiments, the residual heptane level in a solid form of the present disclosure is less than 5000 ppm. In some embodiments, the residual heptane level in a solid form of the present disclosure is less than 4500 ppm. In some embodiments, the residual heptane level in a solid form of the present disclosure is less than 4000 ppm. In some embodiments, the residual heptane level in a solid form of the present disclosure is less than 3500 ppm. In some embodiments, the residual heptane level in a solid form of the present disclosure is less than 3000 ppm. In some embodiments, the residual heptane level in a solid form of the present disclosure is less than 2500 ppm. In some embodiments, the residual heptane level in a solid form of the present disclosure is less than 2000 ppm. In some embodiments, the residual heptane level in a solid form of the present disclosure is less than 1500 ppm. In some embodiments, the residual heptane level in a solid form of the present disclosure is less than 1000 ppm. In some embodiments, the residual heptane level in a solid form of the present disclosure is less than 900 ppm. In some embodiments, the residual heptane level in a solid form of the present disclosure is less than 800 ppm. In some embodiments, the residual heptane level in a solid form of the present disclosure is less than 700 ppm. In some embodiments, the residual heptane level in a solid form of the present disclosure is less than 600 ppm. In some embodiments, the residual heptane level in a solid form of the present disclosure is less than 500 ppm. In some embodiments, the residual heptane level in a solid form of the present disclosure is less than 400 ppm. In some embodiments, the residual heptane level in a solid form of the present disclosure is less than 300 ppm. In some embodiments, the residual heptane level in a solid form of the present disclosure is less than 200 ppm. In some embodiments, the residual heptane level in a solid form of the present disclosure is less than 100 ppm. In some embodiments, there is no detectable residual heptane in a solid form of the present disclosure.

In some embodiments, the residual methanol level in a solid form of the present disclosure is less than 3000 ppm, the residual isopropyl acetate level in the solid form is less than 5000 ppm, and the residual heptane level in the solid form is less than 5000 ppm.

In some embodiments, the residual methanol level in a solid form of the present disclosure is less than 500 ppm, the residual isopropyl acetate level in the solid form is less than 4000 ppm, and the residual heptane level in the solid form is less than 500 ppm.

In some embodiments, the residual isopropyl acetate level in a solid form of the present disclosure is less than 5000 ppm, and the residual heptane level in the solid form is less than 5000 ppm. In some embodiments, the residual isopropyl acetate level in a solid form of the present disclosure is less than 5000 ppm, the residual heptane level in the solid form is less than 5000 ppm, and there is no detectable residual methanol in the solid form.

In some embodiments, the residual isopropyl acetate level in a solid form of the present disclosure is less than 500 ppm, and the residual heptane level in the solid form is less than 500 ppm. In some embodiments, the residual isopropyl acetate level in a solid form of the present disclosure is less than 500 ppm, the residual heptane level in the solid form is less than 500 ppm, and there is no detectable residual methanol in the solid form.

In some embodiments, solid forms of the present disclosure comprise residual solvent levels within the limits specified in the ICH guidelines.

In some embodiments, solid forms of the present disclosure comprise class 1 residual solvent levels within the limits specified in the ICH guidelines. In some embodiments, the total level of class 1 residual solvents in the solid form is less than 1%. In some embodiments, the total level of class 1 residual solvents in the solid form is less than 0.9%. In some embodiments, the total level of class 1 residual solvents in the solid form is less than 0.8%. In some embodiments, the total level of class 1 residual solvents in the solid form is less than 0.7%. In some embodiments, the total level of class 1 residual solvents in the solid form is less than 0.6%. In some embodiments, the total level of class 1 residual solvents in the solid form is less than 0.5%. In some embodiments, the total level of class 1 residual solvents in the solid form is less than 0.4%. In some embodiments, the total level of class 1 residual solvents in the solid form is less than 0.3%. In some embodiments, the total level of class 1 residual solvents in the solid form is less than 0.2%. In some embodiments, the total level of class 1 residual solvents in the solid form is less than 0.1%. In some embodiments, the total level of class 1 residual solvents in the solid form is less than 0.05%. In some embodiments, the total level of class 1 residual solvents in the solid form is less than 0.0025%. In some embodiments, there is no detectable class 1 residual solvent in a solid form of the present disclosure.

In some embodiments, solid forms of the present disclosure comprise class 2 residual solvent levels within the limits specified in the ICH guidelines. In some embodiments, the total level of class 2 residual solvents in the solid form is less than 1%. In some embodiments, the total level of class 2 residual solvents in the solid form is less than 0.9%. In some embodiments, the total level of class 2 residual solvents in the solid form is less than 0.8%. In some embodiments, the total level of class 2 residual solvents in the solid form is less than 0.7%. In some embodiments, the total level of class 2 residual solvents in the solid form is less than 0.6%. In some embodiments, the total level of class 2 residual solvents in the solid form is less than 0.5%. In some embodiments, the total level of class 2 residual solvents in the solid form is less than 0.4%. In some embodiments, the total level of class 2 residual solvents in the solid form is less than 0.3%. In some embodiments, the total level of class 2 residual solvents in the solid form is less than 0.2%. In some embodiments, the total level of class 2 residual solvents in the solid form is less than 0.1%. In some embodiments, the total level of class 2 residual solvents in the solid form is less than 0.05%. In some embodiments, the total level of class 2 residual solvents in the solid form is less than 0.0025%. In some embodiments, there is no detectable class 2 residual solvent in a solid form of the present disclosure.

Substantially Pure Solid Forms

Solid forms intended for use as APIs in therapeutic compositions should be substantially pure. Specifically, substantially pure forms are free from reaction impurities, starting materials, reagents, side products, unwanted solvents, and other processing impurities arising from the preparation and/or isolation and/or purification of the solid form.

In some embodiments, a solid form of the present disclosure is more than 70% by weight Compound (I). In some embodiments, a solid form of the present disclosure is more than 75% by weight Compound (I). In some embodiments, a solid form of the present disclosure is more than 80% by weight Compound (I). In some embodiments, a solid form of the present disclosure is more than 85% by weight Compound (I). In some embodiments, a solid form of the present disclosure is more than 90% by weight Compound (I). In some embodiments, a solid form of the present disclosure is more than 95% by weight Compound (I). In some embodiments, a solid form of the present disclosure is more than 97% by weight Compound (I). In some embodiments, a solid form of the present disclosure is more than 98% by weight Compound (I). In some embodiments, a solid form of the present disclosure is more than 99% by weight Compound (I). In some embodiments, a solid form of the present disclosure is more than 99.5% by weight Compound (I).

In some embodiments, a solid form of the present disclosure is substantially free of degradation products. In some embodiments, degradation products comprise less than 5% by weight of a solid form of the present disclosure. In some embodiments, degradation products comprise less than 4% by weight of a solid form of the present disclosure. In some embodiments, degradation products comprise less than 3% by weight of a solid form of the present disclosure. In some embodiments, degradation products comprise less than 2% by weight of a solid form of the present disclosure. In some embodiments, degradation products comprise less than 1% by weight of a solid form of the present disclosure. In some embodiments, degradation products comprise less than 0.5% by weight of a solid form of the present disclosure. In some embodiments, degradation products comprise less than 0.25% by weight of a solid form of the present disclosure. In some embodiments, degradation products comprise less than 0.1% by weight of a solid form of the present disclosure. In some embodiments, degradation products comprise less than 0.05% by weight of a solid form of the present disclosure.

In some embodiments, a solid form of the present disclosure is substantially free of dimers of Compound (I). In some embodiments, dimers of Compound (I) comprise less than 5% by weight of a solid form of the present disclosure. In some embodiments, dimers of Compound (I) comprise less than 4% by weight of a solid form of the present disclosure. In some embodiments, dimers of Compound (I) comprise less than 3% by weight of a solid form of the present disclosure. In some embodiments, dimers of Compound (I) comprise less than 2% by weight of a solid form of the present disclosure. In some embodiments, dimers of Compound (I) comprise less than 1% by weight of a solid form of the present disclosure. In some embodiments, dimers of Compound (I) comprise less than 0.5% by weight of a solid form of the present disclosure. In some embodiments, dimers of Compound (I) comprise less than 0.25% by weight of a solid form of the present disclosure. In some embodiments, dimers of Compound (I) comprise less than 0.1% by weight of a solid form of the present disclosure. In some embodiments, dimers of Compound (I) comprise less than 0.05% by weight of a solid form of the present disclosure.

Substantially Amorphous Solid Forms

In some embodiments, a solid form of the present disclosure is substantially amorphous. As determined by XRPD, an API could exhibit identical broad peaks and halos (i.e., that it appears to be an identical amorphous solid); however, how an amorphous solid is formed (e.g., by spray drying or different precipitation process) can impart different material attributes to the API (e.g., density, flowability, particle morphology and particle size distribution). These material attributes determine how the API interact with excipients in oral dosage formulations (e.g., capsules and tablets) during processing, and consequently may result in different dissolution profiles and different pharmacokinetic profiles. Illustratively, an amorphous solid form with relatively higher glass transition temperature ($T_g$) may provide better physical stability than an amorphous solid form with substantially identical XRPD halos and a lower $T_g$.

In some embodiments, a solid form of the present disclosure is characterized by less than 15% crystallinity. In some embodiments, a solid form of the present disclosure is characterized by less than 14% crystallinity. In some embodiments, a solid form of the present disclosure is characterized by less than 13% crystallinity. In some embodiments, a solid form of the present disclosure is characterized by less than 12% crystallinity. In some embodiments, a solid form of the present disclosure is characterized by less than 11% crystallinity. In some embodiments, a solid form of the present disclosure is characterized by less than 10% crystallinity. In some embodiments, a solid form of the present disclosure is characterized by less than 9% crystallinity. In some embodiments, a solid form of the present disclosure is characterized by less than 8% crystallinity. In some embodiments, a solid form of the present disclosure is characterized by less than 7% crystallinity. In some embodiments, a solid form of the present disclosure is characterized by less than 6% crystallinity. In some embodiments, a solid form of the present disclosure is characterized by less than 5% crystallinity. In some embodiments, a solid form of the present disclosure is characterized by less than 4% crystallinity. In some embodiments, a solid form of the present disclosure is characterized by less than 3% crystallinity. In some embodiments, a solid form of the present disclosure is characterized by less than 2% crystallinity. In some embodiments, a solid form of the present disclosure is characterized by less than 1% crystallinity.

Spray Drying Processes for Preparing Solid Forms of Compound (I)

In some embodiments, the present disclosure provides a process for preparing a solid form of Compound (I) described herein comprising spray drying a solution of Compound (I).

In some embodiments, the present disclosure provides a process for preparing an amorphous form of Compound (I) comprising: washing a solution of Compound (I) with a first aqueous acidic solution to create a first solution comprising a first organic layer and a first aqueous layer, wherein the solution of Compound (I) comprises a first organic solvent; removing the first aqueous layer; and performing a solvent exchange from the first organic solvent to a second organic solvent.

In some embodiments, removing the first aqueous layer removes basic impurities that are more soluble than Compound (I). In some embodiments, removing the first aqueous layer removes basic impurities that are more polar than Compound (I). In some embodiments, the basic impurities comprise at least one of (R)-3-(2-fluoro-4-phenoxyphenyl)-1-(piperidin-3-yl)-1H-pyrazolo[3,4-d]pyrimidin-4-amine, having the following structure:

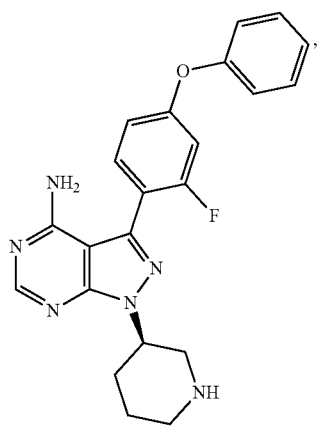 [SMILES: Nc1ncnc2c1c(-c1ccc(Oc3ccccc3)cc1F)nn2[C@@H]1CCCNC1]

or a pharmaceutically acceptable salt thereof;

2-methyl-2-(4-(oxetan-3-yl)piperazin-1-yl)propanal, having the following structure:

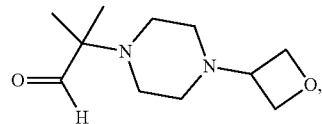

or a pharmaceutically acceptable salt thereof;
pyrrolidine; or
2-((R)-3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)-3-(pyrrolidin-1-yl)pentanenitrile, having the following structure:

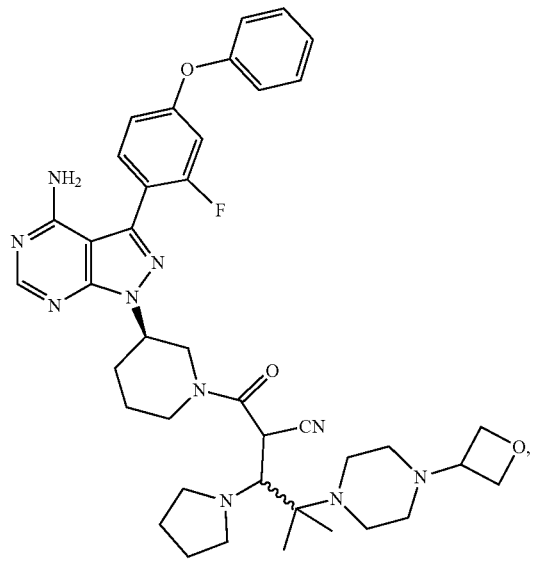 [SMILES: CC(C)(C(C(C#N)C(=O)N1CCC[C@@H](n2nc(-c3ccc(Oc4ccccc4)cc3F)c3c(N)ncnc32)C1)N1CCCC1)N1CCN(C2COC2)CC1]

or a pharmaceutically acceptable salt thereof.

In some embodiments, the first aqueous acidic solution has a pH between 1 and 6. In some embodiments, the first aqueous acidic solution has a pH between 2.5 and 3.5. In some embodiments, the first aqueous acidic solution is a pH 3 phosphate buffer.

In some embodiments, the first organic solvent comprises at least one water-immiscible organic solvent. In some embodiments, the at least one water-immiscible organic solvent is chosen from dichloromethane, ethyl acetate, carbon tetrachloride, chloroform, diethyl ether, di-isopropyl ether, methyl tetrahydrofuran, and isopropyl acetate. In some embodiments, the first organic solvent comprises dichloromethane.

In some embodiments, the second organic solvent comprises at least one of alkyl acetate, methyl tetrahydrofuran, toluene, methyl cyclopentyl ether, methyl tert-butyl ether, pentanone, acetone, acetonitrile and alkyl propionate. In some embodiments, the alkyl acetate is isopropyl acetate. In some embodiments, the second organic solvent comprises isopropyl acetate.

In some embodiments, performing a solvent exchange from the first organic solvent to a second organic solvent removes at least 50% of the first organic solvent. In some embodiments, performing a solvent exchange from the first organic solvent to a second organic solvent removes at least 60% of the first organic solvent. In some embodiments, performing a solvent exchange from the first organic solvent to a second organic solvent removes at least 70% of the first organic solvent.

In some embodiments, the process further comprises washing the first organic layer with a second aqueous acidic solution to create a second solution comprising a second organic layer and a second aqueous layer, wherein the second aqueous layer comprises Compound (I); and removing the second organic layer.

In some embodiments, removing the second organic layer removes impurities with lower aqueous solubilities than Compound (I). In some embodiments, removing the second organic layer removes impurities that are less polar than Compound (I).

In some embodiments, the impurities removed with the second organic layer comprise at least one of: one of (R)-3-(3-(4-amino-3-(2-fluoro-4-phenoxyphenyl)-1H-pyrazolo[3,4-d]pyrimidin-1-yl)piperidin-1-yl)-3-oxopropanenitrile, having the following structure:

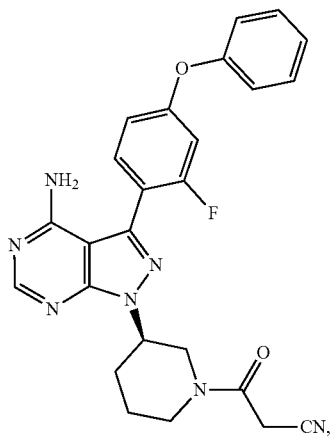 [SMILES: N#CCC(=O)N1CCC[C@@H](n2nc(-c3ccc(Oc4ccccc4)cc3F)c3c(N)ncnc32)C1]

or a pharmaceutically acceptable salt thereof; or hexamethyldisiloxane.

In some embodiments, the second aqueous acidic solution has a pH between 1 and 6. In some embodiments, the second aqueous acidic solution has a pH between 2.5 and 3.5. In some embodiments, the second aqueous acidic solution is a pH 3 phosphate buffer.

In some embodiments, the process further comprises adding a first base to the second aqueous layer to create a third solution comprising a third organic layer and a third aqueous layer, wherein the third organic layer comprises Compound (I); extracting the third aqueous layer using a third organic solvent; and concentrating the third organic layer.

In some embodiments, the first base is an aqueous base. In some embodiments, the aqueous base has a pH between 8 and 14. In some embodiments, the first base is aqueous potassium hydroxide.

In some embodiments, the third organic solvent comprises at least one of alkyl acetate, methyl tetrahydrofuran, toluene, methyl cyclopentyl ether, methyl tert-butyl ether, pentanone, acetone, acetonitrile and alkyl propionate. In some embodiments, the alkyl acetate is isopropyl acetate. In some embodiments, the third organic solvent comprises isopropyl acetate.

In some embodiments, the process further comprises adding an antisolvent to the third organic layer to create a precipitate comprising Compound (I). In some embodiments, the antisolvent comprises at least one of hexanes, heptanes, and octanes. In some embodiments, the antisolvent is n-hexane. In some embodiments, the antisolvent is n-heptane. In some embodiments, the antisolvent is n-octane.

In some embodiments, the antisolvent is added at a temperature between −10° C. and 10° C.

In some embodiments, the process further comprises isolating the precipitate comprising Compound (I). In some embodiments, isolating the precipitate comprising Compound (I) comprises drying the precipitate comprising Compound (I). In some embodiments, drying comprises air drying, blow drying, or vacuum-drying.

In some embodiments, the process further comprises dissolving the precipitate comprising Compound (I) in a fourth organic solvent to create a fourth solution; and spray drying the fourth solution to obtain a solid form of Compound (I).

In some embodiments, the fourth organic solvent comprises at least one of methanol, ethanol, acetone, acetonitrile, and methyl ethyl ketone. In some embodiments, the fourth organic solvent comprises methanol.

In some embodiments, the spray drying process utilizes at least one of the parameters listed in Table 1 below.

TABLE 1

| Spray Drying Parameters | | | | | | |
|---|---|---|---|---|---|---|
| Process Stage | | System Gas Flow (g/min) | Dryer Inlet Temp (° C.) | Dryer Outlet Temp (° C.) | Feed Pressure (psig) | Feed Rate (g/min) |
| Preheat | Target | 1850 | 140 | | | |
| | Range | 1550-2150 | 125-155 | | | |
| Warm-up | Target | 1850 | 140 | 53 | 250 | 90 |
| | Range | 1550-2150 | 125-155 | 48-58 | 150-350 | 70-110 |
| Solution | Target | 1850 | 140 | 53 | 265 | 100 |
| | Range | 1550-2150 | 125-155 | 48-58 | 165-365 | 80-120 |
| Shut Down | Target | 1850 | 140 | 53 | 250 | 90 |
| | Range | 1550-2150 | 125-155 | 48-58 | 150-350 | 70-110 |

In some embodiments, spray drying the fourth solution comprises passing the fourth solution through a spray drying chamber having an inlet temperature of 90° C. to 180° C. In some embodiments, the spray drying chamber has an inlet temperature of 125° C. to 155° C.

In some embodiments, spray drying the fourth solution comprises passing the fourth solution through a spray drying chamber having an outlet temperature of 25° C. to 80° C. In some embodiments, the spray drying chamber has an outlet temperature of 45° C. to 60° C.

In some embodiments, the process provides a stable solid form of Compound (I). In some embodiments, the process provides a solid form of Compound (I) characterized by a mass loss of less than 5 wt. % between 20° C. and 240° C. by thermogravimetric analysis. In some embodiments, the process provides a solid form of Compound (I) characterized by a mass loss of less than 3 wt. % between 20° C. and 240° C. by thermogravimetric analysis. In some embodiments, the process provides a solid form of Compound (I) characterized by a mass loss of less than 2 wt. % between 20° C. and 240° C. by thermogravimetric analysis. In some embodiments, the process provides a solid form of Compound (I) characterized by a mass loss of less than 1.5 wt. % between 20° C. and 240° C. by thermogravimetric analysis.

In some embodiments, the process provides a stable solid form of Compound (I) characterized by a glass transition temperature ($T_g$) greater than 90° C. at 0% relative humidity.

In some embodiments, the process provides fine particles of Compound (I). In some embodiments, the process provides a solid form of Compound (I) characterized by a wet particle size distribution having a $D_{10}$ value less than 10 μm. In some embodiments, the process provides a solid form of Compound (I) characterized by a wet particle size distribution having a $D_{10}$ value less than 10 μm and a $D_{50}$ value less than 100 μm. In some embodiments, the process provides a solid form of Compound (I) characterized by a wet particle size distribution having a $D_{10}$ value less than 10 μm and a $D_{90}$ value less than 200 μm. In some embodiments, the process provides a solid form of Compound (I) characterized by a wet particle size distribution having a $D_{10}$ value less than 10 μm, a $D_{50}$ value less than 100 μm, and a $D_{90}$ value less than 200 μm.

In some embodiments, the process provides a solid form of Compound (I) characterized by a wet particle size distribution having a $D_{10}$ value between 5 μm and 6 μm. In some embodiments, the process provides a solid form of Compound (I) characterized by a wet particle size distribution having a $D_{50}$ value between 10 μm and 20 μm. In some embodiments, the process provides a solid form of Compound (I) characterized by a wet particle size distribution having a $D_{90}$ value between 10 μm and 50 μm.

In some embodiments, the process provides a solid form of Compound (I) characterized by a wet particle size distribution having a $D_{10}$ value between 5 μm and 6 μm and a $D_{50}$ value between 10 μm and 20 μm. In some embodiments, the process provides a solid form of Compound (I) characterized by a wet particle size distribution having a $D_{10}$ value between 5 μm and 6 μm and a $D_{90}$ value between 10 μm and 50 μm. In some embodiments, the process provides a solid form of Compound (I) characterized by a wet particle size distribution having a $D_{50}$ value between 10 μm and 20 μm and a $D_{90}$ value between 10 μm and 50 μm.

In some embodiments, a solid form of the present disclosure is characterized by a wet particle size distribution having a $D_{10}$ value between 5 μm and 6 μm, a $D_{50}$ value between 10 μm and 20 μm, and a $D_{90}$ value between 10 μm and 50 μm.

In some embodiments, the process provides a solid form of Compound (I) characterized by a particle size distribution as described above and a mean bulk density less than 0.3 g/cc. In some embodiments, the process provides a solid form of Compound (I) characterized by a particle size distribution as described above and a mean tapped density less than 0.3 g/cc.

In some embodiments, the process provides a solid form of Compound (I) that is substantially free of degradation products. In some embodiments, the process provides a solid form of Compound (I) that is substantially free of dimers of Compound (I). In some embodiments, the process provides a solid form of Compound (I) that is substantially free of dimers of Compound (I) having the following structure:

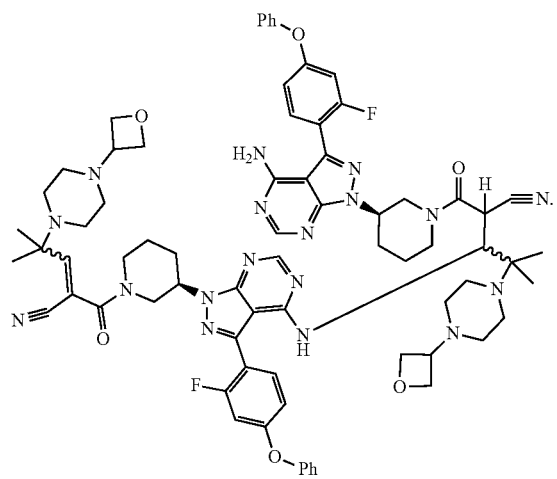 [SMILES: CC(C)(C=C(C#N)C(=O)N1CCC[C@@H](n2nc(-c3ccc(Oc4ccccc4)cc3F)c3c(NC(C(C#N)C(=O)N4CCC[C@@H](n5nc(-c6ccc(Oc7ccccc7)cc6F)c6c(N)ncnc65)C4)C(C)(C)N4CCN(C5COC5)CC4)ncnc32)C1)N1CCN(C2COC2)CC1]

In some embodiments, the process provides a solid form of Compound (I), wherein residual solvents comprise less than 1% of the solid form of Compound (I). In some embodiments, the process provides a solid form of Compound (I), wherein there is no detectable residual solvent in the solid form. In some embodiments, the process provides a solid form of Compound (I), wherein: the residual methanol level is less than 3000 ppm; the residual isopropyl acetate level is less than 5000 ppm; and/or the residual heptane level is less than 5000 ppm. In some embodiments, the process provides a solid form of Compound (I), wherein: the residual methanol level is less than 500 ppm; the residual isopropyl acetate level is less than 4000 ppm; and/or the residual heptane level is less than 500 ppm.

In some embodiments, the process provides a solid form of Compound (I), wherein the residual dichloromethane level is less than 1500 ppm. In some embodiments, the process provides a solid form of Compound (I), wherein the residual dichloromethane level is less than 1000 ppm. In some embodiments, the process provides a solid form of Compound (I), wherein the residual dichloromethane level is less than 500 ppm. In some embodiments, the process provides a solid form of Compound (I), wherein the residual dichloromethane level is less than 100 ppm.

In some embodiments, the process provides a substantially amorphous solid form of Compound (I).

In some embodiments, the process further comprises micronizing the solid form of Compound (I).

Precipitation Processes for Preparing Solid Forms of Compound (I)

In some embodiments, the disclosure provides a process for preparing a solid form of Compound (I) comprising adding a base to an aqueous solution comprising Compound (I). In some embodiments, the base is an aqueous base. In some embodiments, the base is aqueous potassium hydroxide.

In some embodiments, the disclosure provides a process for preparing a solid form of Compound (I) comprising washing a solution of Compound (I) with a first aqueous acidic solution to create a first solution comprising a first organic layer and a first aqueous layer, wherein the solution of Compound (I) comprises a first organic solvent; and removing the first aqueous layer.

In some embodiments, the first aqueous acidic solution has a pH between 1 and 6. In some embodiments, the first aqueous acidic solution has a pH between 2.5 and 3.5. In some embodiments, the first aqueous acidic solution is a pH 3 phosphate buffer.

In some embodiments, the first organic solvent comprises at least one water-immiscible organic solvent. In some embodiments, the at least one water-immiscible organic solvent is chosen from dichloromethane, ethyl acetate, carbon tetrachloride, chloroform, diethyl ether, di-isopropyl ether, methyl tetrahydrofuran, and isopropyl acetate. In some embodiments, the first organic solvent is dichloromethane.

In some embodiments, removing the first aqueous layer removes basic impurities that are more soluble than Compound (I). In some embodiments, removing the first aqueous layer removes basic impurities that are more polar than Compound (I). In some embodiments, the basic impurities comprise at least one of (R)-3-(2-fluoro-4-phenoxyphenyl)-1-(piperidin-3-yl)-1H-pyrazolo[3,4-d]pyrimidin-4-amine, having the following structure:

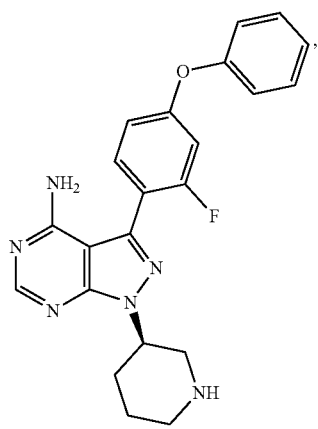 [SMILES: Nc1ncnc2c1c(-c1ccc(Oc3ccccc3)cc1F)nn2[C@@H]1CCCNC1]

or a pharmaceutically acceptable salt thereof;

2-methyl-2-(4-(oxetan-3-yl)piperazin-1-yl)propanal, having the following structure:

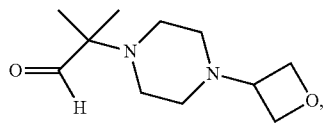

or a pharmaceutically acceptable salt thereof;
pyrrolidine; or
2-((R)-3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)-3-(pyrrolidin-1-yl)pentanenitrile, having the following structure:

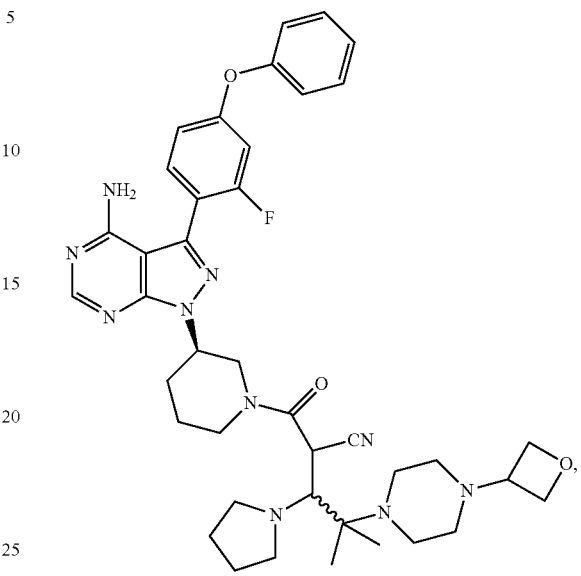

or a pharmaceutically acceptable salt thereof.

In some embodiments, the process further comprises: partially removing the first organic solvent from the first organic layer; adding a second organic solvent to the first organic layer, wherein the first organic solvent and the second organic solvent are not the same; and adding a second aqueous acidic solution to create a second solution comprising a second organic layer and a second aqueous layer, wherein the second aqueous layer comprises Compound (I). In some embodiments, partially removing the first organic solvent from the first organic layer comprises distillation under reduced pressure. In some embodiments, the second organic solvent is isopropyl acetate.

In some embodiments, the process further comprises: removing the second organic layer; removing residual organic solvent in the second aqueous layer to create an aqueous solution of Compound (I); and adding a second base to the aqueous solution of Compound (I) to create a precipitate comprising Compound (I). In some embodiments, removing residual organic solvent in the second aqueous phase comprises distillation under reduced pressure.

In some embodiments, removing the second organic layer removes impurities with lower aqueous solubilities than Compound (I). In some embodiments, removing the second organic layer removes impurities that are less polar than Compound (I).

In some embodiments, the impurities removed with the second organic layer comprise at least one of: one of (R)-3-(3-(4-amino-3-(2-fluoro-4-phenoxyphenyl)-1H-pyrazolo[3,4-d]pyrimidin-1-yl)piperidin-1-yl)-3-oxopropanenitrile, having the following structure:

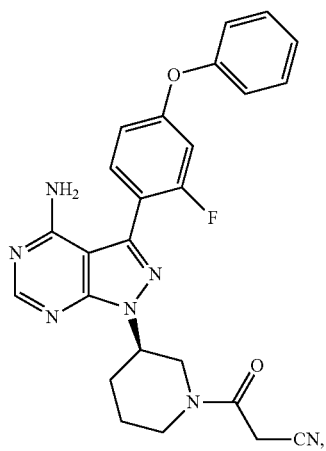 [SMILES: N#CCC(=O)N1CCC[C@@H](n2nc(-c3ccc(Oc4ccccc4)cc3F)c3c(N)ncnc32)C1]

or a pharmaceutically acceptable salt thereof, or hexamethyldisiloxane.

In some embodiments, the second base is an aqueous base. In some embodiments, the second base is aqueous potassium hydroxide.

In some embodiments, the process further comprises filtering and drying the precipitate.

In some embodiments, the process provides a solid form of Compound (I) that is substantially free of degradation products. In some embodiments, the process provides a solid form of Compound (I) that is substantially free of dimers of Compound (I). In some embodiments, the process provides a solid form of Compound (I) that is substantially free of dimers of Compound (I) having the following structure:

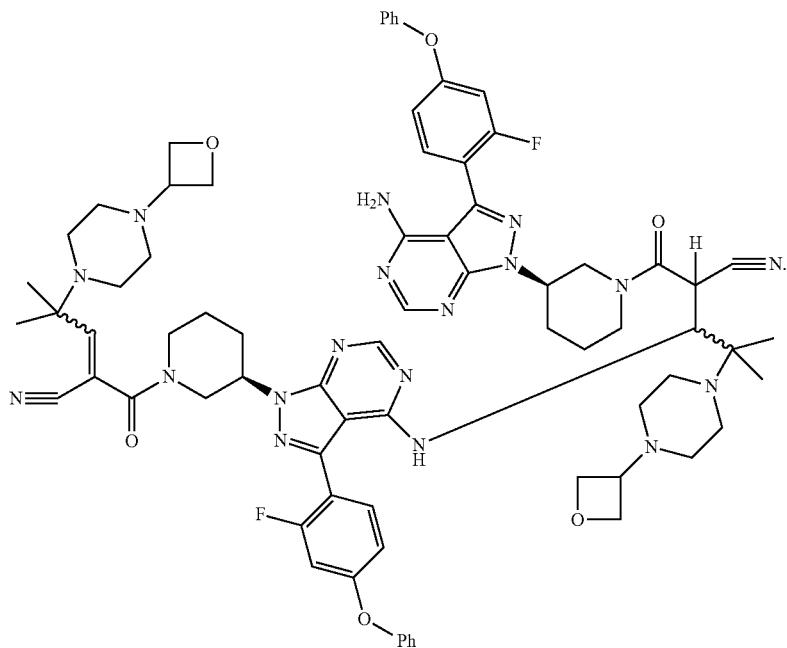 [SMILES: CC(C)(C=C(C#N)C(=O)N1CCC[C@@H](n2nc(-c3ccc(Oc4ccccc4)cc3F)c3c(NC(C(C#N)C(=O)N4CCC[C@@H](n5nc(-c6ccc(Oc7ccccc7)cc6F)c6c(N)ncnc65)C4)C(C)(C)N4CCN(C5COC5)CC4)ncnc32)C1)N1CCN(C2COC2)CC1]

In some embodiments, the process provides a solid form of Compound (I), wherein dimers of Compound (I) comprises less than 3.5% by weight of the solid form of Compound (I).

In some embodiments, the process provides a solid form of Compound (I), wherein residual solvents comprise less than 1% of the solid form of Compound (I). In some embodiments, the process provides a solid form of Compound (I), wherein residual solvents comprise less than 0.5% of the solid form of Compound (I). In some embodiments, the process provides a solid form of Compound (I), wherein there is no detectable residual solvent in the solid form. In some embodiments, the process provides a solid form of Compound (I), wherein the residual isopropyl acetate level is less than 5000 ppm; and/or the residual heptane level is less than 5000 ppm. In some embodiments, the process provides a solid form of Compound (I), wherein: the residual isopropyl acetate level is less than 500 ppm; and/or the residual heptane level is less than 500 ppm. In some embodiments, the process provides a solid form of Compound (I), wherein there is no detectable residual methanol in the solid form.

In some embodiments, the process provides a solid form of Compound (I), wherein the residual dichloromethane level is less than 1500 ppm. In some embodiments, the process provides a solid form of Compound (I), wherein the residual dichloromethane level is less than 1000 ppm. In some embodiments, the process provides a solid form of Compound (I), wherein the residual dichloromethane level is less than 500 ppm. In some embodiments, the process provides a solid form of Compound (I), wherein the residual dichloromethane level is less than 100 ppm.

In some embodiments, the process provides a solid form of Compound (I), characterized by a mean bulk density greater than 0.3 g/cc. In some embodiments, the process provides a solid form of Compound (I), characterized by a mean bulk density greater than 0.4 g/cc. In some embodiments, the process provides a solid form of Compound (I), characterized by a mean bulk density greater than 0.5 g/cc. In some embodiments, the process provides a solid form of Compound (I), characterized by a mean bulk density greater than 0.6 g/cc. In some embodiments, the process provides a solid form of Compound (I), characterized by a mean bulk density between than 0.6 g/cc and 0.7 g/cc.

In some embodiments, the process provides a solid form of Compound (I), characterized by a mean tapped density greater than 0.5 g/cc. In some embodiments, the process provides a solid form of Compound (I), characterized by a mean tapped density greater than 0.6 g/cc. In some embodiments, the process provides a solid form of Compound (I), characterized by a mean tapped density greater than 0.7 g/cc. In some embodiments, the process provides a solid form of Compound (I), characterized by a mean tapped density greater than 0.8 g/cc. In some embodiments, the process provides a solid form of Compound (I), characterized by a mean tapped density between than 0.7 g/cc and 0.9 g/cc.

In some embodiments, the process provides a solid form of Compound (I), characterized by a Hausner ratio less than or equal to 1.2.

In some embodiments, the process provides a solid form of Compound (I), characterized by characterized by a wet particle size distribution having a $D_{10}$ value greater than 70 µm. In some embodiments, the process provides a solid form of Compound (I), characterized by characterized by a wet particle size distribution having a $D_{50}$ value greater than 200 µm. In some embodiments, the process provides a solid form of Compound (I), characterized by characterized by a wet particle size distribution having a $D_{90}$ value greater than 400 µm. In some embodiments, the process provides a solid form of Compound (I), characterized by characterized by a wet particle size distribution having a $D_{10}$ value greater than 70 µm and a $D_{50}$ value greater than 200 µm. In some embodiments, the process provides a solid form of Compound (I), characterized by characterized by a wet particle size distribution having a $D_{10}$ value greater than 70 µm, a $D_{50}$ value greater than 200 µm, and a $D_{90}$ value greater than 400 µm. In some embodiments, the process provides a solid form of Compound (I), characterized by characterized by a wet particle size distribution having a $D_{10}$ value greater than 70 µm and a $D_{90}$ value greater than 400 µm. In some embodiments, the process provides a solid form of Compound (I), characterized by characterized by a wet particle size distribution having a $D_{50}$ value greater than 200 µm and a $D_{90}$ value greater than 400 µm.

In some embodiments, the process provides a solid form of Compound (I), characterized by a mass loss of less than 5 wt. % between 20° C. and 240° C. by thermogravimetric analysis. In some embodiments, the process provides a solid form of Compound (I), characterized by a mass loss of less than 4 wt. % between 20° C. and 240° C. by thermogravimetric analysis. In some embodiments, the process provides a solid form of Compound (I), characterized by a mass loss of less than 3 wt. % between 20° C. and 240° C. by thermogravimetric analysis. In some embodiments, the process provides a solid form of Compound (I), characterized by a mass loss of less than 2 wt. % between 20° C. and 240° C. by thermogravimetric analysis. In some embodiments, the process provides a solid form of Compound (I), characterized by a mass loss of less than 1.5 wt. % between 20° C. and 240° C. by thermogravimetric analysis.

In some embodiments, the process provides a solid form of Compound (I), characterized by a glass transition temperature ($T_g$) greater than 90° C. at 0% relative humidity.

In some embodiments, the process provides a substantially amorphous solid form of Compound (I).

In some embodiments, the process further comprises micronizing particles of Compound (I).

In some embodiments, the micronization process provides fine particles of Compound (I). In some embodiments, the micronization process provides a solid form of Compound (I) characterized by a wet particle size distribution having a $D_{10}$ value less than 10 µm. In some embodiments, the process provides a solid form of Compound (I) characterized by a wet particle size distribution having a $D_{10}$ value less than 10 µm and a $D_{50}$ value less than 100 µm. In some embodiments, the micronization process provides a solid form of Compound (I) characterized by a wet particle size distribution having a $D_{10}$ value less than 10 µm and a $D_{90}$ value less than 200 µm. In some embodiments, the micronization process provides a solid form of Compound (I) characterized by a wet particle size distribution having a $D_{10}$ value less than 10 µm, a $D_{50}$ value less than 100 µm, and a $D_{90}$ value less than 200 µm.

In some embodiments, the process provides a solid form of Compound (I) characterized by a wet particle size distribution having a $D_{10}$ value between 1 µm and 2 µm. In some embodiments, the process provides a solid form of Compound (I) characterized by a wet particle size distribution having a $D_{50}$ value between 40 µm and 70 µm. In some embodiments, the process provides a solid form of Compound (I) characterized by a wet particle size distribution having a $D_{90}$ value between 100 µm and 150 µm.

In some embodiments, the process provides a solid form of Compound (I) characterized by a wet particle size distribution having a $D_{10}$ value between 1 m and 2 µm and a $D_{50}$ value between 40 µm and 70 µm. In some embodiments, the process provides a solid form of Compound (I) characterized by a wet particle size distribution having a $D_{10}$ value between 1 µm and 2 µm and a $D_{90}$ value between 100 µm and 150 µm. In some embodiments, the process provides a solid form of Compound (I) characterized by a wet particle size distribution having a $D_{50}$ value between 40 µm and 70 µm and a $D_{90}$ value between 100 µm and 150 µm.

In some embodiments, a solid form of the present disclosure is characterized by a wet particle size distribution having a $D_{10}$ value between 1 µm and 2 µm, a $D_{50}$ value between 40 µm and 70 µm, and a $D_{90}$ value between 100 µm and 150 µm.

In some embodiments, the micronization process provides a stable solid form of Compound (I). In some embodiments, the micronization process provides a solid form of Compound (I) characterized by a mass loss of less than 5 wt. % between 20° C. and 240° C. by thermogravimetric analysis. In some embodiments, the micronization process provides a solid form of Compound (I) characterized by a mass loss of less than 3 wt. % between 20° C. and 240° C. by thermogravimetric analysis. In some embodiments, the micronization process provides a solid form of Compound (I) characterized by a mass loss of less than 2 wt. % between 20° C. and 240° C. by thermogravimetric analysis. In some embodiments, the micronization process provides a solid form of Compound (I) characterized by a mass loss of less than 1.5 wt. % between 20° C. and 240° C. by thermogravimetric analysis.

In some embodiments, the disclosure provides a process for preparing a solid form of Compound (I) comprising washing a solution of Compound (I) with a first aqueous acidic solution to create a first solution comprising a first organic layer and a first aqueous layer, wherein the solution of Compound (I) comprises a first organic solvent; and removing the first aqueous layer.

In some embodiments, the first aqueous acidic solution has a pH between 1 and 6. In some embodiments, the first aqueous acidic solution has a pH between 2.5 and 3.5. In some embodiments, the first aqueous acidic solution is a pH 3 phosphate buffer.

In some embodiments, the first organic solvent comprises at least one water-immiscible organic solvent. In some embodiments, the at least one water-immiscible organic solvent is chosen from dichloromethane, ethyl acetate, carbon tetrachloride, chloroform, diethyl ether, di-isopropyl ether, methyl tetrahydrofuran, and isopropyl acetate. In some embodiments, the first organic solvent is dichloromethane.

In some embodiments, removing the first aqueous layer removes basic impurities that are more soluble than Compound (I). In some embodiments, removing the first aqueous layer removes basic impurities that are more polar than Compound (I). In some embodiments, the basic impurities comprise at least one of (R)-3-(2-fluoro-4-phenoxyphenyl)-1-(piperidin-3-yl)-1H-pyrazolo[3,4-d]pyrimidin-4-amine, having the following structure:

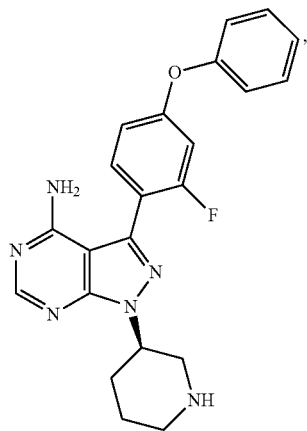

or a pharmaceutically acceptable salt thereof;
2-methyl-2-(4-(oxetan-3-yl)piperazin-1-yl)propanal, having the following structure:

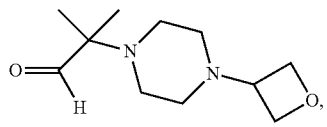

or a pharmaceutically acceptable salt thereof;
pyrrolidine; or
2-((R)-3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)-3-(pyrrolidin-1-yl)pentanenitrile, having the following structure:

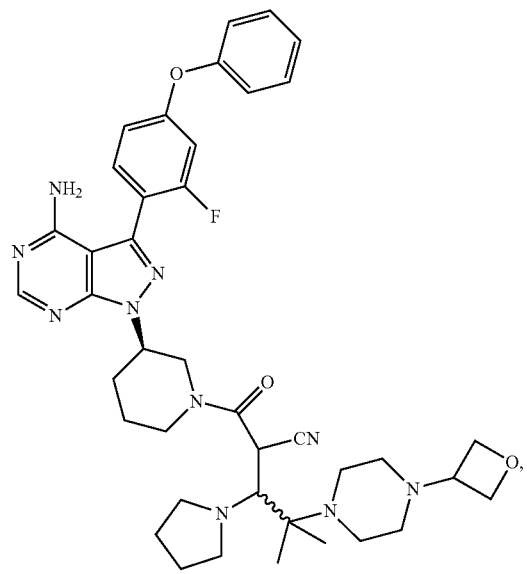 [SMILES: CC(C)(C(C(C#N)C(=O)N1CCC[C@@H](n2nc(-c3ccc(Oc4ccccc4)cc3F)c3c(N)ncnc32)C1)N1CCCC1)N1CCN(C2COC2)CC1]

or a pharmaceutically acceptable salt thereof.

In some embodiments, the process further comprises: adding a first organic acid to the first organic layer; concentrating the first organic layer to remove at least 70% of the first organic solvent; adding a third organic solvent to the first organic layer to create a third solution comprising a third organic layer and a third aqueous layer, wherein the third aqueous layer comprises Compound (I) and further wherein the first organic solvent and the third organic solvent are not the same; and adding a first base to adjust the pH of the third aqueous layer to between 2.5 and 3.5.

In some embodiments, the first organic acid is methanesulfonic acid.

In some embodiments, concentrating the first organic layer to remove at least 70% of the first organic solvent comprises distillation under reduced pressure.

In some embodiments, the third organic solvent is isopropyl acetate.

In some embodiments, the first base is an aqueous base. In some embodiments, the first base is aqueous potassium hydroxide.

In some embodiments, the process further comprises: removing the third organic layer; removing residual organic solvent in the third aqueous layer to create an aqueous solution of Compound (I); and adding a second base to the aqueous solution of Compound (I) to create a precipitate comprising Compound (I). In some embodiments, removing residual organic solvent in the third aqueous phase comprises distillation under reduced pressure.

In some embodiments, removing the third organic layer removes impurities with lower aqueous solubilities than Compound (I). In some embodiments, removing the third organic layer removes impurities that are less polar than Compound (I).

In some embodiments, the impurities removed with the third organic layer comprise at least one of: one of (R)-3-(3-(4-amino-3-(2-fluoro-4-phenoxyphenyl)-1H-pyrazolo[3,4-d]pyrimidin-1-yl)piperidin-1-yl)-3-oxopropanenitrile, having the following structure:

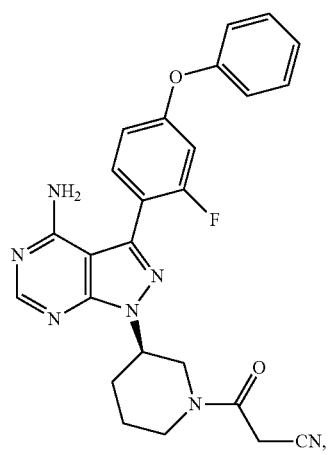 [SMILES: N#CCC(=O)N1CCC[C@@H](n2nc(-c3ccc(Oc4ccccc4)cc3F)c3c(N)ncnc32)C1]

or a pharmaceutically acceptable salt thereof; or hexamethyldisiloxane.

In some embodiments, the second base is an aqueous base. In some embodiments, the second base is aqueous potassium hydroxide.

In some embodiments, the process further comprises filtering and drying the precipitate.

In some embodiments, the process provides a solid form of Compound (I) that is substantially free of degradation products. In some embodiments, the process provides a solid form of Compound (I) that is substantially free of dimers of Compound (I). In some embodiments, the process provides a solid form of Compound (I) that is substantially free of dimers of Compound (I) having the following structure:

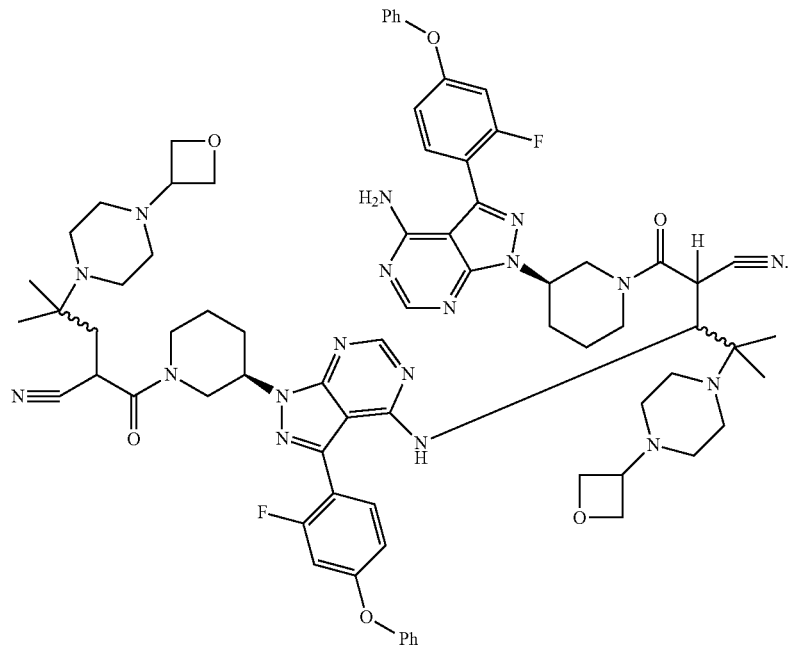 [SMILES: CC(C)(CC(C#N)C(=O)N1CCC[C@@H](n2nc(-c3ccc(Oc4ccccc4)cc3F)c3c(NC(C(C#N)C(=O)N4CCC[C@@H](n5nc(-c6ccc(Oc7ccccc7)cc6F)c6c(N)ncnc65)C4)C(C)(C)N4CCN(C5COC5)CC4)ncnc32)C1)N1CCN(C2COC2)CC1]

In some embodiments, the process provides a solid form of Compound (I), wherein dimers of Compound (I) comprises less than 3.5% by weight of the solid form of Compound (I).

In some embodiments, the process provides a solid form of Compound (I), wherein residual solvents comprise less than 1% of the solid form of Compound (I). In some embodiments, the process provides a solid form of Compound (I), wherein residual solvents comprise less than 0.5% of the solid form of Compound (I). In some embodiments, the process provides a solid form of Compound (I), wherein there is no detectable residual solvent in the solid form. In some embodiments, the process provides a solid form of Compound (I), wherein the residual isopropyl acetate level is less than 5000 ppm; and/or the residual heptane level is less than 5000 ppm. In some embodiments, the process provides a solid form of Compound (I), wherein: the residual isopropyl acetate level is less than 500 ppm; and/or the residual heptane level is less than 500 ppm. In some embodiments, the process provides a solid form of Compound (I), wherein there is no detectable residual methanol in the solid form.

In some embodiments, the process provides a solid form of Compound (I), wherein the residual dichloromethane level is less than 1500 ppm. In some embodiments, the process provides a solid form of Compound (I), wherein the residual dichloromethane level is less than 1000 ppm. In some embodiments, the process provides a solid form of Compound (I), wherein the residual dichloromethane level is less than 500 ppm. In some embodiments, the process provides a solid form of Compound (I), wherein the residual dichloromethane level is less than 100 ppm.

In some embodiments, the process provides a solid form of Compound (I), characterized by a mean bulk density greater than 0.3 g/cc. In some embodiments, the process provides a solid form of Compound (I), characterized by a mean bulk density greater than 0.4 g/cc. In some embodiments, the process provides a solid form of Compound (I), characterized by a mean bulk density greater than 0.5 g/cc. In some embodiments, the process provides a solid form of Compound (I), characterized by a mean bulk density greater than 0.6 g/cc. In some embodiments, the process provides a solid form of Compound (I), characterized by a mean bulk density between than 0.6 g/cc and 0.7 g/cc.

In some embodiments, the process provides a solid form of Compound (I), characterized by a mean tapped density greater than 0.5 g/cc. In some embodiments, the process provides a solid form of Compound (I), characterized by a mean tapped density greater than 0.6 g/cc. In some embodiments, the process provides a solid form of Compound (I), characterized by a mean tapped density greater than 0.7 g/cc. In some embodiments, the process provides a solid form of Compound (I), characterized by a mean tapped density greater than 0.8 g/cc. In some embodiments, the process provides a solid form of Compound (I), characterized by a mean tapped density between than 0.7 g/cc and 0.9 g/cc.

In some embodiments, the process provides a solid form of Compound (I), characterized by a Hausner ratio less than or equal to 1.2.

In some embodiments, the process provides a solid form of Compound (I), characterized by characterized by a wet particle size distribution having a $D_{10}$ value greater than 70 µm. In some embodiments, the process provides a solid form of Compound (I), characterized by characterized by a wet particle size distribution having a $D_{50}$ value greater than 200 µm. In some embodiments, the process provides a solid form of Compound (I), characterized by characterized by a wet particle size distribution having a $D_{90}$ value greater than 400 µm. In some embodiments, the process provides a solid form of Compound (I), characterized by characterized by a wet particle size distribution having a $D_{10}$ value greater than 70 µm and a $D_{50}$ value greater than 200 µm. In some embodiments, the process provides a solid form of Compound (I), characterized by characterized by a wet particle size distribution having a $D_{10}$ value greater than 70 µm, a $D_{50}$ value greater than 200 µm, and a $D_{90}$ value greater than 400 µm. In some embodiments, the process provides a solid form of Compound (I), characterized by characterized by a wet particle size distribution having a $D_{10}$ value greater than 70 µm and a $D_{90}$ value greater than 400 µm. In some embodiments, the process provides a solid form of Compound (I), characterized by characterized by a wet particle size distribution having a $D_{50}$ value greater than 200 µm and a $D_{90}$ value greater than 400 µm.

In some embodiments, the process provides a solid form of Compound (I), characterized by a mass loss of less than 5 wt. % between 20° C. and 240° C. by thermogravimetric analysis. In some embodiments, the process provides a solid form of Compound (I), characterized by a mass loss of less than 4 wt. % between 20° C. and 240° C. by thermogravimetric analysis. In some embodiments, the process provides a solid form of Compound (I), characterized by a mass loss of less than 3 wt. % between 20° C. and 240° C. by thermogravimetric analysis. In some embodiments, the process provides a solid form of Compound (I), characterized by a mass loss of less than 2 wt. % between 20° C. and 240° C. by thermogravimetric analysis. In some embodiments, the process provides a solid form of Compound (I), characterized by a mass loss of less than 1.5 wt. % between 20° C. and 240° C. by thermogravimetric analysis.

In some embodiments, the process provides a solid form of Compound (I), characterized by a glass transition temperature ($T_g$) greater than 90° C. at 0% relative humidity.

In some embodiments, the process provides a substantially amorphous solid form of Compound (I).

In some embodiments, the process further comprises micronizing particles of Compound (I).

In some embodiments, the micronization process provides fine particles of Compound (I). In some embodiments, the micronization process provides a solid form of Compound (I) characterized by a wet particle size distribution having a $D_{10}$ value less than 10 µm. In some embodiments, the process provides a solid form of Compound (I) characterized by a wet particle size distribution having a $D_{10}$ value less than 10 µm and a $D_{50}$ value less than 100 µm. In some embodiments, the micronization process provides a solid form of Compound (I) characterized by a wet particle size distribution having a $D_{10}$ value less than 10 µm and a $D_{90}$ value less than 200 µm. In some embodiments, the micronization process provides a solid form of Compound (I) characterized by a wet particle size distribution having a $D_{10}$ value less than 10 µm, a $D_{50}$ value less than 100 µm, and a $D_{90}$ value less than 200 µm.

In some embodiments, the process provides a solid form of Compound (I) characterized by a wet particle size distribution having a $D_{10}$ value between 1 µm and 2 µm. In some embodiments, the process provides a solid form of Compound (I) characterized by a wet particle size distribution having a $D_{50}$ value between 40 µm and 70 µm. In some embodiments, the process provides a solid form of Compound (I) characterized by a wet particle size distribution having a $D_{90}$ value between 100 µm and 150 µm.

In some embodiments, the process provides a solid form of Compound (I) characterized by a wet particle size distribution having a $D_{10}$ value between 1 m and 2 µm and a $D_{50}$ value between 40 µm and 70 µm. In some embodiments, the process provides a solid form of Compound (I) characterized by a wet particle size distribution having a $D_{10}$ value between 1 µm and 2 µm and a $D_{90}$ value between 100 µm and 150 µm. In some embodiments, the process provides a solid form of Compound (I) characterized by a wet particle size distribution having a $D_{50}$ value between 40 µm and 70 µm and a $D_{90}$ value between 100 µm and 150 µm.

In some embodiments, a solid form of the present disclosure is characterized by a wet particle size distribution having a $D_{10}$ value between 1 m and 2 µm, a $D_{50}$ value between 40 µm and 70 µm, and a $D_{90}$ value between 100 µm and 150 µm.

In some embodiments, the micronization process provides a stable solid form of Compound (I). In some embodiments, the micronization process provides a solid form of Compound (I) characterized by a mass loss of less than 5 wt. % between 20° C. and 240° C. by thermogravimetric analysis. In some embodiments, the micronization process provides a solid form of Compound (I) characterized by a mass loss of less than 3 wt. % between 20° C. and 240° C. by thermogravimetric analysis. In some embodiments, the micronization process provides a solid form of Compound (I) characterized by a mass loss of less than 2 wt. % between 20° C. and 240° C. by thermogravimetric analysis. In some embodiments, the micronization process provides a solid form of Compound (I) characterized by a mass loss of less than 1.5 wt. % between 20° C. and 240° C. by thermogravimetric analysis.

In some embodiments, the disclosure provides a process for preparing a solid form of Compound (I) comprising washing a solution comprising Compound (I) and an organic solvent with an aqueous solution of a weak organic acid having a pKa less than or equal to 7 (7) to create a first organic layer and a first aqueous layer; and removing the first aqueous layer, leaving behind the first organic layer comprising Compound (I).

In some embodiments, the organic solvent comprises dichloromethane. In some embodiments, the organic solvent is dichloromethane.

In some embodiments, the weak organic acid having a pKa less than or equal to 7 is acetic acid.

In some embodiments, removing the first aqueous layer removes basic impurities that are more polar than Compound (I). In some embodiments, the basic impurities comprise at least one of (R)-3-(2-fluoro-4-phenoxyphenyl)-1-(piperidin-3-yl)-1H-pyrazolo[3,4-d]pyrimidin-4-amine, having the following structure:

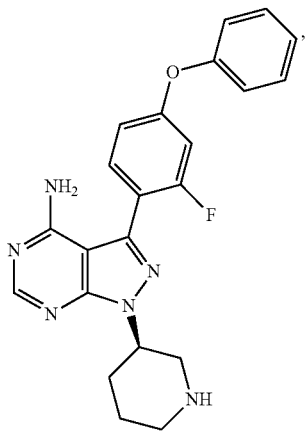 [SMILES: Nc1ncnc2c1c(-c1ccc(Oc3ccccc3)cc1F)nn2[C@@H]1CCCNC1]

or a pharmaceutically acceptable salt thereof;
2-methyl-2-(4-(oxetan-3-yl)piperazin-1-yl)propanal, having the following structure:

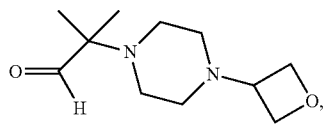

or a pharmaceutically acceptable salt thereof;
pyrrolidine; or
2-((R)-3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)-3-(pyrrolidin-1-yl)pentanenitrile, having the following structure:

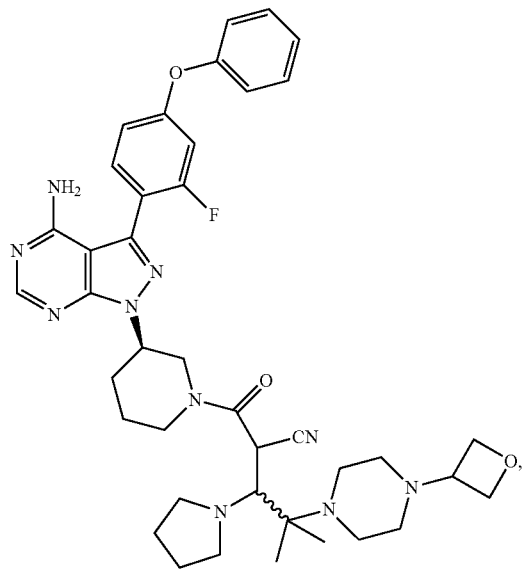 [SMILES: CC(C)(C(C(C#N)C(=O)N1CCC[C@@H](n2nc(-c3ccc(Oc4ccccc4)cc3F)c3c(N)ncnc32)C1)N1CCCC1)N1CCN(C2COC2)CC1]

or a pharmaceutically acceptable salt thereof.
In some embodiments, the process further comprises washing the first organic layer comprising Compound (I) with aqueous sodium bicarbonate. In some embodiments, washing the first organic layer comprising Compound (I) removes substantially all of the weak organic acid having a pKa≤7. In some embodiments, the weak organic acid having a pKa≤7 is acetic acid.

In some embodiments, the process further comprises adding a strong acid to the first organic layer; and concentrating the first organic layer by removing the organic solvent to provide a residue comprising Compound (I).

In some embodiments, the strong acid comprises methanesulfonic acid. In some embodiments, the strong acid is methanesulfonic acid.

In some embodiments, concentrating the first organic layer comprises distillation under reduced pressure.

In some embodiments, the residue comprising Compound (I) is a thin oil.

In some embodiments, the process further comprises cooling the residue comprising Compound (I) to a temperature between 0° C. and 10° C. In some embodiments, the temperature is 5° C.

In some embodiments, the process further comprises washing the residue comprising Compound (I) with water or an aqueous salt solution. In some embodiments, the aqueous salt solution is an aqueous solution of sodium chloride.

In some embodiments, the process further comprises adding a water-immiscible organic solvent to the first aqueous layer to provide a second organic layer, and a second aqueous layer comprising Compound (I); and removing the second organic layer.

In some embodiments, the water-immiscible organic solvent is dichloromethane.

In some embodiments, the process further comprises adjusting the pH of the first or second aqueous layer to a value between 1 and 5 by adding an aqueous base.

In some embodiments, the pH of the first or second aqueous layer is adjusted to 3.

In some embodiments, the aqueous base is an aqueous solution of an inorganic base.

In some embodiments, the aqueous base is an aqueous solution of potassium hydroxide.

In some embodiments, removing the second organic layer comprises distillation under reduced pressure.

In some embodiments, the process further comprises determining a level of a residual weak organic acid having a pKa≤7 in the first or second aqueous layer, and adjusting the level of the weak organic acid having a pKa≤7 to 0 wt. % to 8 wt. %.

In some embodiments, the weak organic acid having a pKa≤7 is acetic acid.

In some embodiments, adjusting the level comprises adding additional weak organic acid. In some embodiments, adjusting the level comprises adding additional acetic acid.

In some embodiments, the process further comprises adding an aqueous base to the first or second aqueous layer to obtain a pH between 8 and 11 and allowing a precipitate comprising Compound (I) to form.

In some embodiments, the pH is 9.5.

In some embodiments, the aqueous base is an aqueous solution of potassium hydroxide.

In some embodiments, the precipitate comprising Compound (I) is allowed to form for at least 3 hours at 20° C.

In some embodiments, the process further comprises isolating the precipitate comprising Compound (I) by filtering, and washing the isolated precipitate comprising Compound (I) with water.

In some embodiments, the process further comprises drying the filtered and washed precipitate comprising Compound (I) to provide a solid form of Compound (I).

In some embodiments, drying the filtered and washed precipitate comprising Compound (I) comprises drying under reduced vacuum with slight heat. In some embodiments, drying the filtered and washed precipitate comprising Compound (I) comprises drying under reduced vacuum with slight heat at 25° C.

In some embodiments, the process further comprises slurrying the isolated precipitate with water and filtering to isolate a solid form of Compound (I).

In some embodiments, the isolated precipitate is slurried with water at 15° C. for at least 1 hour prior to filtering. In some embodiments, filtering comprises drying under reduced vacuum with slight heat. In some embodiments, filtering comprises drying under reduced vacuum with slight heat at 25° C.

In some embodiments, the process provides a solid form of Compound (I) that is substantially free of degradation products. In some embodiments, the process provides a solid form of Compound (I) that is substantially free of dimers of Compound (I). In some embodiments, the process provides a solid form of Compound (I) that is substantially free of dimers of Compound (I) having the following structure:

is less than 5000 ppm; and/or the residual heptane level is less than 5000 ppm. In some embodiments, the process provides a solid form of Compound (I), wherein: the residual isopropyl acetate level is less than 500 ppm; and/or the residual heptane level is less than 500 ppm. In some embodiments, the process provides a solid form of Compound (I), wherein there is no detectable residual methanol in the solid form.

In some embodiments, the process provides a solid form of Compound (I), wherein the residual dichloromethane level is less than 1500 ppm. In some embodiments, the process provides a solid form of Compound (I), wherein the residual dichloromethane level is less than 1000 ppm. In some embodiments, the process provides a solid form of Compound (I), wherein the residual dichloromethane level is less than 500 ppm. In some embodiments, the process provides a solid form of Compound (I), wherein the residual dichloromethane level is less than 100 ppm.

In some embodiments, the process provides a solid form of Compound (I), characterized by a mean bulk density greater than 0.3 g/cc. In some embodiments, the process provides a solid form of Compound (I), characterized by a mean bulk density greater than 0.4 g/cc. In some embodiments, the process provides a solid form of Compound (I), characterized by a mean bulk density greater than 0.5 g/cc.

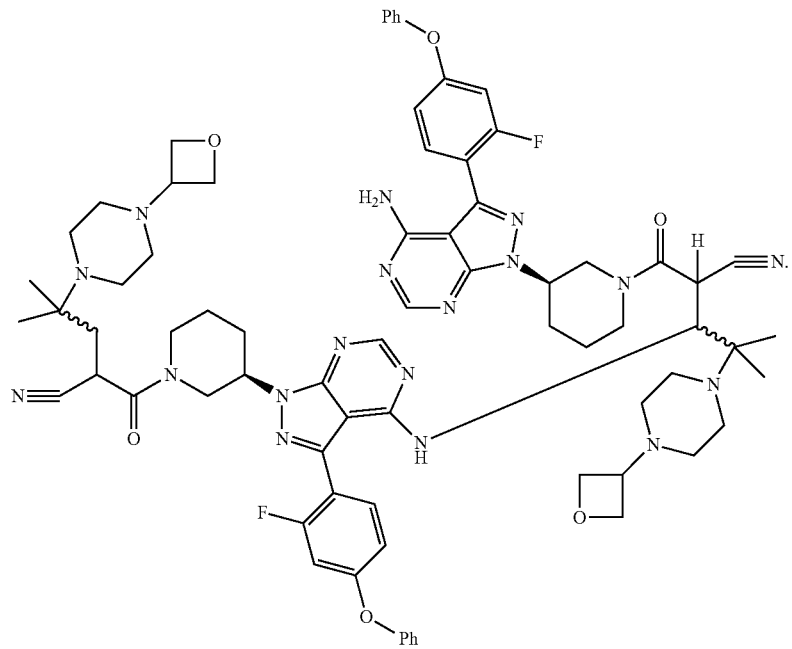 [SMILES: CC(C)(CC(C#N)C(=O)N1CCC[C@@H](n2nc(-c3ccc(Oc4ccccc4)cc3F)c3c(NC(C(C#N)C(=O)N4CCC[C@@H](n5nc(-c6ccc(Oc7ccccc7)cc6F)c6c(N)ncnc65)C4)C(C)(C)N4CCN(C5COC5)CC4)ncnc32)C1)N1CCN(C2COC2)CC1]

In some embodiments, the process provides a solid form of Compound (I), wherein dimers of Compound (I) comprises less than 3.5% by weight of the solid form of Compound (I).

In some embodiments, the process provides a solid form of Compound (I), wherein residual solvents comprise less than 1% of the solid form of Compound (I). In some embodiments, the process provides a solid form of Compound (I), wherein residual solvents comprise less than 0.5% of the solid form of Compound (I). In some embodiments, the process provides a solid form of Compound (I), wherein there is no detectable residual solvent in the solid form. In some embodiments, the process provides a solid form of Compound (I), wherein the residual isopropyl acetate level In some embodiments, the process provides a solid form of Compound (I), characterized by a mean bulk density greater than 0.6 g/cc. In some embodiments, the process provides a solid form of Compound (I), characterized by a mean bulk density between than 0.6 g/cc and 0.7 g/cc.

In some embodiments, the process provides a solid form of Compound (I), characterized by a mean tapped density greater than 0.5 g/cc. In some embodiments, the process provides a solid form of Compound (I), characterized by a mean tapped density greater than 0.6 g/cc. In some embodiments, the process provides a solid form of Compound (I), characterized by a mean tapped density greater than 0.7 g/cc. In some embodiments, the process provides a solid form of Compound (I), characterized by a mean tapped density greater than 0.8 g/cc. In some embodiments, the process provides a solid form of Compound (I), characterized by a mean tapped density between than 0.7 g/cc and 0.9 g/cc.

In some embodiments, the process provides a solid form of Compound (I), characterized by a Hausner ratio less than or equal to 1.2.

In some embodiments, the process provides a solid form of Compound (I), characterized by characterized by a wet particle size distribution having a $D_{10}$ value greater than 70 µm. In some embodiments, the process provides a solid form of Compound (I), characterized by characterized by a wet particle size distribution having a $D_{50}$ value greater than 200 µm. In some embodiments, the process provides a solid form of Compound (I), characterized by characterized by a wet particle size distribution having a $D_{90}$ value greater than 400 µm. In some embodiments, the process provides a solid form of Compound (I), characterized by characterized by a wet particle size distribution having a $D_{10}$ value greater than 70 µm and a $D_{50}$ value greater than 200 µm. In some embodiments, the process provides a solid form of Compound (I), characterized by characterized by a wet particle size distribution having a $D_{10}$ value greater than 70 µm, a $D_{50}$ value greater than 200 µm, and a $D_{90}$ value greater than 400 µm. In some embodiments, the process provides a solid form of Compound (I), characterized by characterized by a wet particle size distribution having a $D_{10}$ value greater than 70 µm and a $D_{90}$ value greater than 400 µm. In some embodiments, the process provides a solid form of Compound (I), characterized by characterized by a wet particle size distribution having a $D_{50}$ value greater than 200 µm and a $D_{90}$ value greater than 400 µm.

In some embodiments, the process provides a solid form of Compound (I), characterized by a mass loss of less than 5 wt. % between 20° C. and 240° C. by thermogravimetric analysis. In some embodiments, the process provides a solid form of Compound (I), characterized by a mass loss of less than 4 wt. % between 20° C. and 240° C. by thermogravimetric analysis. In some embodiments, the process provides a solid form of Compound (I), characterized by a mass loss of less than 3 wt. % between 20° C. and 240° C. by thermogravimetric analysis. In some embodiments, the process provides a solid form of Compound (I), characterized by a mass loss of less than 2 wt. % between 20° C. and 240° C. by thermogravimetric analysis. In some embodiments, the process provides a solid form of Compound (I), characterized by a mass loss of less than 1.5 wt. % between 20° C. and 240° C. by thermogravimetric analysis.

In some embodiments, the process provides a solid form of Compound (I), characterized by a glass transition temperature ($T_g$) greater than 90° C. at 0% relative humidity.

In some embodiments, the process provides a substantially amorphous solid form of Compound (I).

In some embodiments, the process further comprises micronizing particles of Compound (I).

In some embodiments, the micronization process provides fine particles of Compound (I). In some embodiments, the micronization process provides a solid form of Compound (I) characterized by a wet particle size distribution having a $D_{10}$ value less than 10 µm. In some embodiments, the process provides a solid form of Compound (I) characterized by a wet particle size distribution having a $D_{10}$ value less than 10 µm and a $D_{50}$ value less than 100 µm. In some embodiments, the micronization process provides a solid form of Compound (I) characterized by a wet particle size distribution having a $D_{10}$ value less than 10 µm and a $D_{90}$ value less than 200 µm. In some embodiments, the micronization process provides a solid form of Compound (I) characterized by a wet particle size distribution having a $D_{10}$ value less than 10 µm, a $D_{50}$ value less than 100 µm, and a $D_{90}$ value less than 200 µm.

In some embodiments, the process provides a solid form of Compound (I) characterized by a wet particle size distribution having a $D_{10}$ value between 1 µm and 2 µm. In some embodiments, the process provides a solid form of Compound (I) characterized by a wet particle size distribution having a $D_{50}$ value between 40 µm and 70 µm. In some embodiments, the process provides a solid form of Compound (I) characterized by a wet particle size distribution having a $D_{90}$ value between 100 µm and 150 µm.

In some embodiments, the process provides a solid form of Compound (I) characterized by a wet particle size distribution having a $D_{10}$ value between 1 m and 2 µm and a $D_{50}$ value between 40 µm and 70 µm. In some embodiments, the process provides a solid form of Compound (I) characterized by a wet particle size distribution having a $D_{10}$ value between 1 µm and 2 µm and a $D_{90}$ value between 100 µm and 150 µm. In some embodiments, the process provides a solid form of Compound (I) characterized by a wet particle size distribution having a $D_{50}$ value between 40 µm and 70 µm and a $D_{90}$ value between 100 µm and 150 µm.

In some embodiments, a solid form of the present disclosure is characterized by a wet particle size distribution having a $D_{10}$ value between 1 m and 2 µm, a $D_{50}$ value between 40 µm and 70 µm, and a $D_{90}$ value between 100 µm and 150 µm.

In some embodiments, the micronization process provides a stable solid form of Compound (I). In some embodiments, the micronization process provides a solid form of Compound (I) characterized by a mass loss of less than 5 wt. % between 20° C. and 240° C. by thermogravimetric analysis. In some embodiments, the micronization process provides a solid form of Compound (I) characterized by a mass loss of less than 3 wt. % between 20° C. and 240° C. by thermogravimetric analysis. In some embodiments, the micronization process provides a solid form of Compound (I) characterized by a mass loss of less than 2 wt. % between 20° C. and 240° C. by thermogravimetric analysis. In some embodiments, the micronization process provides a solid form of Compound (I) characterized by a mass loss of less than 1.5 wt. % between 20° C. and 240° C. by thermogravimetric analysis.

Conversion Processes for Preparing Solid Forms of Compound (I)

In some embodiments, the disclosure provides a process for preparing a solid form of Compound (I) comprising dissolving a crystalline form of Compound (I) in a solution comprising a water-immiscible organic solvent and brine; adding one equivalent of a strong acid to create an aqueous layer and an organic layer; removing the organic layer; concentrating the aqueous layer; adding an aqueous base to adjust the pH to a value between 8 and 11 to obtain a precipitate of a solid form of Compound (I); isolating the precipitate of the solid form of Compound (I) by filtering; rinsing the precipitate with water; and drying the precipitate to obtain a solid form of Compound (I).

In some embodiments, the water-immiscible organic solvent comprises dichloromethane. In some embodiments, the water-immiscible organic solvent is dichloromethane.

In some embodiments, the strong acid is methanesulfonic acid.

In some embodiments, concentrating the aqueous layer comprises distillation under reduced pressure. In some embodiments, concentrating the aqueous layer comprises distillation under reduced pressure at a temperature between 0° C. and 5° C.

In some embodiments, concentrating the aqueous layer removes residual organic solvent.

In some embodiments, the aqueous base is an aqueous potassium hydroxide solution. In some embodiments, the aqueous base is a 5% aqueous potassium hydroxide solution.

In some embodiments, the pH is adjusted to a value between 9 and 10.

In some embodiments, drying the precipitate comprises drying under vacuum with slight heat. In some embodiments, drying the precipitate comprises drying under vacuum with slight heat at 30° C.

In some embodiments, the process provides a substantially amorphous solid form of Compound (I).

In some embodiments, the process provides a substantially pure form of Compound (I).

In some embodiments, the process provides a solid form of Compound (I), characterized by a mass loss of less than 5 wt. % between 20° C. and 200° C. by thermogravimetric analysis. In some embodiments, the process provides a solid form of Compound (I), characterized by a mass loss of less than 4 wt. % between 20° C. and 200° C. by thermogravimetric analysis. In some embodiments, the process provides a solid form of Compound (I), characterized by a mass loss of less than 3 wt. % between 20° C. and 200° C. by thermogravimetric analysis. In some embodiments, the process provides a solid form of Compound (I), characterized by a mass loss of less than 2 wt. % between 20° C. and 200° C. by thermogravimetric analysis. In some embodiments, the process provides a solid form of Compound (I), characterized by a mass loss of less than 1.5 wt. % between 20° C. and 200° C. by thermogravimetric analysis. In some embodiments, the process provides a solid form of Compound (I), characterized by a mass loss of less than 1 wt. % between 20° C. and 200° C. by thermogravimetric analysis.

Indications

Solid forms of Compound (I) described herein can be useful for treating conditions mediated by BTK activity in mammals. In some embodiments, solid forms of Compound (I) described herein may be used to treat humans or non-humans.

Solid forms of Compound (I) described herein may be useful in treating *Pemphigus*. In some embodiments, solid forms of Compound (I) described herein may be used to treat *Pemphigus vulgaris*. In some embodiments, solid forms of Compound (I) described herein may be used to treat *Pemphigus foliaceus*.

*Pemphigus* is a rare B cell-mediated autoimmune disease that causes debilitating intraepithelial blisters and erosions on the skin and/or mucous membranes. *Pemphigus* carries a 10% mortality, generally due to infections arising from compromised tissues and treatment side effects, and affects approximately 0.1 to 0.5 people out of 100,000 each year (Scully et al., 2002; Scully et al., 1999). The characteristic intraepidermal blisters observed in *Pemphigus* patients are caused by the binding of IgG autoantibodies to certain keratinocyte desmosomal adhesion proteins, desmogleins 1 and 3 (Dsg1 and Dsg3), resulting in loss of cell adhesion (Amagai M et al., 2012; Diaz L A et al., 2000). B cells play key roles in the production of these autoantibodies and in cellular tolerance mechanisms.

Solid forms of Compound (I) described herein may be useful in treating immune thrombocytopenia.

Immune thrombocytopenia (commonly referred to as ITP) is characterized by autoantibody-mediated destruction of platelets and impaired platelet production, which result in thrombocytopenia and a predisposition to bleeding associated with morbidity and mortality. There is preliminary evidence to support the role of BTK inhibition in patients with autoimmune cytopenias (Rogers 2016, Montillo 2017), where sequential episodes of severe autoimmune hemolytic anemia and ITP ceased after initiation of treatment with ibrutinib, a BTK/EGFR/ITK inhibitor, in patients with chronic lymphatic leukemia (CLL).

Pharmaceutical Compositions

The solid forms described herein are useful as active pharmaceutical ingredients (APIs), as well as materials for preparing pharmaceutical compositions that incorporate one or more pharmaceutically acceptable excipients and are suitable for administration to human subjects. In some embodiments, these pharmaceutical compositions will be a pharmaceutical product, such as, e.g., a solid oral dosage form, such as tablets and/or capsules.

In some embodiments, the present disclosure provides a pharmaceutical composition comprising at least one solid form of Compound (I). In some embodiments, the present disclosure provides a pharmaceutical composition comprising at least one solid form of Compound (I) and at least one additional pharmaceutically acceptable excipient. Each excipient must be "pharmaceutically acceptable" in the sense of being compatible with the subject composition and its components not injurious to the patient. Except insofar as any conventional pharmaceutically acceptable excipient is incompatible with Compound (I), such as by producing any undesirable biological effect or otherwise interacting in a deleterious manner with any other component(s) of the pharmaceutically acceptable composition, its use is contemplated to be within the scope of this disclosure.

Some non-limiting examples of materials which may serve as pharmaceutically acceptable excipients include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, also discloses additional non-limiting examples of pharmaceutically acceptable excipients, as well as known techniques for preparing and using the same.

Pharmaceutical compositions disclosed herein may be administered orally, parenterally, by inhalation spray, topically, rectally, nasally, buccally, vaginally, or via an implanted reservoir. The term "parenteral," as used herein includes subcutaneous, intravenous, intramuscular, intra-articular, intra-synovial, intrasternal, intrathecal, intrahepatic, intralesional, and intracranial injection or infusion techniques. In some embodiments, the compositions of the disclosure are administered orally, intraperitoneally, or intravenously. Sterile injectable forms of the pharmaceutical compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans, and other emulsifying agents or bioavailability enhancers which are commonly used in the manufacture of pharmaceutically acceptable solid, liquid, or other dosage forms may also be used for the purposes of formulation.

Pharmaceutical compositions disclosed herein may also be orally administered in any orally acceptable dosage form including, but not limited to, capsules, tablets, aqueous suspensions, or solutions. When aqueous suspensions are required for oral use, the active ingredient is typically combined with emulsifying and suspending agents. If desired, certain sweetening, flavoring, or coloring agents may also be added.

Alternatively, pharmaceutical compositions disclosed herein may be administered in the form of suppositories for rectal administration. Suppositories can be prepared by mixing the agent with a suitable non-irritating excipient that is solid at room temperature but liquid at rectal temperature and therefore will melt in the rectum to release the drug. Such materials include, but are not limited to, cocoa butter, beeswax, and polyethylene glycols.

The pharmaceutical compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation or in a suitable enema formulation. Topically-transdermal patches may also be used.

For topical applications, the pharmaceutical compositions may be formulated in a suitable ointment containing the active component suspended or dissolved in at least one excipient. Excipients for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, pharmaceutical compositions disclosed herein can be formulated in a suitable lotion or cream containing the active components suspended or dissolved in at least one pharmaceutically acceptable excipient. Suitable excipients include, but are not limited to, mineral oil, sorbitan monostearate, polysorbate 60, cetyl esters wax, cetearyl alcohol, 2-octyldodecanol, benzyl alcohol, and water.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosing

In general, solid forms of Compound (I) will be administered in a therapeutically effective amount by any of the accepted modes of administration for agents that serve similar utilities. The effective dose for any particular mammal (e.g., any particular human) will depend upon a variety of factors including: the disorder being treated and the severity of the disorder; the specific pharmaceutical composition employed; the age, body weight, general health, sex and diet of the mammal; the time of administration, route of administration, the duration of the treatment; and like factors well known in the medical arts. In some embodiments, a therapeutically effective amount of at least one solid form of Compound (I) is administered to a mammal in need thereof. Therapeutically effective amounts of the solid forms disclosed herein may range from 0.01 to 500 mg per kg patient body weight per day, which can be administered in single or multiple doses. A suitable dosage level may be 0.01 to 250 mg/kg per day, 0.05 to 100 mg/kg per day, or 0.1 to 50 mg/kg per day. Within this range, in some embodiments, the dosage can be 0.05 to 0.5, 0.5 to 5, or 5 to 50 mg/kg per day. For oral administration, in some embodiments, the compositions can be provided in the form of tablets containing 1.0 to 1000 milligrams of the active ingredient, e.g., 1, 5, 10, 15, 20, 25, 50, 75, 100, 150, 200, 250, 300, 400, 500, 600, 750, 800, 900, and 1000 milligrams of the active ingredient.

In general, solid forms of this disclosure will be administered as pharmaceutical compositions by any one of the following routes: oral; systemic (e.g., transdermal, intranasal, or by suppository); topical; or parenteral (e.g., intramuscular, intravenous, or subcutaneous) administration. Illustratively, compositions can take the form of tablets, capsules, semisolids, powders, sustained release formulations, enteric coated or delayed release formulations, solutions, suspensions, elixirs, aerosols, or any other appropriate compositions.

All publications and patents mentioned herein are hereby incorporated by reference in their entirety as if each individual publication or patent was specifically and individually indicated to be incorporated by reference.

Claims or descriptions that include "or" or "and/or" between at least one members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all the group members are present in, employed in, or otherwise relevant to a given product or process.

Furthermore, the disclosure encompasses all variations, combinations, and permutations in which at least one limitation, element, clause, and descriptive term from at least one of the listed claims is introduced into another claim. For example, any claim that is dependent on another claim can be modified to include at least one limitation found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those of ordinary skill in the art will recognize or be able to ascertain using no more than routine experimentation, many equivalents to the specific embodiments of the disclosure described herein. Such equivalents are intended to be encompassed by the following claims.

EXAMPLES

The following examples are intended to be illustrative and are not meant in any way to limit the scope of the disclosure.

The synthetic schemes described below are meant to provide general guidance in connection with preparing compounds and solid forms of the present disclosure. One of ordinary skill in the art would understand that the preparations shown can be modified and/or optimized using general knowledge and techniques well-known in the art.

ABBREVIATIONS

DCM=dichloromethane
DMA=dimethyl acetamide
DME=dimethoxyethane
DMF=dimethylformamide
DMSO=dimethyl sulfoxide
EtOAc=ethyl acetate
EtOH=ethanol
IPA=isopropyl alcohol
IPAC=isopropyl acetate
MeOH=methanol
MTBE=Methyl tert-butyl ether
NMM=N-methyl morpholine
NMP=N-methyl pyrrolidine
PP=polypropylene
rpm=rotation per minute
TEA=triethylamine
TFA=trifluoroacetic acid
THF=tetrahydrofuran
THP=tetrahydropyran
TMS=Tris(trimethylsilyl)
TMSCl=Trimethylsilyl chloride Example 1: Spray Drying Process A A solution of Compound (I) in dichloromethane (prepared according to Example 31 on pages 86-87 of WO 2014/039899) was washed with pH 3 phosphate buffer to remove basic impurities that are more soluble than Compound (I) in the aqueous layer. The dichloromethane solution was then washed with pH 7 buffer and solvent exchanged into isopropyl acetate. The isopropyl acetate solution was then washed with pH 3 phosphate buffer, bringing Compound (I) into the aqueous layer and removing non-basic impurities. The pH of the aqueous layer was adjusted to pH 9 with 10% sodium hydroxide, and the aqueous layer was extracted with isopropyl acetate. Upon concentration under vacuum, Compound (I) was precipitated from heptane at 0° C., filtered and dried to give a white amorphous solid as a mixture of the (E) and (Z) isomers, as wet Compound (I). Wet Compound (I) was dissolved in methanol and spray dried at dryer inlet temperature of 125° C. to 155° C. and dryer outlet temperature of 48 to 58° C. to obtain the stable amorphous Compound (I) free base with levels of isopropyl acetate and heptane below 0.5% and 0.05%, respectively.

Example 2: Spray Drying Process B

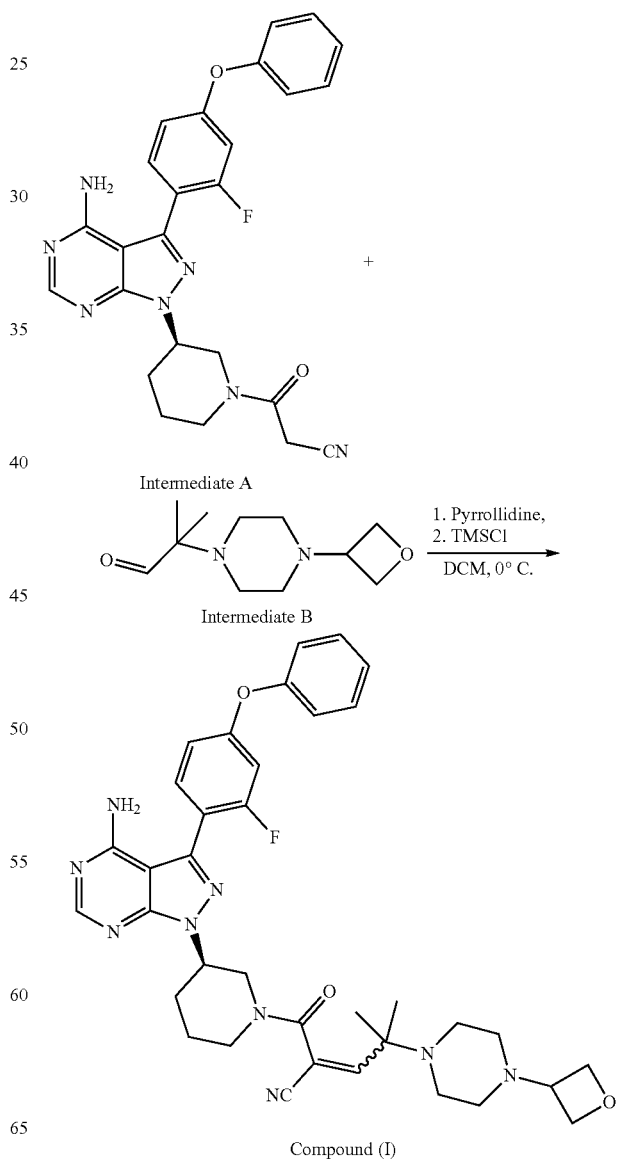

A jacketed reactor with overhead stirrer, condenser, nitrogen line, temperature probe, and recirculating fluid chiller/heater was charged with Intermediate A (20.2 kg) and Intermediate B (13.6 kg, 1.5 equiv). DCM (361.3 kg, 14.5 vol) was charged to the reactor. The mixture was agitated, and the batch cooled to 0° C. to 5° C. The reactor was charged with pyrrolidine (18.3 kg, 6 equiv) and then charged with TMSCl (18.6 kg, 4 eq). Stirring was continued at 0° C. to 5° C. for 0.5 to 1 hour.

At 0° C. to 5° C., acetic acid (2.0 equiv) was charged to the reactor followed by water (5 equiv). Stirring was continued at 0° C. to 5° C. for 1 to 1.5 hours. Water (10 equiv) was charged to the reactor, and the solution was adjusted to 20° C. to 25° C. The internal temperature was adjusted to 20° C. to 25° C. and the biphasic mixture was stirred for 15 to 20 mins. Stirring was stopped and phases allowed to separate for at least 0.5 h. The lower aqueous layer was removed.

Water (7 vol) was charged to the reactor. The pH was adjusted to 2.8-3.3 with a 10 wt. % solution of citric acid. Stirring was continued at 0 to 5° C. for 1 to 1.5 hours. Stirring was stopped and phases allowed to separate for at least 0.5 h. The lower aqueous layer was removed.

A jacketed reactor with overhead stirrer, condenser, nitrogen line, temperature probe, and recirculating fluid chiller/heater was charged with an approximately 9% solution of $NaHCO_3$ (1 vol) and the organic layer. The internal temperature was adjusted to 20° C. to 25° C., and the biphasic mixture was stirred for 15 to 20 mins. Stirring was stopped and phases allowed to separate for at least 0.5 h. The lower aqueous layer was removed. The aqueous layer was measured to have a pH greater than 7.

A jacketed reactor with overhead stirrer, condenser, nitrogen line, temperature probe and recirculating fluid chiller/heater was charged with the organic layer. The organic phase was distilled under vacuum at less than 25° C. to 4 total volumes. IPAC (15 vol) was charged to the reactor. The organic phase was distilled under vacuum at less than 25° C. to 10 total volumes. Water (15 vol) followed by pH 2.3 phosphate buffer were charged to the reactor at an internal temperature of 20° C. to 25° C. The pH adjusted to 3. Stirring was stopped and phases allowed to separate for at least 0.5 h. The organic phase was removed.

The following steps were repeated twice: IPAC (5 vol) was charged to the reactor containing the aqueous layer. Stirring was continued for 0.25 to 0.5 hours. Stirring was stopped and phases allowed to separate for at least 0.5 h. The organic phase was removed.

IPAC (15 vol) was charged to the reactor containing the aqueous layer. A pH 10 phosphate buffer was charged to the reactor and the pH adjusted to 10 with 14% NaOH solution. Stirring was continued for 1.5 to 2 hours. Stirring was stopped and phases allowed to separate for at least 0.5 h. The aqueous layer was discarded. The organic layer was dried over brine.

The organic solution was distilled under vacuum at less than 25° C. to 5 total volumes.

A jacketed reactor with overhead stirrer, condenser, nitrogen line, temperature probe and recirculating fluid chiller/heater was charged with n-heptane (20 vol). The internal temperature was adjusted to 0 to 5° C., and the IPAC solution was added.

The suspension was filtered. The filter cake was washed with n-heptane and the tray was dried at 35° C. Compound (I) (24.6 kg) was isolated in 86% yield.

Compound (I) was dissolved in methanol (6 kg) and spray dried to remove residual IPAC and n-heptane.

Example 3: Precipitation Process A

A solution of Compound (I) in dichloromethane (prepared according to Example 31 on pages 86-87 of WO 2014/039899) was quenched with acetic acid and water, followed by washing with pH 3 aqueous solution to remove basic impurities that are more soluble than Compound (I) in the aqueous layer. Washing was repeated as needed to reduce impurities. Methanesulfonic acid was added to the dichloromethane solution, and the dichloromethane solution was concentrated by distillation under reduced pressure, followed by addition of 1% NaCl aqueous solution and isopropyl acetate before adjustment of pH to approximately 3 with potassium hydroxide. The isopropyl acetate layer was removed and discarded. The aqueous layer containing Compound (I) was washed with isopropyl acetate to remove hydrophobic impurities. Washing was repeated as needed to reduce related substance impurities. Residual isopropyl acetate was removed by distillation under reduced pressure. The aqueous solution containing Compound (I) was cooled to 0 to 5° C. before adjusting the pH to approximately 9 with potassium hydroxide. The free base of Compound (I) was allowed to precipitate and maturate at 20° C. for 20 hours. The mixture temperature was then adjusted to 20° C. to 25° C., and the hydrate impurity was verified to be less than 0.3% (<0.3%). The cake of the free base of Compound (I) was filtered and washed as needed to reduce conductivity. The cake was then allowed to dry on the filter under vacuum and nitrogen swept to reduce water content by Karl-Fischer (KF<50%) before transferring to the oven for drying. The wet cake of the free base of Compound (I) was dried under vacuum at 25° C. until water content by Karl-Fischer was less than 1.5% (KF<1.5%), and then delumped by milling to yield a uniform white amorphous solid as a mixture of the (E) and (Z) isomers, with no detectable levels of isopropyl acetate or heptane.

Example 4: Precipitation Process B

A solution of Compound (I) in dichloromethane (prepared according to Example 31 on pages 86-87 of WO 2014/039899) was quenched with acetic acid and water, followed by washing with pH 3 aqueous solution to remove basic impurities that are more soluble than Compound (I) in the aqueous layer. The washing was repeated as needed to reduce residual solvents and impurities. The dichloromethane solution was then washed with saturated sodium bicarbonate (pH>7). Dichloromethane was removed by distillation under reduced pressure, followed by addition of water and isopropyl acetate. The pH of the aqueous layer was adjusted to pH to 2.8-3.3 with 2 M aqueous sulfuric acid ($H_2SO_4$) at 0-5° C., and the mixture was stirred and settled. After phase separation removal of the organic layer, the aqueous layer was washed with isopropyl acetate three times and the residual isopropyl acetate in aqueous layer was distilled out under vacuum at a temperature below 25° C. and the solution was basified with 5% aqueous KOH to pH 9-10 to a slurry. The resulting suspension was stirred and warmed up to 20° C. to 25° C. and aged for 20 h. The product was filtered and washed with water and dried to give white solid in 86% yield.

Example 5: Precipitation Process C

A solution of Compound (I) in dichloromethane (prepared according to Example 31 on pages 86-87 of WO 2014/039899) was quenched with acetic acid and water, followed by washing to remove basic impurities that are more soluble than Compound (I) in the aqueous layer. Washing was repeated as needed to reduce impurities. Methanesulfonic acid was added to the dichloromethane solution, and the dichloromethane solution was concentrated under reduced pressure to obtain a thin oil. The concentrated oil was cooled to approximately 5° C. before washing with an aqueous solution of sodium chloride. The organic phase was discarded. Washing of the aqueous layer was repeated as needed with dichloromethane to remove low level impurities. The pH of the aqueous solution was adjusted to approximately 3 with an aqueous solution of potassium hydroxide. Residual dichloromethane was removed under reduced pressure. The level of residual acetic acid was determined by, for example, titration. The aqueous solution containing Compound (I) was cooled to a temperature between 0° C. and 5° C. Acetic acid was present at 0 wt. % to 8 wt. %. Acetic acid level was 0 wt. % if the aqueous acid solution was washed with aqueous sodium bicarbonate or another aqueous inorganic base. Optionally, additional acetic acid was added to achieve a 0 wt. % to 8 wt. % acetic acid level. An aqueous solution of potassium hydroxide was constantly charged to the aqueous solution to obtain a pH to approximately 9.5. The free base of Compound (I) was allowed to precipitate and maturate at approximately 20° C. for least 3 hours. The cake (wet solid) of the free base of Compound (I) was filtered and washed with water. The wet cake was then dried under reduced vacuum with slight heat. Alternatively, instead of washing the wet cake with water, the wet cake was reslurried with water at approximately 15° C. for at least 1 hour before filtering. The free base of Compound (I) in the form of a wet cake was dried under vacuum with slight heat at 25° C.

Figure 12:
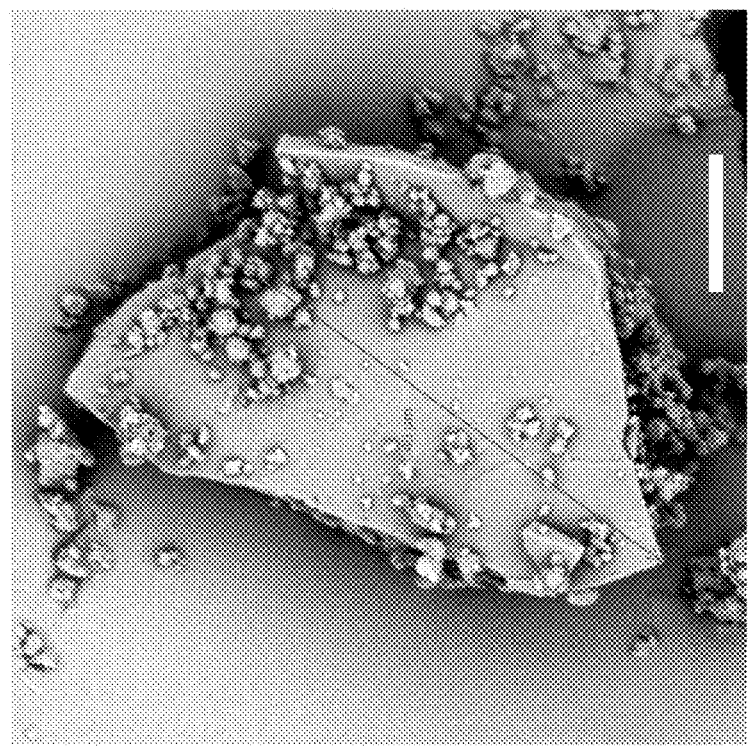
FIG. 12 depicts an example scanning electron microscopy (SEM) image of filtered particles of Compound (I) prepared via precipitation at 0 wt. % acetic acid (scale bar: 10 μm).
Figure 13:
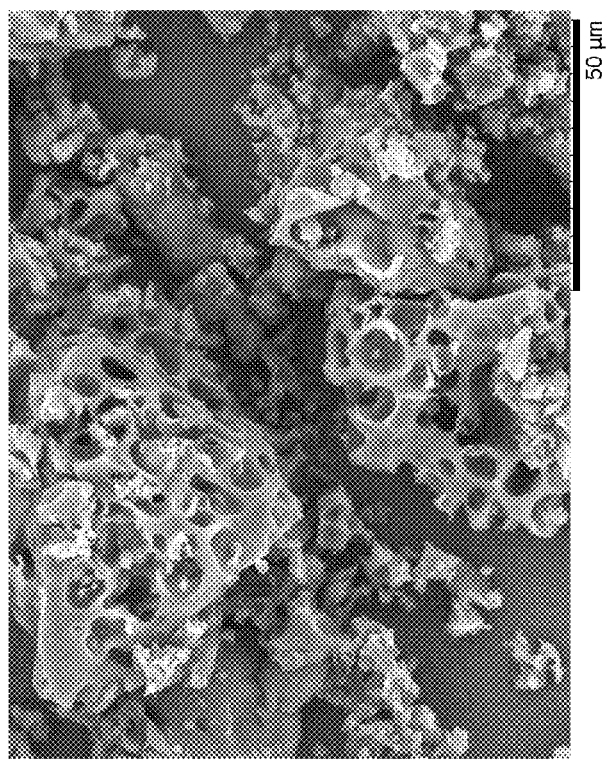
FIG. 13 depicts an example SEM image of filtered particles of Compound (I) prepared via precipitation at 3 wt. % acetic acid.
Figure 14:
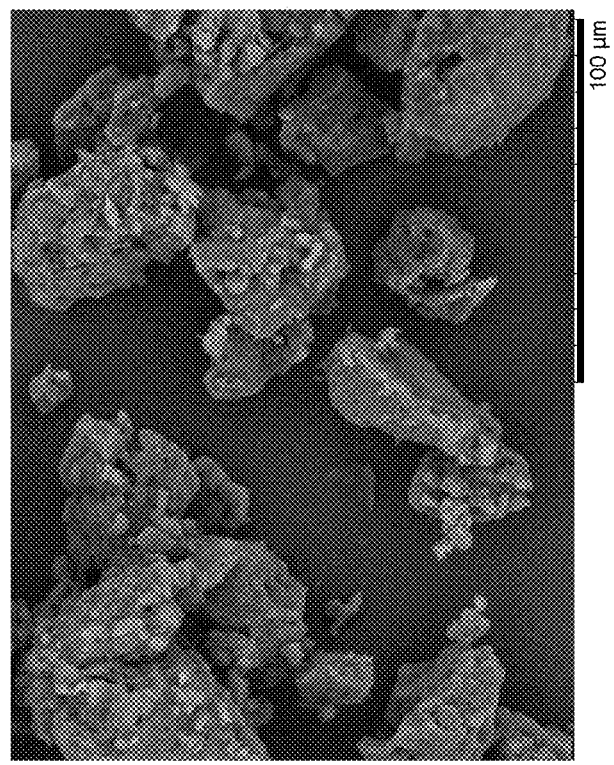
FIG. 14 depicts an example SEM image of filtered particles of Compound (I) prepared via precipitation at 5 wt. % acetic acid.
Figure 15:
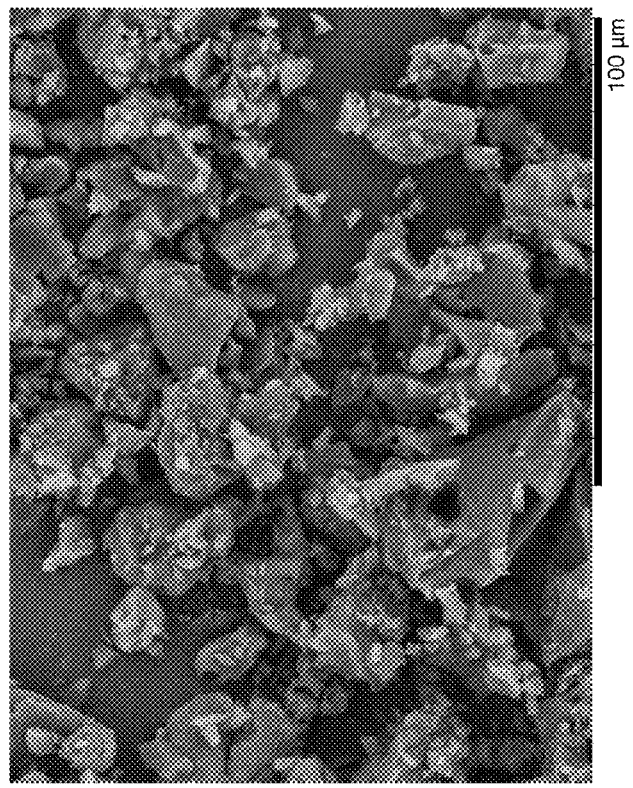
FIG. 15 depicts an example SEM image of filtered particles of Compound (I) prepared via precipitation at 8 wt. % acetic acid.
Figure 16:
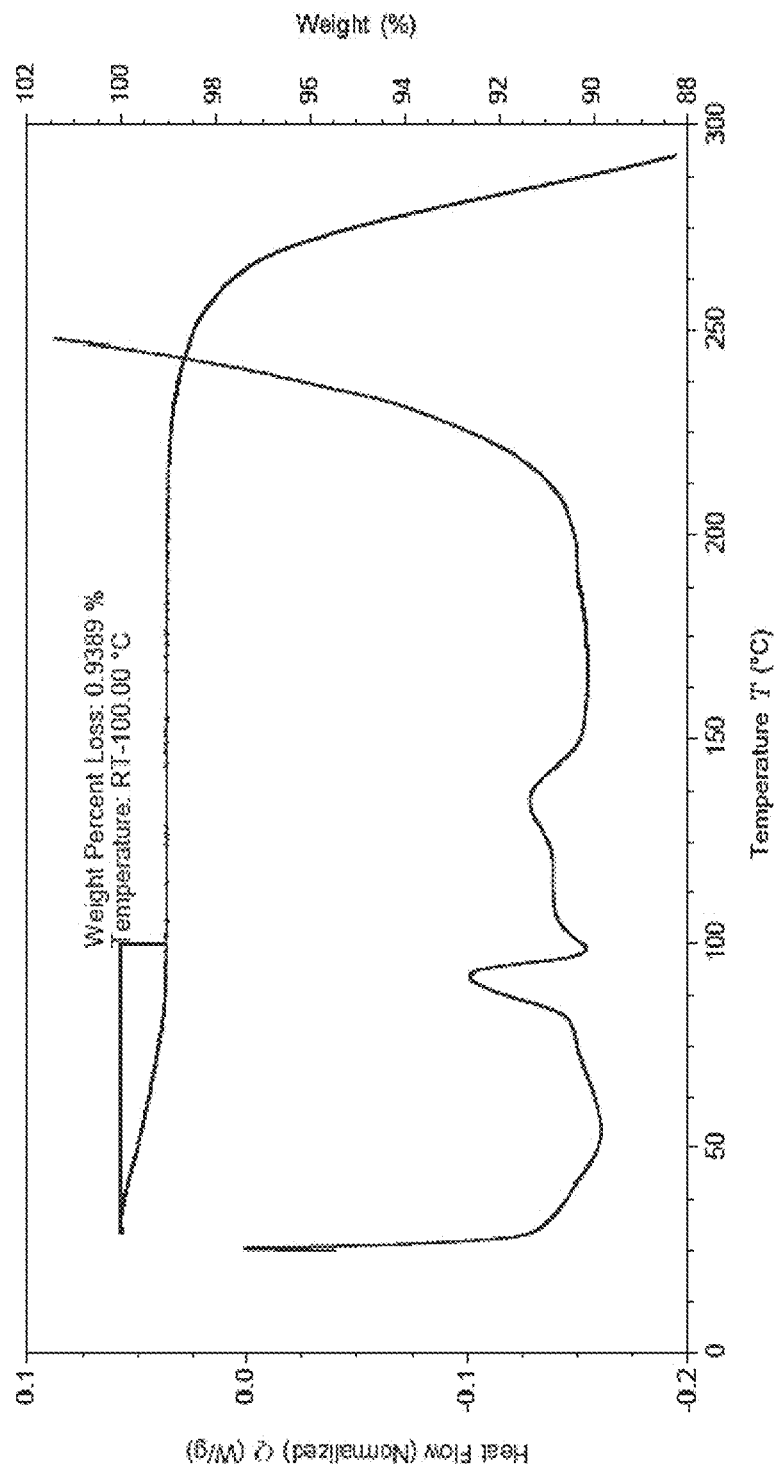
FIG. 16 depicts an example combined DSC-TGA plot for a solid form of Compound (I) prepared by a conversion process described herein.

FIGS. 12-15 are example SEM images showing the variable morphologies of particles of Compound (I) during the filtration step to isolate Compound (I) based on the amount acetic acid added during the initial step in the precipitation of Compound (I) (FIG. 12: at 0 wt. % acetic acid; FIG. 13: at 3 wt. % acetic acid; FIG. 14: at 5 wt. % acetic acid; FIG. 15: at 8 wt. % acetic acid). Filtration speed depended on the morphology and was the fastest for 0 wt. % acetic acid. At 1 wt. % acetic acid, the filtration speed diminished considerably, improving at 2 wt. % to 3 wt. % acetic acid. Morphologies with more open holes (such as, e.g., more porous particles) resulted in improved filtration speeds, whereas more compact particles resulted in decreased filtration speed.

Example 6: Conversion of a Crystalline Form of Compound (I) to an Amorphous Form 9.8 grams of a crystalline form of Compound (I) were dissolved in approximately 20 mL of dichloromethane and approximately 120 mL of brine solution. Then, approximately 1 equivalent of methanesulfonic acid was added. The pH was approximately 2. The layers were separated. The aqueous layer was concentrated at a temperature between 0° C. and 5° C. to remove residual dichloromethane before slowly adding aqueous KOH solution (approximately 5%) to adjust the pH to a value between 9 and 10. During aqueous KOH addition, an amorphous form of Compound (I) precipitated out. The slurry was slowly warmed to room temperature and then was stirred for approximately 24 hours before filtering and rinsing the wet cake with water. The wet cake was dried under vacuum with slight heat at approximately 30° C. to provide 7 grams of a white to an off-white solid (87% yield and 98.4% purity). XRPD showed that the product was an amorphous solid form of Compound (I).

Example 7: Micronization of Compound (I) Particles Obtained by Precipitation Processes A fluid jet mill equipment was used during lab scale jet milling trials. The fluid jet mill equipment includes a flat cylindrical chamber with 1.5" diameter, fitted with four symmetric jet nozzles which are tangentially positioned in the inner wall. Prior to feeding material to the fluid jet mill in each trial, the material was sieved in a 355 m screen to remove any agglomerates and avoid blocking of the nozzles during the feed of material to the micronization chamber. The material to be processed was drawn into the grinding chamber through a vacuum created by the venturi (P_vent~0.5-1.0 bar above P_grind). The feed flow rate of solids (F_feed) was controlled by a manual valve and an infinite screw volumetric feeder. Compressed nitrogen was used to inject the feed material; compressed nitrogen was also used for the jet nozzles in the walls of the milling chamber. Compressed fluid issuing from the nozzles expands from P_grind and imparts very high rotational speeds in the chamber. Accordingly, material is accelerated by rotating and expanding gases and subjected to centrifugal forces. Particles move outward and are impacted by high velocity jets, directing the particles radially inward at very high speeds. Rapidly moving particles impact the slower moving path of particles circulating near the periphery of the chamber. Attrition takes place due to the violent impacts of particles against each other. Particles with reduced size resulting from this sequence of impacts are entrained in the circulating stream of gas and swept against the action of centrifugal force toward the outlet at the center. Larger particles in the gas stream are subjected to a centrifugal force and returned to the grinding zone. Fine particles are carried by the exhaust gas to the outlet and pass from the grinding chamber into a collector.

The feeder has continuous feed rate control; however, to more precisely control the feed rate, the full scale of feed rates was arbitrary divided in 10 positions. To calibrate F feed, the feeder was disconnected from milling chamber and 10 g of Compound (I) powder was fed through the feeder operating at various feed rate positions. The mass of powder flowing through the feeder over 6 minutes was marked. The resulting feed rate was directly proportional to feeder position. After processing each of the four trials, the jet mill was stopped, micronized product removed from the container, and the milling chamber checked for any powder accumulation.

Variables/Parameters

| | |
|---|---|
| F_feed | Feed flow rate of solids [kg/h] |
| P_grind | Grinding pressure inside the drying chamber [bar] |
| P_vent | Feed pressure in the venturi [bar] |

Example 8: Residual Solvent Levels

Retention of process solvents (i.e., residual solvents) depends on van der Waals' forces that are unique to and an inherent property of each molecule. Additionally, solvent retention depends how the API solid is formed, isolated, washed, and dried (i.e., during the manufacturing process). Because residual solvents may pose safety risks, pharmaceutical processes should be designed to minimize residual solvent levels (e.g., to result in residual solvent levels below the limits established in the ICH guidelines).

Residual solvent analysis was performed using gas chromatography-mass spectrometry. The residual solvent levels in solid forms of Compound (I) prepared by spray drying processes described herein and precipitation processes described herein are provided in Table 2. The residual solvent levels in crude Compound (I) listed in Table 2 are comparable to the residual solvent levels in crude Compound (I) prepared according to the procedures detailed in Example 31 of WO 2014/039899 and Example 1 of WO 2015/127310.

TABLE 2

Residual solvent levels in solid forms of Compound (I)

| Solvent | Solvent levels in crude Compound (I) (before spray drying) | Solvent levels in Compound (I) produced by a spray drying process described herein | Solvent levels in Compound (I) produced by a precipitation process described herein |
|---|---|---|---|
| Isopropyl acetate | 2.00% | 3081 ppm | <500 ppm |
| Heptane (n-Heptane) | 5.00% | 426 ppm | <500 ppm |
| Methanol | None | 302 ppm | None |

Example 9: Wet Particle Size Distribution

Table 3 provides wet particle size distributions for several distinct solid forms of Compound (I). Comparator 1 corresponds to the solid form of Compound (I) prepared substantially in accordance with the process detailed in Step 1A in Example 1 of WO 2015/127310. Comparator 2 corresponds to the solid form of Compound (I) prepared substantially in accordance with the process detailed in Example 31 of WO 2014/039899.

Wet particle size distributions were measured using a Malvern Mastersizer 3000 laser diffraction particle size analyzer, with stir speed set at 2200 rpm. Heptane with 0.2% by volume of Span 80 was used as dispersant. To obtain distribution measurements, the Hydro MV medium volume automated dispersion unit was filled with dispersant and aligned. The background was then measured. 80 to 100 mg of sample weighed into a 20 mL vial, to which approximately 3 mL of dispersant was added. The mass was adjusted based on the particle size, with obscuration between 5% and 16%. The whole sample was added to the Hydro MV unit, and the sample was analyzed five times after a 160 second pre-measurement delay. Analysis time was 20 seconds (10 seconds with the red laser, 10 seconds with the blue laser) with no delay between measurements. Data obtained was processed using Mie theory with a sample refractive index of 1.69 and absorption index of 0.1, using the general purpose model with normal sensitivity and the non-spherical particle type. 15 sets of raw data were averaged to form the Global Mean, which represents the average for a sample. If the sample was determined to be variable, further preparations were examined to determine which results were anomalous. Any anomalous results were discarded. Samples were thoroughly mixed prior to sampling (e.g., some samples were aliquoted using a spinning riffler).

TABLE 3

Wet particle size distributions for solid forms of Compound (I)

| Solid form of Compound (I) | $D_{10}$ (μm) | $D_{50}$ (μm) | $D_{90}$ (μm) |
|---|---|---|---|
| Comparator 1 | 18.3 | 237 | 694 |
| Comparator 2 | 56.9 | 258 | 575 |
| Compound (I) prepared by a precipitation process described herein (micronized) | 1.9 | 55.8 | 123 |
| Compound (I) prepared by a precipitation process described herein (not micronized) | 70.7-125 | 236-366 | 476-683 |
| Compound (I) prepared by a spray drying process described herein | 5.24 | 13.3 | 28.4 |

Example 10: Mean Bulk Density, Mean Tapped Density, and Hausner Ratio Determination Mean bulk density and mean tapped density were determined using a modified method based on USP <616>. Powder was poured into a clean, dry pre-weighed 25 mL cylinder. Powder was added to a total volume of 20 mL to 25 mL without compacting the sample. The mass and initial volume ($V_o$) of the powder were recorded. The mean bulk density was determined as the average of the mass over initial volume across multiple samples. To determine mean tapped density, the sample was tapped using a Copley JV2000 tapped density tester using the following number of taps: 500, 750, and sets of 1250 taps up to 10,000. The volume was recorded after each set of taps, and the sample was tapped until it reached a constant volume ($V_f$). The mean tapped density was determined as the average of mass over constant volume across multiple samples. Each sample was analyzed in duplicate. The Hausner ratio was calculated as the ratio of initial volume to the constant volume ($V_o/V_f$).

Table 4 provides the mean bulk density, mean tapped density, and Hausner ratio for several distinct solid forms of Compound (I). As above, Comparator 1 corresponds to the solid form of Compound (I) prepared substantially in accordance with the process detailed in Step 1A in Example 1 of WO 2015/127310. Also, as above, Comparator 2 corresponds to the solid form of Compound (I) prepared substantially in accordance with the process detailed in Example 31 of WO 2014/039899.

TABLE 4

Mean bulk densities, mean tapped densities, and Hausner ratios for solid forms of Compound (I)

| Solid form of Compound (I) | Mean bulk density (g/cc) | Mean tapped density (g/cc) | Hausner ratio |
|---|---|---|---|
| Comparator 1 | 0.28 | 0.39 | 1.4 |
| Comparator 2 | 0.20 | 0.27 | 1.4 |
| Compound (I) prepared by a precipitation process described herein (micronized) | 0.21 | 0.27 | 1.2 |
| Compound (I) prepared by a precipitation process described herein (not micronized) | 0.60-0.68 | 0.74-0.81 | 1.2 |
| Compound (I) prepared by a spray drying process described herein | 0.20 | 0.28 | 1.4 |

Example 11: Thermogravimetric Analysis

Thermal gravimetric analysis of the samples was performed using the TA Instruments Q5000 TGA. Example TGA thermal curves depicting the mass loss described below over comparable temperature ranges are provided in FIGS. 1-6.

Table 5 provides thermogravimetric analysis data for several distinct solid forms of Compound (I), including mass loss information from multiple replicates across different temperature ranges. As above, Comparator 1 corresponds to the solid form of Compound (I) prepared substantially in accordance with the process detailed in Step 1A in Example 1 of WO 2015/127310. Also, as above, Comparator 2 corresponds to the solid form of Compound (I) prepared substantially in accordance with the process detailed in Example 31 of WO 2014/039899. Comparator 3 corresponds to the solid form of Compound (I) prepared substantially in accordance with the process detailed in Step 1 in Example 1 of WO 2015/127310.

TABLE 5

TGA analysis for solid forms of Compound (I)

| Solid form of Compound (I) | Mass loss during TGA |
|---|---|
| Comparator 1 | 3.3% mass loss between 40° C. and 118° C. |
| | 3.2% mass loss between 118° C. and 237° C. |
| Comparator 2 | 3.7% mass loss between 40° C. and 135° C. |
| | 2.3% mass loss between 135° C. and 233° C. |
| Comparator 3 | 3.8% mass loss between 30° C. and 100° C. |
| | 17.6% mass loss between 100° C. and 140° C. |
| Compound (I) prepared by a precipitation process described herein (micronized) | 1.0% mass loss between 44° C. and 230° C. |
| Compound (I) prepared by a precipitation process described herein (not micronized) | 1.9% mass loss between 43° C. and 230° C.; 0.8% mass loss between 30° C. and 190° C.; 0.4% mass loss between 40° C. and 205° C.; 0.7% mass loss between 40° C. and 225° C. |
| Compound (I) prepared by a spray drying process described herein | 1.2% mass loss between 35° C. and 230° C. |

Example 12: Thermal Analysis by Differential Scanning Calorimetry

Modulated differential scanning calorimetry (DSC) analysis was completed with a TA Instrument Q2000 DSC. The samples were heated at 2° C. min$^{-1}$, temperature modulation parameters of 1±0.318° C. (amplitude), and over a temperature range of −80° C. to 200° C. The samples were analyzed using a closed aluminum pan. Example DSC thermograms for solid forms of Compound (I) at 0% relative humidity ("RH") are shown in FIGS. 7-11.

Table 6 provides glass transition temperature data for several distinct solid forms of Compound (I). As above, Comparator 1 corresponds to the solid form of Compound (I) prepared substantially in accordance with the process detailed in Step 1A in Example 1 of WO 2015/127310. Also, as above, Comparator 2 corresponds to the solid form of Compound (I) prepared substantially in accordance with the process detailed in Example 31 of WO 2014/039899. Also, as above, Comparator 3 corresponds to the solid form of Compound (I) prepared substantially in accordance with the process detailed in Step 1 in Example 1 of WO 2015/127310.

TABLE 6

DSC analysis for solid forms of Compound (I)

| Solid form of Compound (I) | $T_g$ at 25° C., 0% RH | $T_g$ at 25° C., 60% RH |
|---|---|---|
| Comparator 1 | 71.7° C. (68.7° C. repeat) | 62.8° C. (55.0° C. repeat) |
| Comparator 2 | 90.1° C. | 90.4° C. (89.6° C. repeat) |
| Comparator 3 | 90.1° C. | — |
| Compound (I) prepared by precipitation process described herein (not micronized) | 93.8° C. to 96.5° C. | 69.6° C. |
| Compound (I) prepared by spray drying process described herein | 93.8° C. | — |

What is claimed is:

1. A solid form of Compound (I):

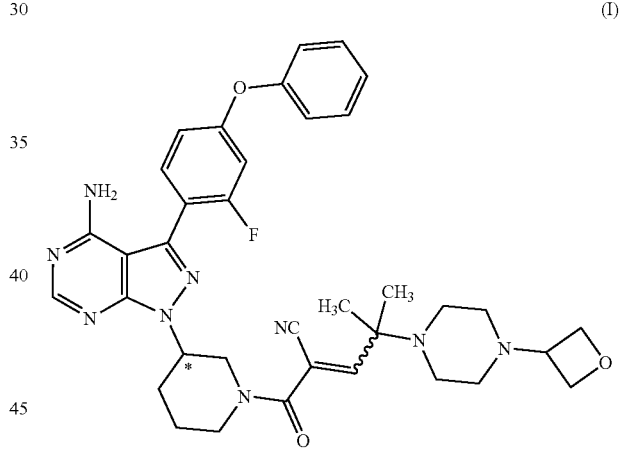

(I)

wherein the solid form is characterized by a mean bulk density greater than 0.3 g/cc.

2. The solid form according to claim 1, wherein the solid form is characterized by a mean tapped density between 0.7 g/cc and 0.9 g/cc.

3. The solid form according to claim 1, wherein the solid form is characterized by a Hausner ratio less than or equal to 1.2.

4. The solid form according to claim 1, wherein the solid form is characterized by a total level of residual solvents less than 1%.

5. The solid form according to claim 1, wherein the solid form is characterized by any one of the following:
   (i) a residual dichloromethane level less than 1500 ppm; or
   (ii) a residual methanol level less than 3000 ppm; or
   (iii) a residual heptane level less than 5000 ppm; or
   (iv) a residual isopropyl acetate level less than 5000 ppm; or (v) a residual dichloromethane level less than 1500 ppm, a residual methanol level less than 3000 ppm, a residual heptane level less than 5000 ppm, and a residual isopropyl acetate level less than 5000 ppm.

6. The solid form according to claim 1, wherein the solid form is characterized by any one of the following:
   (i) a mass loss of less than 5 wt. % between 20° C. and 240° C. by thermogravimetric analysis; or
   (ii) a glass transition temperature ($T_g$) greater than 90° C. at 0% relative humidity; or
   (iii) a mass loss of less than 5 wt. % between 20° C. and 240° C. by thermogravimetric analysis and a glass transition temperature ($T_g$) greater than 90° C. at 0% relative humidity.

7. The solid form according to claim 1, wherein the solid form is characterized by any one of the following:
   (i) a wet particle size distribution having a $D_{10}$ value greater than 70 μm; or
   (ii) a wet particle size distribution having a $D_{50}$ value greater than 200 μm; or
   (iii) a wet particle size distribution having a $D_{90}$ value greater than 400 μm; or
   (iv) a wet particle size distribution having a $D_{10}$ value greater than 70 μm and a wet particle size distribution having a $D_{50}$ value greater than 200 μm; or
   (v) a wet particle size distribution having a $D_{10}$ value greater than 70 μm, a wet particle size distribution having a $D_{50}$ value greater than 200 μm, and a wet particle size distribution having a $D_{90}$ value greater than 400 μm.

8. The solid form according to claim 1, wherein the solid form is substantially amorphous.

9. A pharmaceutical composition comprising at least one pharmaceutically acceptable excipient and the solid form according to claim 1.

10. A solid form of Compound (I):

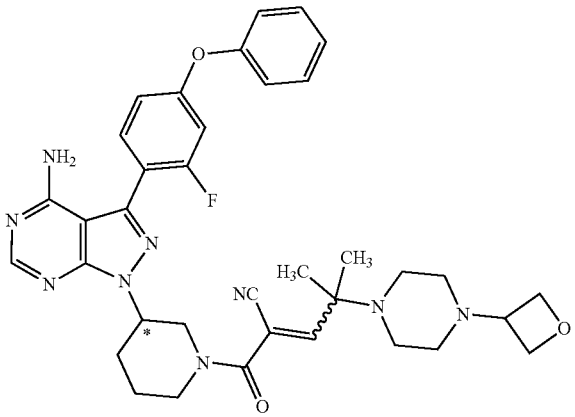

(I)

wherein the solid form is characterized by a wet particle size distribution having a $D_{10}$ value less than 10 μm.

11. The solid form according to claim 10, wherein the solid form is characterized by any one of the following:
    (i) a mean bulk density less than 0.3 g/cc; or
    (ii) a mean tapped less than 0.3 g/cc; or
    (iii) a mean bulk density less than 0.3 g/cc and a mean tapped less than 0.3 g/cc.

12. The solid form according to claim 10, wherein the solid form is characterized by a total level of residual solvents less than 1%.

13. The solid form according to claim 10, wherein the solid form is characterized by any one of the following:
    (i) a residual heptane level less than 500 ppm; or
    (ii) a residual methanol level less than 500 ppm; or
    (iii) a residual dichloromethane level less than 1500 ppm; or
    (iv) a residual isopropyl acetate level less than 4000 ppm; or
    (v) a residual heptane level less than 500 ppm, a residual methanol level less than 500 ppm, a residual dichloromethane level less than 1500 ppm, and a residual isopropyl acetate level less than 4000 ppm.

14. The solid form according to claim 10, wherein the solid form is characterized by any one of the following:
    (i) a mass loss of less than 5 wt. % between 20° C. and 240° C. by thermogravimetric analysis; or
    (ii) a glass transition temperature ($T_g$) greater than 90° C. at 0% relative humidity; or
    (iii) a mass loss of less than 5 wt. % between 20° C. and 240° C. by thermogravimetric analysis and a glass transition temperature ($T_g$) greater than 90° C. at 0% relative humidity.

15. The solid form according to claim 10, wherein the solid form is characterized by any one of the following:
    (i) a wet particle size distribution having a $D_{10}$ value between 1 μm and 2 μm; or
    (ii) a wet particle size distribution having a $D_{10}$ value between 5 μm and 6 μm; or
    (iii) a wet particle size distribution having a $D_{50}$ value less than 100 μm; or
    (iv) a wet particle size distribution having a $D_{90}$ value less 200 μm; or
    (v) a wet particle size distribution having a $D_{10}$ value between 1 μm and 2 μm, a wet particle size distribution having a $D_{10}$ value between 5 μm and 6 μm, a wet particle size distribution having a $D_{50}$ value less than 100 μm, and a wet particle size distribution having a $D_{90}$ value less 200 μm.

16. The solid form according to claim 10, wherein the solid form is substantially amorphous.

\* \* \* \* \*